(12) United States Patent
McCormack et al.

(10) Patent No.: US 10,149,673 B2
(45) Date of Patent: *Dec. 11, 2018

(54) FACET JOINT IMPLANTS AND DELIVERY TOOLS

(71) Applicant: PROVIDENCE MEDICAL TECHNOLOGY, INC., Lafayette, CA (US)

(72) Inventors: Bruce M. McCormack, San Francisco, CA (US); Jeffrey D. Smith, Clayton, CA (US)

(73) Assignee: PROVIDENCE MEDICAL TECHNOLOGY, INC., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/687,218

(22) Filed: Apr. 15, 2015

(65) Prior Publication Data

US 2015/0216518 A1 Aug. 6, 2015

Related U.S. Application Data

(60) Continuation of application No. 13/614,281, filed on Sep. 13, 2012, now Pat. No. 9,011,492, which is a
(Continued)

(51) Int. Cl.
*A61B 17/02* (2006.01)
*A61B 17/16* (2006.01)
(Continued)

(52) U.S. Cl.
CPC ........ *A61B 17/025* (2013.01); *A61B 17/1604* (2013.01); *A61B 17/1659* (2013.01);
(Continued)

(58) Field of Classification Search
CPC ... A61B 17/88; A61B 2017/681; A61B 17/70; A61F 2/4611; A61F 2/4614
See application file for complete search history.

(56) References Cited

U.S. PATENT DOCUMENTS

| 1,934,962 A | 11/1933 | Barry |
| 2,708,376 A | 5/1955 | Booth |
| (Continued) | | |

FOREIGN PATENT DOCUMENTS

| DE | G9304368.6 U1 | 5/2003 |
| FR | 2722980 A1 | 2/1996 |
| (Continued) | | |

OTHER PUBLICATIONS

US 7,063,700, 06/2006, Michelson (withdrawn)
(Continued)

*Primary Examiner* — Anu Ramana
(74) *Attorney, Agent, or Firm* — Dorsey & Whitney LLP

(57) ABSTRACT

A spinal joint distraction system is disclosed and may include a driver assembly with a tubular shaft, a pair of implant holder arms, an implant distractor, an internal actuator, and a distractor knob, the system also including a delivery device with a tubular shaft, a receiving assembly, and a pair of forks, where the delivery device is adapted for slidable insertion of the driver assembly, the system also including an implant, a chisel, and an injector. Several embodiments of an implant are disclosed as well a method of placing an implant.

8 Claims, 81 Drawing Sheets

Related U.S. Application Data division of application No. 12/317,682, filed on Dec. 23, 2008, now Pat. No. 8,267,966.

(60) Provisional application No. 61/109,776, filed on Oct. 30, 2008, provisional application No. 61/059,726, filed on Jun. 6, 2008.

(51) Int. Cl.

| | | |
|---|---|---|
| *A61B 17/17* | (2006.01) | |
| *A61B 17/80* | (2006.01) | |
| *A61B 17/064* | (2006.01) | |
| *A61B 17/70* | (2006.01) | |
| *A61B 17/86* | (2006.01) | |
| *A61B 90/00* | (2016.01) | |

(52) U.S. Cl.
CPC ...... *A61B 17/1671* (2013.01); *A61B 17/1735* (2013.01); *A61B 17/1757* (2013.01); *A61B 17/7064* (2013.01); *A61B 17/8004* (2013.01); *A61B 17/0642* (2013.01); *A61B 17/7044* (2013.01); *A61B 17/7059* (2013.01); *A61B 17/8625* (2013.01); *A61B 2017/0256* (2013.01); *A61B 2090/037* (2016.02)

(56) References Cited

U.S. PATENT DOCUMENTS

| | | |
|---|---|---|
| 2,984,241 A | 5/1961 | Carlson |
| 4,479,491 A | 10/1984 | Martin |
| 4,530,355 A | 7/1985 | Griggs |
| 4,604,995 A | 8/1986 | Stephens et al. |
| 4,772,287 A | 9/1988 | Ray et al. |
| 4,877,020 A | 10/1989 | Vich |
| 4,878,915 A | 11/1989 | Brantigan |
| 5,015,247 A | 5/1991 | Michelson |
| 5,026,373 A | 6/1991 | Ray et al. |
| 5,100,405 A | 3/1992 | McLaren |
| 5,135,528 A | 8/1992 | Winston |
| 5,236,460 A | 8/1993 | Barber |
| 5,484,437 A | 1/1996 | Michelson |
| 5,489,307 A | 2/1996 | Kuslich et al. |
| 5,505,732 A | 4/1996 | Michelson |
| 5,527,312 A | 6/1996 | Ray |
| 5,549,679 A | 8/1996 | Kuslich et al. |
| 5,554,191 A | 9/1996 | Lahille et al. |
| 5,571,191 A | 11/1996 | Fitz |
| 5,584,832 A | 12/1996 | Schlapfer et al. |
| 5,593,409 A | 1/1997 | Michelson |
| 5,632,747 A | 5/1997 | Scarborough et al. |
| 5,649,945 A | 7/1997 | Ray et al. |
| 5,653,763 A | 8/1997 | Errico et al. |
| 5,665,122 A | 9/1997 | Kambin |
| 5,674,295 A | 10/1997 | Ray et al. |
| 5,720,748 A | 2/1998 | Kuslich et al. |
| 5,741,253 A | 4/1998 | Michelson |
| 5,772,661 A | 6/1998 | Michelson |
| 5,792,044 A | 8/1998 | Foley et al. |
| 5,797,909 A | 8/1998 | Michelson |
| 5,836,948 A | 11/1998 | Zucherman et al. |
| 5,879,353 A | 3/1999 | Terry |
| 5,885,299 A | 3/1999 | Winslow et al. |
| 5,891,147 A | 4/1999 | Moskovitz |
| 5,895,426 A | 4/1999 | Scarborough et al. |
| 5,899,908 A | 5/1999 | Kuslich et al. |
| 5,928,238 A | 7/1999 | Scarborough et al. |
| 5,953,820 A | 9/1999 | Vasudeva |
| 5,961,522 A | 10/1999 | Mehdizadeh |
| 5,976,146 A | 11/1999 | Ogawa |
| 6,008,433 A | 12/1999 | Stone |
| 6,033,405 A | 3/2000 | Winslow et al. |
| 6,045,580 A | 4/2000 | Scarborough et al. |
| 6,063,088 A | 5/2000 | Winslow |
| RE36,758 E | 6/2000 | Fitz |
| 6,080,155 A | 6/2000 | Michelson |
| 6,090,143 A | 7/2000 | Meriwether et al. |
| 6,096,038 A | 8/2000 | Michelson |
| 6,099,531 A | 8/2000 | Bonutti |
| 6,102,950 A | 8/2000 | Vaccaro |
| 6,113,602 A | 9/2000 | Sand |
| 6,149,650 A | 11/2000 | Michelson |
| RE37,005 E | 12/2000 | Michelson et al. |
| 6,159,245 A | 12/2000 | Meriwether et al. |
| 6,176,882 B1 | 1/2001 | Biedermann et al. |
| 6,179,873 B1 | 1/2001 | Zientek |
| 6,190,388 B1 | 2/2001 | Michelson et al. |
| 6,190,414 B1 | 2/2001 | Young et al. |
| 6,193,757 B1 | 2/2001 | Foley et al. |
| 6,210,412 B1 | 4/2001 | Michelson |
| RE37,161 E | 5/2001 | Michelson et al. |
| 6,224,595 B1 | 5/2001 | Michelson |
| 6,224,607 B1 | 5/2001 | Michelson |
| 6,224,630 B1 | 5/2001 | Bao et al. |
| 6,245,108 B1 | 6/2001 | Biscup |
| 6,248,110 B1 | 6/2001 | Reiley et al. |
| D444,878 S | 7/2001 | Walter |
| D445,188 S | 7/2001 | Walter |
| 6,264,656 B1 | 7/2001 | Michelson |
| 6,267,763 B1 | 7/2001 | Castro |
| 6,270,498 B1 | 8/2001 | Michelson |
| 6,283,966 B1 | 9/2001 | Boufburg |
| 6,315,795 B1 | 11/2001 | Scarborough et al. |
| 6,325,827 B1 | 12/2001 | Lin |
| 6,371,984 B1 | 4/2002 | Van Dyke et al. |
| 6,371,988 B1 | 4/2002 | Pafford et al. |
| 6,402,784 B1 | 6/2002 | Wardlaw |
| 6,423,063 B1 | 7/2002 | Bonutti |
| 6,423,083 B2 | 7/2002 | Reiley et al. |
| 6,425,919 B1 | 7/2002 | Lambrecht |
| 6,436,098 B1 | 8/2002 | Michelson |
| 6,436,142 B1 | 8/2002 | Paes et al. |
| 6,443,988 B2 | 9/2002 | Felt et al. |
| 6,451,023 B1 | 9/2002 | Salazar et al. |
| 6,454,807 B1 | 9/2002 | Jackson |
| 6,478,796 B2 | 11/2002 | Zucherman et al. |
| 6,500,206 B1 | 12/2002 | Bryan |
| 6,514,256 B2 | 2/2003 | Zucherman et al. |
| 6,530,955 B2 | 3/2003 | Boyle et al. |
| 6,558,390 B2 | 5/2003 | Cragg |
| 6,565,574 B2 | 5/2003 | Michelson |
| 6,565,605 B2 | 5/2003 | Fallin et al. |
| 6,569,186 B1 | 5/2003 | Winters et al. |
| 6,575,919 B1 | 6/2003 | Reiley et al. |
| 6,575,979 B1 | 6/2003 | Cragg |
| 6,579,319 B2 | 6/2003 | Goble et al. |
| 6,582,432 B1 | 6/2003 | Michelson |
| 6,607,530 B1 | 8/2003 | Carl et al. |
| 6,610,091 B1 | 8/2003 | Reiley |
| 6,626,905 B1 | 9/2003 | Schmiel et al. |
| 6,632,235 B2 | 10/2003 | Weikel et al. |
| 6,635,060 B2 | 10/2003 | Hanson et al. |
| 6,641,582 B1 | 11/2003 | Hanson et al. |
| 6,648,893 B2 | 11/2003 | Dudasik |
| 6,652,584 B2 | 11/2003 | Michelson |
| 6,663,647 B2 | 12/2003 | Reiley et al. |
| 6,666,866 B2 | 12/2003 | Martz et al. |
| 6,679,886 B2 | 1/2004 | Weikel et al. |
| 6,682,535 B2 | 1/2004 | Hoogland |
| 6,685,742 B1 | 2/2004 | Jackson |
| 6,709,458 B2 | 3/2004 | Michelson |
| 6,712,853 B2 | 3/2004 | Kuslich |
| 6,719,773 B1 | 4/2004 | Boucher et al. |
| 6,723,095 B2 | 4/2004 | Hammerslag |
| 6,733,534 B2 | 5/2004 | Sherman |
| 6,740,093 B2 | 5/2004 | Hochschuler et al. |
| 6,751,875 B2 | 6/2004 | Jones |
| 6,770,074 B2 | 8/2004 | Michelson |
| 6,793,679 B2 | 9/2004 | Michelson |
| 6,805,715 B2 | 10/2004 | Reuter et al. |
| 6,808,537 B2 | 10/2004 | Michelson |
| 6,823,871 B2 | 11/2004 | Schmieding |
| 6,840,941 B2 | 1/2005 | Rogers et al. |
| 6,851,430 B2 | 2/2005 | Tsou |

(56) References Cited

U.S. PATENT DOCUMENTS

| | | |
|---|---|---|
| 6,875,213 B2 | 4/2005 | Michelson |
| 6,899,719 B2 | 5/2005 | Reiley et al. |
| 6,921,403 B2 | 7/2005 | Cragg et al. |
| 6,923,813 B2 | 8/2005 | Phillips et al. |
| 6,958,077 B2 | 10/2005 | Suddaby |
| 6,962,606 B2 | 11/2005 | Michelson |
| 6,964,686 B2 | 11/2005 | Gordon |
| 6,966,930 B2 | 11/2005 | Arnin et al. |
| 6,972,035 B2 | 12/2005 | Michelson |
| 6,974,478 B2 | 12/2005 | Reiley et al. |
| 6,979,333 B2 | 12/2005 | Hammerslag |
| 6,986,772 B2 | 1/2006 | Michelson |
| 7,001,385 B2 | 2/2006 | Bonutti |
| 7,008,453 B1 | 3/2006 | Michelson |
| 7,033,362 B2 | 4/2006 | McGahan et al. |
| 7,033,392 B2 | 4/2006 | Schmiel et al. |
| 7,033,394 B2 | 4/2006 | Michelson |
| 7,066,961 B2 | 6/2006 | Michelson |
| D524,443 S | 7/2006 | Blain |
| 7,083,623 B2 | 8/2006 | Michelson |
| 7,090,698 B2 | 8/2006 | Fallin et al. |
| 7,096,972 B2 | 8/2006 | Orozco, Jr. |
| 7,101,398 B2 | 9/2006 | Dooris et al. |
| 7,115,128 B2 | 10/2006 | Michelson |
| 7,118,598 B2 | 10/2006 | Michelson |
| 7,128,760 B2 | 10/2006 | Michelson |
| 7,156,877 B2 | 1/2007 | Lotz et al. |
| 7,166,110 B2 | 1/2007 | Yundt |
| 7,175,023 B2 | 2/2007 | Martin |
| 7,179,263 B2 | 2/2007 | Zdeblick et al. |
| 7,207,991 B2 | 4/2007 | Michelson |
| D541,940 S | 5/2007 | Blain |
| 7,220,280 B2 | 5/2007 | Kast et al. |
| 7,264,622 B2 | 9/2007 | Michelson |
| 7,273,498 B2 | 9/2007 | Bianchi et al. |
| 7,288,093 B2 | 10/2007 | Michelson |
| 7,291,149 B1 | 11/2007 | Michelson |
| 7,300,440 B2 | 11/2007 | Zdeblick et al. |
| 7,326,211 B2 | 2/2008 | Padget et al. |
| 7,326,214 B2 | 2/2008 | Michelson |
| 7,371,238 B2 | 5/2008 | Soboleski et al. |
| 7,399,303 B2 | 7/2008 | Michelson |
| 7,410,501 B2 | 8/2008 | Michelson |
| 7,431,722 B1 | 10/2008 | Michelson |
| 7,445,636 B2 | 11/2008 | Michelson |
| 7,452,359 B1 | 11/2008 | Michelson |
| 7,452,369 B2 | 11/2008 | Barry |
| 7,465,304 B1 | 12/2008 | Haufe et al. |
| 7,476,226 B2 | 1/2009 | Weikel et al. |
| 7,476,251 B2 | 1/2009 | Zucherman et al. |
| 7,479,160 B2 | 1/2009 | Branch et al. |
| 7,491,205 B1 | 2/2009 | Michelson |
| 7,500,992 B2 | 3/2009 | Li |
| 7,517,358 B2 | 4/2009 | Peterson |
| 7,524,333 B2 | 4/2009 | Lambrecht et al. |
| 7,569,054 B2 | 8/2009 | Michelson |
| 7,569,057 B2 | 8/2009 | Liu et al. |
| 7,580,743 B2 | 8/2009 | Bourlion et al. |
| 7,591,851 B2 | 9/2009 | Winslow et al. |
| 7,601,170 B2 | 10/2009 | Winslow et al. |
| 7,608,077 B2 | 10/2009 | Cragg et al. |
| 7,608,107 B2 | 10/2009 | Michelson |
| 7,615,079 B2 | 11/2009 | Flickinger et al. |
| 7,618,451 B2 | 11/2009 | Berez et al. |
| 7,632,291 B2 | 12/2009 | Stephens et al. |
| 7,641,664 B2 | 1/2010 | Pagano |
| 7,648,523 B2 | 1/2010 | Mirkovic et al. |
| 7,655,027 B2 | 2/2010 | Michelson |
| 7,655,043 B2 | 2/2010 | Peterman et al. |
| 7,662,173 B2 | 2/2010 | Cragg et al. |
| D611,147 S | 3/2010 | Hanson et al. |
| 7,682,378 B2 | 3/2010 | Truckai et al. |
| 7,686,805 B2 | 3/2010 | Michelson |
| 7,686,807 B2 | 3/2010 | Padget et al. |
| 7,699,878 B2 | 4/2010 | Pavlov et al. |
| D615,653 S | 5/2010 | Horton |
| 7,708,761 B2 | 5/2010 | Petersen |
| 7,722,619 B2 | 5/2010 | Michelson |
| D619,719 S | 7/2010 | Pannu |
| 7,763,024 B2 | 7/2010 | Bertagnoli et al. |
| 7,763,050 B2 | 7/2010 | Winslow et al. |
| 7,776,090 B2 | 8/2010 | Winslow et al. |
| D623,748 S | 9/2010 | Horton et al. |
| D623,749 S | 9/2010 | Horton et al. |
| 7,789,898 B2 | 9/2010 | Peterman |
| D627,468 S | 11/2010 | Richter et al. |
| 7,824,431 B2 | 11/2010 | McCormack |
| 7,837,713 B2 | 11/2010 | Peterson |
| 7,846,183 B2 | 12/2010 | Blain |
| 7,846,184 B2 | 12/2010 | Sasso et al. |
| 7,850,733 B2 | 12/2010 | Baynham et al. |
| 7,862,589 B2 | 1/2011 | Thramann |
| 7,867,277 B1 | 1/2011 | Tohmeh |
| D631,967 S | 2/2011 | Horton |
| 7,879,098 B1 | 2/2011 | Simmons, Jr. |
| 7,887,565 B2 | 2/2011 | Michelson |
| 7,892,261 B2 | 2/2011 | Bonutti |
| 7,892,286 B2 | 2/2011 | Michelson |
| 7,896,803 B2 | 3/2011 | Schara et al. |
| 7,896,903 B2 | 3/2011 | Link |
| 7,901,439 B2 | 3/2011 | Horton |
| 7,914,530 B2 | 3/2011 | Michelson |
| 7,918,891 B1 | 4/2011 | Curran et al. |
| 7,922,729 B2 | 4/2011 | Michelson |
| 7,922,766 B2 | 4/2011 | Grob et al. |
| 7,935,136 B2 | 5/2011 | Alamin et al. |
| 7,938,857 B2 | 5/2011 | Krueger et al. |
| 7,988,712 B2 | 8/2011 | Hale et al. |
| 7,988,714 B2 | 8/2011 | Puekert et al. |
| 7,998,174 B2 | 8/2011 | Malandain et al. |
| 8,007,534 B2 | 8/2011 | Michelson |
| 8,029,540 B2 | 10/2011 | Winslow et al. |
| 8,043,334 B2 | 10/2011 | Fisher et al. |
| 8,052,728 B2 | 11/2011 | Hestad |
| 8,062,303 B2 | 11/2011 | Berry et al. |
| 8,066,705 B2 | 11/2011 | Michelson |
| D650,481 S | 12/2011 | Gottlieb et al. |
| 8,097,034 B2 | 1/2012 | Michelson |
| 8,100,944 B2 | 1/2012 | Lauryssen et al. |
| D653,757 S | 2/2012 | Binder |
| 8,114,158 B2 | 2/2012 | Carl et al. |
| 8,118,838 B2 | 2/2012 | Winslow et al. |
| 8,128,660 B2 | 3/2012 | Mitchel et al. |
| 8,133,261 B2 | 3/2012 | Fisher et al. |
| 8,142,503 B2 | 3/2012 | Malone |
| 8,147,553 B2 | 4/2012 | Vresilovic et al. |
| 8,162,981 B2 | 4/2012 | Vestgaarden |
| 8,172,877 B2 | 5/2012 | Winslow et al. |
| 8,177,872 B2 | 5/2012 | Nelson et al. |
| 8,197,513 B2 | 6/2012 | Fisher et al. |
| 8,206,418 B2 | 6/2012 | Triplett et al. |
| 8,267,966 B2 | 9/2012 | McCormack et al. |
| D674,900 S | 1/2013 | Janice et al. |
| 8,348,979 B2 | 1/2013 | McCormack |
| 8,361,152 B2 | 1/2013 | McCormack et al. |
| 8,366,748 B2 | 2/2013 | Kleiner |
| D677,791 S | 3/2013 | Danacioglu et al. |
| 8,394,107 B2 | 3/2013 | Fanger et al. |
| 8,394,129 B2 | 3/2013 | Morgenstern et al. |
| D681,205 S | 4/2013 | Farris et al. |
| 8,425,558 B2 | 4/2013 | McCormack et al. |
| 8,512,347 B2 | 8/2013 | McCormack et al. |
| 8,523,908 B2 | 9/2013 | Malone |
| 8,623,054 B2 | 1/2014 | McCormack et al. |
| 8,668,722 B2 | 3/2014 | Pavlov et al. |
| 8,753,347 B2 | 6/2014 | McCormack et al. |
| 8,764,755 B2 | 7/2014 | Michelson |
| 8,828,062 B2 | 9/2014 | McCormack et al. |
| 8,834,530 B2 | 9/2014 | McCormack |
| 8,845,727 B2 | 9/2014 | Gottlieb et al. |
| 8,870,882 B2 | 10/2014 | Kleiner |
| D723,690 S | 3/2015 | McCormack et al. |
| D723,691 S | 3/2015 | McCormack et al. |
| 8,998,905 B2 | 4/2015 | Marik et al. |

(56) References Cited

U.S. PATENT DOCUMENTS

| | | |
|---|---|---|
| 9,011,492 B2 * | 4/2015 | McCormack .......... A61B 17/025 606/247 |
| D732,667 S | 6/2015 | McCormack et al. |
| D745,156 S | 12/2015 | McCormack et al. |
| 9,211,198 B2 | 12/2015 | Michelson |
| 9,220,608 B2 | 12/2015 | McKay |
| D750,249 S | 2/2016 | Grimberg et al. |
| 9,271,765 B2 | 3/2016 | Blain |
| 9,333,086 B2 | 5/2016 | McCormack et al. |
| 9,381,049 B2 | 7/2016 | McCormack et al. |
| 9,427,264 B2 | 8/2016 | Kleiner et al. |
| 9,504,583 B2 | 11/2016 | Blain et al. |
| 9,717,403 B2 | 8/2017 | Kleiner et al. |
| 2001/0004710 A1 | 6/2001 | Felt et al. |
| 2001/0047208 A1 | 11/2001 | Michelson et al. |
| 2002/0026195 A1 | 2/2002 | Layne et al. |
| 2002/0107519 A1 | 8/2002 | Dixon et al. |
| 2002/0143343 A1 | 10/2002 | Castro |
| 2002/0147496 A1 | 10/2002 | Belef et al. |
| 2002/0147497 A1 | 10/2002 | Belef et al. |
| 2002/0165612 A1 | 11/2002 | Gerber et al. |
| 2002/0169471 A1 | 11/2002 | Ferdinand |
| 2003/0023312 A1 | 1/2003 | Thalgott et al. |
| 2003/0028251 A1 | 2/2003 | Mathews |
| 2003/0032962 A1 | 2/2003 | McGahan et al. |
| 2003/0033017 A1 | 2/2003 | Lotz et al. |
| 2003/0105526 A1 | 6/2003 | Bryant et al. |
| 2003/0109928 A1 | 6/2003 | Pasquet et al. |
| 2003/0139816 A1 | 7/2003 | Michelson |
| 2003/0144737 A1 | 7/2003 | Sherman |
| 2003/0158553 A1 | 8/2003 | Michelson |
| 2003/0225416 A1 | 12/2003 | Bonvallet et al. |
| 2004/0059337 A1 | 3/2004 | Hanson et al. |
| 2004/0073217 A1 | 4/2004 | Michelson |
| 2004/0087948 A1 | 5/2004 | Suddaby |
| 2004/0087956 A1 | 5/2004 | Weikel et al. |
| 2004/0106999 A1 | 6/2004 | Mathews |
| 2004/0133277 A1 | 7/2004 | Michelson |
| 2004/0133280 A1 | 7/2004 | Trieu |
| 2004/0162562 A1 | 8/2004 | Martz |
| 2004/0215344 A1 | 10/2004 | Hochshculer et al. |
| 2005/0010294 A1 | 1/2005 | Michelson |
| 2005/0015149 A1 | 1/2005 | Michelson |
| 2005/0027358 A1 | 2/2005 | Suddaby |
| 2005/0033432 A1 | 2/2005 | Gordon et al. |
| 2005/0049705 A1 | 3/2005 | Hale et al. |
| 2005/0055096 A1 | 3/2005 | Serhan et al. |
| 2005/0065518 A1 | 3/2005 | Michelson |
| 2005/0065519 A1 | 3/2005 | Michelson |
| 2005/0065608 A1 | 3/2005 | Michelson |
| 2005/0065609 A1 | 3/2005 | Wardlaw |
| 2005/0080422 A1 | 4/2005 | Otte et al. |
| 2005/0090829 A1 | 4/2005 | Martz et al. |
| 2005/0090901 A1 | 4/2005 | Studer |
| 2005/0119680 A1 | 6/2005 | Dykes |
| 2005/0124993 A1 | 6/2005 | Chappuis |
| 2005/0159650 A1 | 7/2005 | Raymond et al. |
| 2005/0159746 A1 | 7/2005 | Grob et al. |
| 2005/0177240 A1 | 8/2005 | Blain |
| 2005/0182417 A1 | 8/2005 | Pagano |
| 2005/0216018 A1 | 9/2005 | Sennett |
| 2005/0240188 A1 | 10/2005 | Chow et al. |
| 2005/0251146 A1 | 11/2005 | Martz et al. |
| 2005/0251257 A1 | 11/2005 | Mitchell et al. |
| 2005/0267480 A1 | 12/2005 | Suddaby |
| 2006/0004367 A1 | 1/2006 | Alamin et al. |
| 2006/0015184 A1 | 1/2006 | Winterbottom et al. |
| 2006/0036243 A1 | 2/2006 | Sasso et al. |
| 2006/0036247 A1 | 2/2006 | Michelson |
| 2006/0036323 A1 | 2/2006 | Carl et al. |
| 2006/0041311 A1 | 2/2006 | McLeer |
| 2006/0058793 A1 | 3/2006 | Michelson |
| 2006/0058878 A1 | 3/2006 | Michelson |
| 2006/0069442 A1 | 3/2006 | Michelson |
| 2006/0079905 A1 | 4/2006 | Beyar et al. |
| 2006/0079962 A1 | 4/2006 | Michelson |
| 2006/0085068 A1 | 4/2006 | Barry et al. |
| 2006/0085074 A1 | 4/2006 | Raiszadeh |
| 2006/0095028 A1 | 5/2006 | Bleich |
| 2006/0095036 A1 | 5/2006 | Hammerslag |
| 2006/0111779 A1 | 5/2006 | Peterson |
| 2006/0111780 A1 | 5/2006 | Petersen |
| 2006/0111781 A1 | 5/2006 | Petersen |
| 2006/0142762 A1 | 6/2006 | Michelson |
| 2006/0149289 A1 | 7/2006 | Winslow et al. |
| 2006/0184172 A1 | 8/2006 | Michelson |
| 2006/0190081 A1 | 8/2006 | Kraus et al. |
| 2006/0195109 A1 | 8/2006 | McGahan et al. |
| 2006/0200137 A1 | 9/2006 | Soboleski et al. |
| 2006/0200138 A1 | 9/2006 | Michelson |
| 2006/0200139 A1 | 9/2006 | Michelson |
| 2006/0206118 A1 | 9/2006 | Kim et al. |
| 2006/0217812 A1 | 9/2006 | Lambrecht et al. |
| 2006/0235391 A1 | 10/2006 | Sutterlin, III |
| 2006/0241597 A1 | 10/2006 | Mitchell et al. |
| 2006/0241626 A1 | 10/2006 | McGahan et al. |
| 2006/0241758 A1 | 10/2006 | Peterman et al. |
| 2006/0247632 A1 | 11/2006 | Winslow et al. |
| 2006/0247633 A1 | 11/2006 | Winslow et al. |
| 2006/0247650 A1 | 11/2006 | Yerby et al. |
| 2006/0259142 A1 | 11/2006 | Dooris et al. |
| 2006/0271195 A1 | 11/2006 | Thramann |
| 2006/0276790 A1 | 12/2006 | Dawson et al. |
| 2006/0276801 A1 | 12/2006 | Yerby et al. |
| 2006/0276897 A1 | 12/2006 | Winslow et al. |
| 2006/0293663 A1 | 12/2006 | Walkenhorst et al. |
| 2007/0016195 A1 | 1/2007 | Winslow et al. |
| 2007/0016196 A1 | 1/2007 | Winslow et al. |
| 2007/0016218 A1 | 1/2007 | Winslow et al. |
| 2007/0032871 A1 | 2/2007 | Michelson |
| 2007/0043362 A1 | 2/2007 | Malandain et al. |
| 2007/0050031 A1 | 3/2007 | Khosrowshahi |
| 2007/0055245 A1 | 3/2007 | Sasso et al. |
| 2007/0055263 A1 | 3/2007 | Way et al. |
| 2007/0073402 A1 | 3/2007 | Vresilovic et al. |
| 2007/0083265 A1 | 4/2007 | Malone |
| 2007/0123863 A1 | 5/2007 | Winslow et al. |
| 2007/0123888 A1 | 5/2007 | Bleich et al. |
| 2007/0135814 A1 | 6/2007 | Farris |
| 2007/0135921 A1 | 6/2007 | Park |
| 2007/0149976 A1 | 6/2007 | Hale et al. |
| 2007/0149983 A1 | 6/2007 | Link |
| 2007/0150061 A1 | 6/2007 | Trieu |
| 2007/0161991 A1 | 7/2007 | Altarac et al. |
| 2007/0179617 A1 | 8/2007 | Brown et al. |
| 2007/0179619 A1 | 8/2007 | Grob et al. |
| 2007/0225721 A1 | 9/2007 | Thelen et al. |
| 2007/0225812 A1 | 9/2007 | Gill |
| 2007/0244483 A9 | 10/2007 | Winslow et al. |
| 2007/0276491 A1 | 11/2007 | Ahrens |
| 2007/0282441 A1 | 12/2007 | Stream et al. |
| 2007/0288014 A1 | 12/2007 | Shadduck et al. |
| 2007/0299451 A1 | 12/2007 | Tulkis |
| 2008/0015581 A1 | 1/2008 | Eckman et al. |
| 2008/0021457 A1 | 1/2008 | Anderson et al. |
| 2008/0021464 A1 | 1/2008 | Morin et al. |
| 2008/0058954 A1 | 3/2008 | Trieu |
| 2008/0065219 A1 | 3/2008 | Dye |
| 2008/0097436 A1 | 4/2008 | Culbert et al. |
| 2008/0108996 A1 | 5/2008 | Padget et al. |
| 2008/0140207 A1 | 6/2008 | Olmos et al. |
| 2008/0161810 A1 | 7/2008 | Melkent |
| 2008/0161929 A1 | 7/2008 | McCormack et al. |
| 2008/0167657 A1 | 7/2008 | Greenhaigh |
| 2008/0177311 A1 | 7/2008 | Winslow et al. |
| 2008/0208341 A1 | 8/2008 | McCormack et al. |
| 2008/0216846 A1 | 9/2008 | Levin |
| 2008/0234677 A1 | 9/2008 | Dahners et al. |
| 2008/0234758 A1 | 9/2008 | Fisher et al. |
| 2008/0255564 A1 | 10/2008 | Michelson |
| 2008/0255618 A1 | 10/2008 | Fisher et al. |
| 2008/0255622 A1 | 10/2008 | Mickiewicz et al. |
| 2008/0255666 A1 | 10/2008 | Fisher et al. |
| 2008/0255667 A1 | 10/2008 | Horton |

(56) References Cited

U.S. PATENT DOCUMENTS

| | | |
|---|---|---|
| 2008/0287955 A1 | 11/2008 | Michelson |
| 2008/0306537 A1 | 12/2008 | Culbert |
| 2008/0312744 A1 | 12/2008 | Vresilovic et al. |
| 2009/0131986 A1 | 5/2009 | Lee et al. |
| 2009/0138053 A1 | 5/2009 | Assell et al. |
| 2009/0177205 A1 | 7/2009 | McCormack et al. |
| 2009/0177237 A1 | 7/2009 | Zucherman et al. |
| 2009/0234397 A1 | 9/2009 | Petersen |
| 2009/0248076 A1 | 10/2009 | Reynolds et al. |
| 2009/0263461 A1 | 10/2009 | McKay |
| 2009/0270929 A1 | 10/2009 | Suddaby et al. |
| 2009/0275994 A1 | 11/2009 | Phan et al. |
| 2009/0306671 A1 | 12/2009 | McCormack et al. |
| 2009/0312763 A1 | 12/2009 | McCormack et al. |
| 2010/0069912 A1 | 3/2010 | McCormack et al. |
| 2010/0086185 A1 | 4/2010 | Weiss |
| 2010/0093829 A1 | 4/2010 | Gorman |
| 2010/0114318 A1 | 5/2010 | Gittings et al. |
| 2010/0145391 A1 | 6/2010 | Kleiner |
| 2010/0191241 A1 | 7/2010 | McCormack et al. |
| 2011/0004247 A1 | 1/2011 | Lechmann et al. |
| 2011/0022089 A1 | 1/2011 | Assell et al. |
| 2011/0054613 A1 | 3/2011 | Hansen |
| 2011/0077686 A1 | 3/2011 | Mishra et al. |
| 2011/0082548 A1 | 4/2011 | Assell et al. |
| 2011/0144755 A1 | 6/2011 | Baynham et al. |
| 2011/0190821 A1 | 8/2011 | Chin et al. |
| 2011/0245930 A1 | 10/2011 | Alley et al. |
| 2011/0295327 A1 | 12/2011 | Moskowitz et al. |
| 2011/0307061 A1 | 12/2011 | Assell et al. |
| 2012/0010659 A1 | 1/2012 | Angert et al. |
| 2012/0010662 A1 | 1/2012 | O'Neil et al. |
| 2012/0010669 A1 | 1/2012 | O'Neil et al. |
| 2012/0065613 A1 | 3/2012 | Pepper et al. |
| 2012/0143334 A1 | 6/2012 | Boyce et al. |
| 2012/0215259 A1 | 8/2012 | Cannestra |
| 2012/0265250 A1 | 10/2012 | Ali |
| 2012/0283776 A1 | 11/2012 | Mishra |
| 2012/0323242 A1 | 12/2012 | Tsuang et al. |
| 2013/0006364 A1 | 1/2013 | McCormack et al. |
| 2013/0012994 A1 | 1/2013 | McCormack et al. |
| 2013/0013070 A1 | 1/2013 | McCormack et al. |
| 2013/0018474 A1 | 1/2013 | McCormack et al. |
| 2013/0023995 A1 | 1/2013 | McCormack et al. |
| 2013/0023996 A1 | 1/2013 | McCormack et al. |
| 2013/0030440 A1 | 1/2013 | McCormack et al. |
| 2013/0030532 A1 | 1/2013 | McCormack et al. |
| 2013/0110168 A1 | 5/2013 | McCormack et al. |
| 2013/0110243 A1 | 5/2013 | Patterson et al. |
| 2013/0123922 A1 | 5/2013 | McCormack et al. |
| 2013/0144389 A1 | 6/2013 | Bonutti |
| 2013/0226239 A1 | 8/2013 | Altarac et al. |
| 2013/0253649 A1 | 9/2013 | Davis |
| 2013/0274763 A1 | 10/2013 | Drapeau et al. |
| 2013/0310839 A1 | 11/2013 | McCormack et al. |
| 2013/0310878 A1 | 11/2013 | McCormack et al. |
| 2013/0310943 A1 | 11/2013 | McCormack et al. |
| 2013/0317548 A1 | 11/2013 | Malone |
| 2013/0338720 A1 | 12/2013 | Kleiner |
| 2014/0025113 A1 | 1/2014 | McCormack et al. |
| 2014/0100657 A1 | 4/2014 | McCormack et al. |
| 2014/0379087 A1 | 12/2014 | McCormack |
| 2015/0297357 A1 | 10/2015 | McCormack et al. |
| 2017/0027713 A1 | 2/2017 | Kleiner |
| 2017/0189199 A1 | 7/2017 | Maier et al. |
| 2017/0216044 A1 | 8/2017 | McCormack |

FOREIGN PATENT DOCUMENTS

| | | |
|---|---|---|
| WO | 9641582 A1 | 12/1996 |
| WO | 99/49818 A1 | 10/1999 |
| WO | 00/035388 A1 | 6/2000 |
| WO | 00/53126 A1 | 9/2000 |
| WO | 0053126 A1 | 9/2000 |
| WO | 01/01895 A1 | 1/2001 |
| WO | 02/34120 A2 | 5/2002 |
| WO | 02/38062 A2 | 5/2002 |
| WO | 0234120 A2 | 5/2002 |
| WO | 02/076335 A2 | 10/2002 |
| WO | 2006058221 A2 | 6/2006 |
| WO | 2006130791 A2 | 12/2006 |
| WO | 2007120903 A2 | 10/2007 |
| WO | 2008083349 A1 | 7/2008 |
| WO | 2008153732 A1 | 12/2008 |
| WO | 2009089367 A2 | 7/2009 |
| WO | 2009148619 A2 | 12/2009 |
| WO | 2010030994 A2 | 3/2010 |
| WO | 2010074714 A2 | 7/2010 |
| WO | 2016049784 A1 | 4/2016 |

OTHER PUBLICATIONS

Stein et al., "Percuraneous Facet Joint Fusion: Preliminary Experience," Journal of Vascular and Interventional Radiology, Jan.-Feb. 1993, pp. 69-74, vol. 4, No. 1.

Goel, Atul, "Facetal distraction as treatment for single- and multi-level cervical spondylotic radiculopathy and myelopathy: a preliminary report", J Neurosurg Spine, Jun. 2011, pp. 689-696.

International Search Report and Written Opinion, International patent application No. PCT/US2009/003423, Dec. 14, 2009, pp. 1-16.

Partial International Search Report, International patent application No. PCT/US2009/003423, dated Sep. 14, 2009, pp. 1-3.

Press Release, Interventional Spine, Inc., Interventional Spine, Inc. Introduces the PERPOS Fusion Facet Prep Kit, Oct. 14, 2008, 1 Page.

Press Release, minSURG Corp., Orthopedic Development Corporation's TruFUSE Procedure Tops 1,750 Patients in First Year, Sep. 24, 2007, 1 Page.

Press Release, Interventional Spine, Inc., FDA Grants Conditional Approval to Interventional Spine's PercuDyn System IDE Application, Jul. 1, 2008, 1 Page.

* cited by examiner

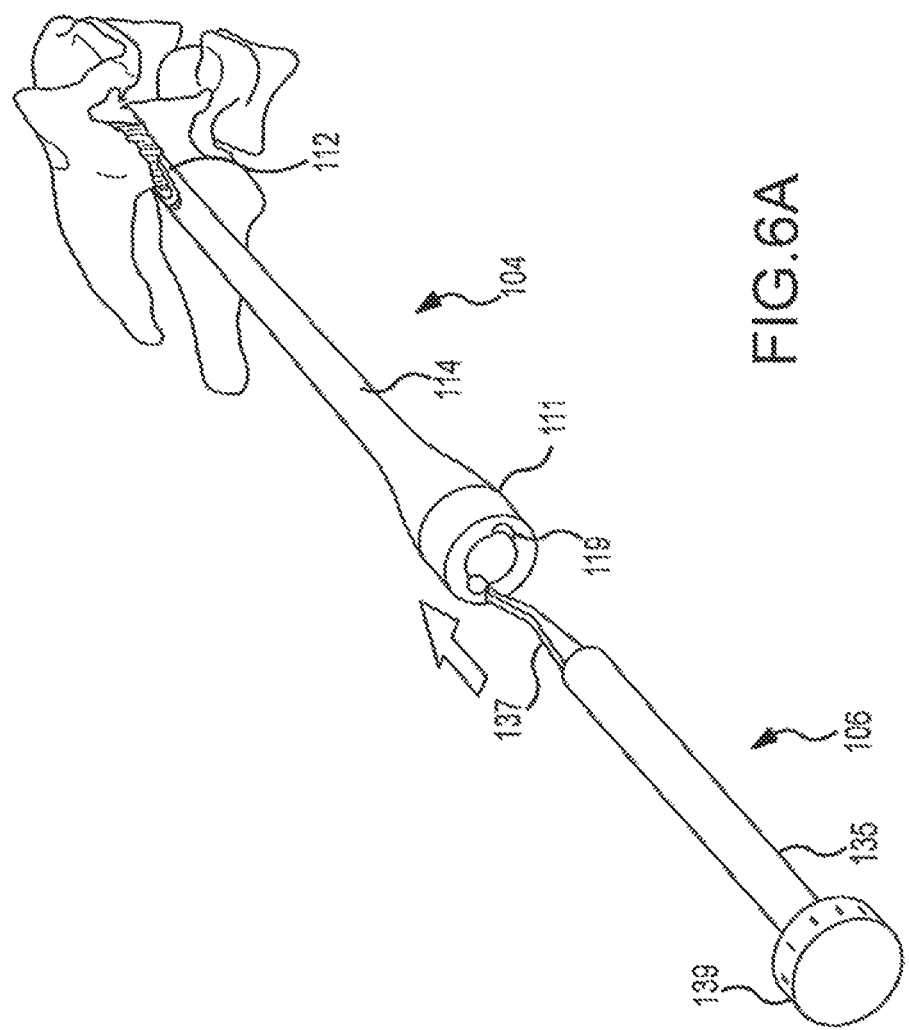

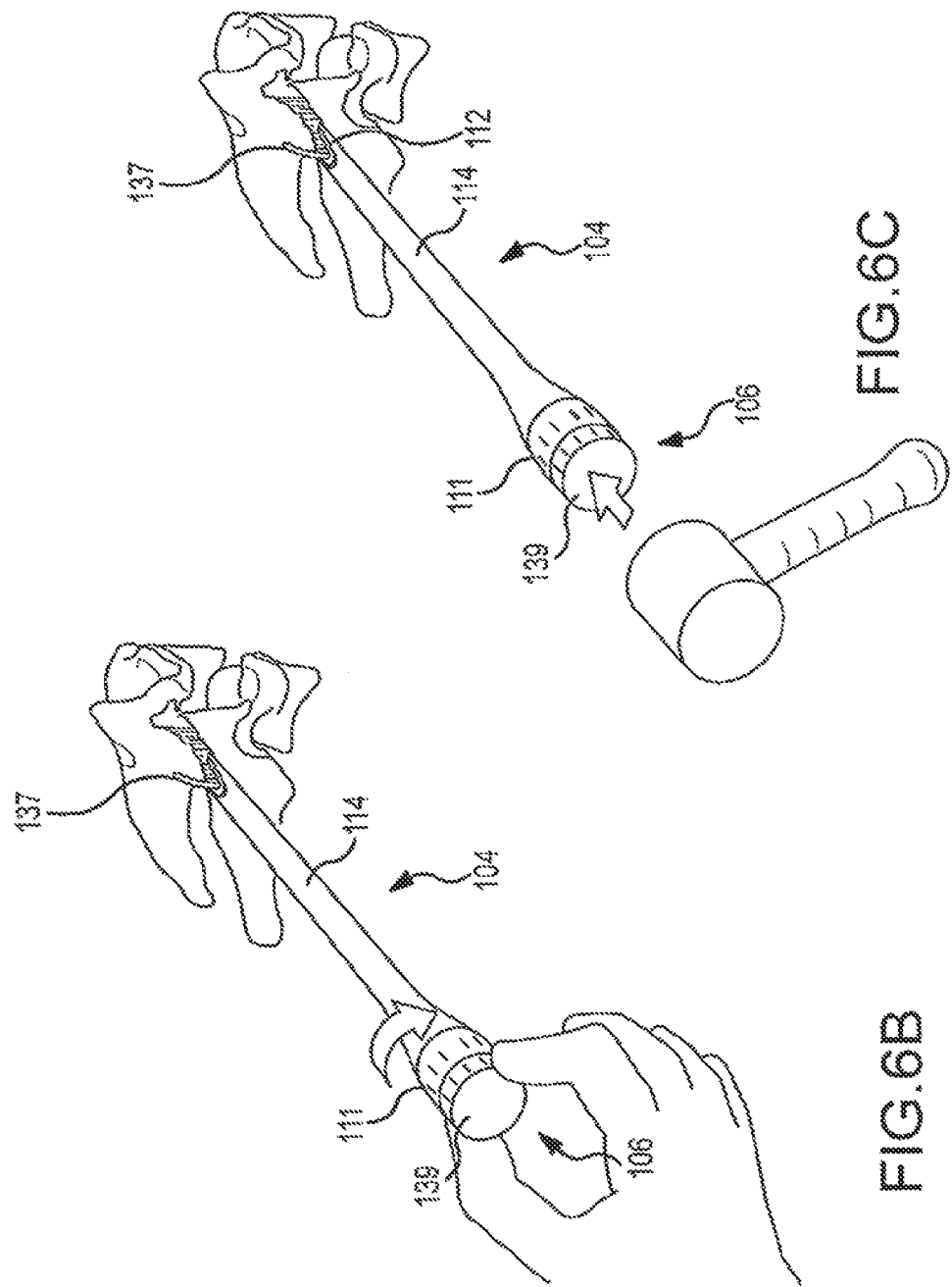

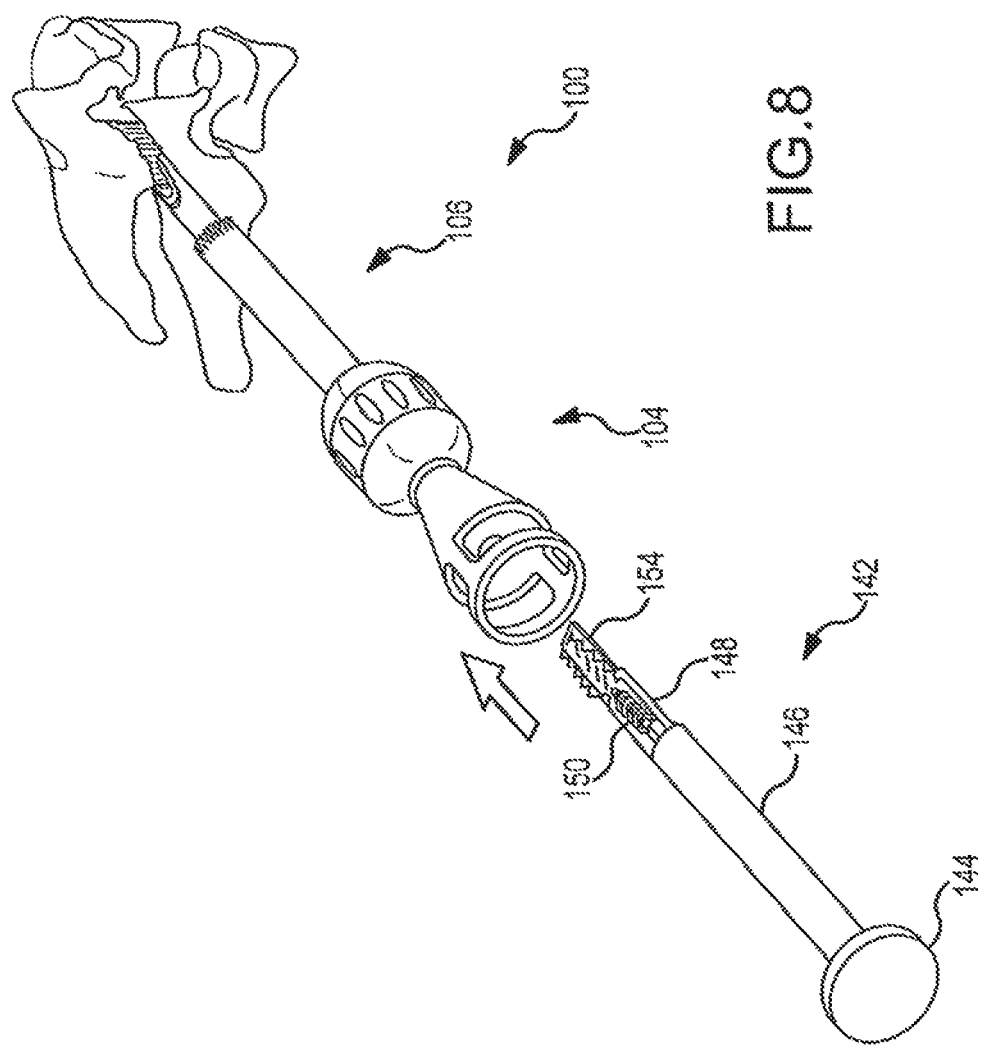

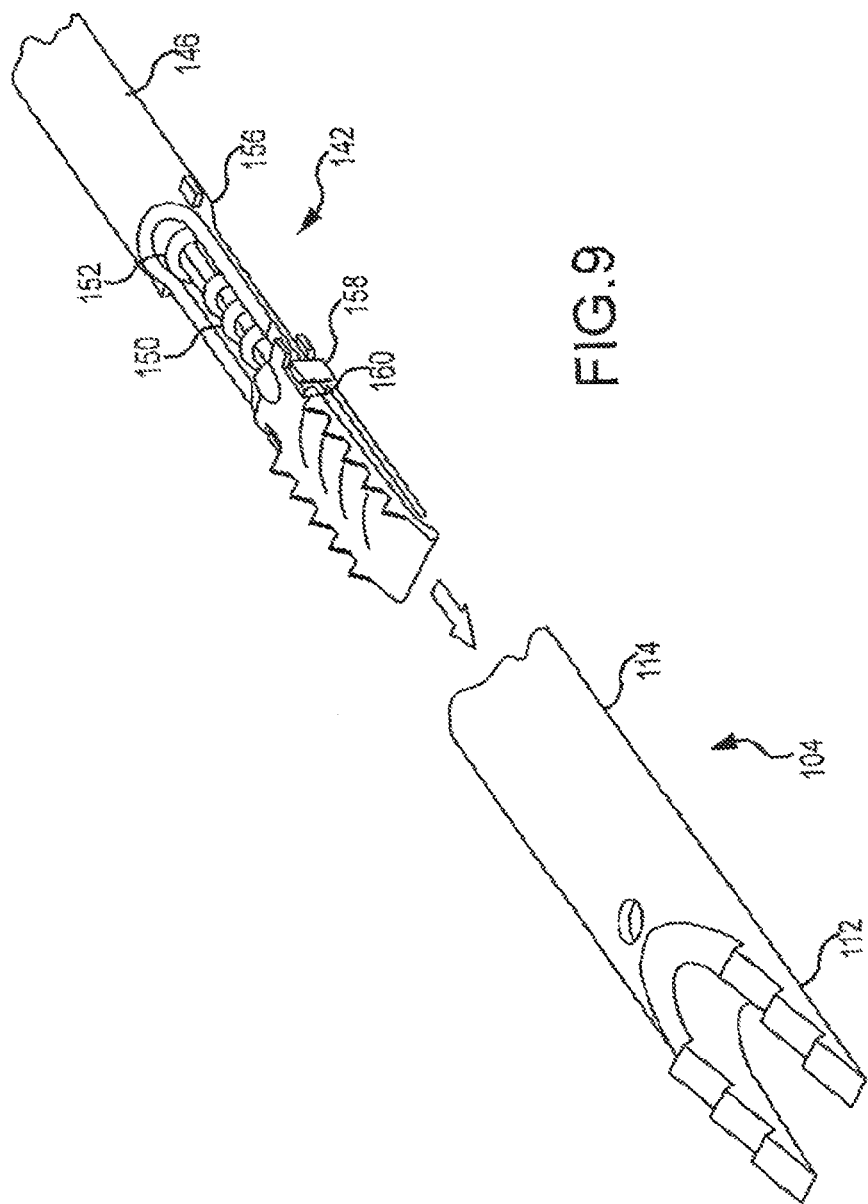

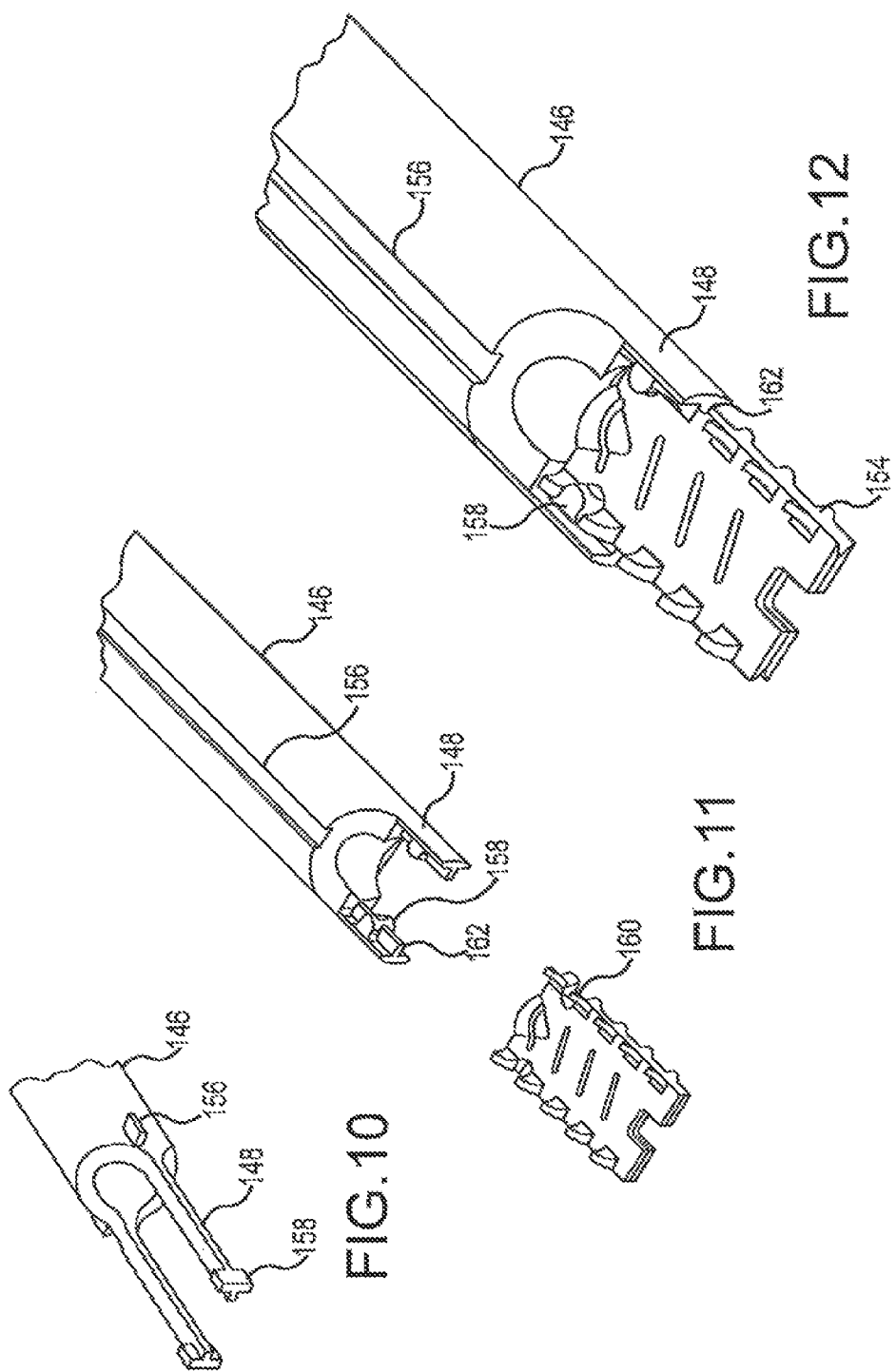

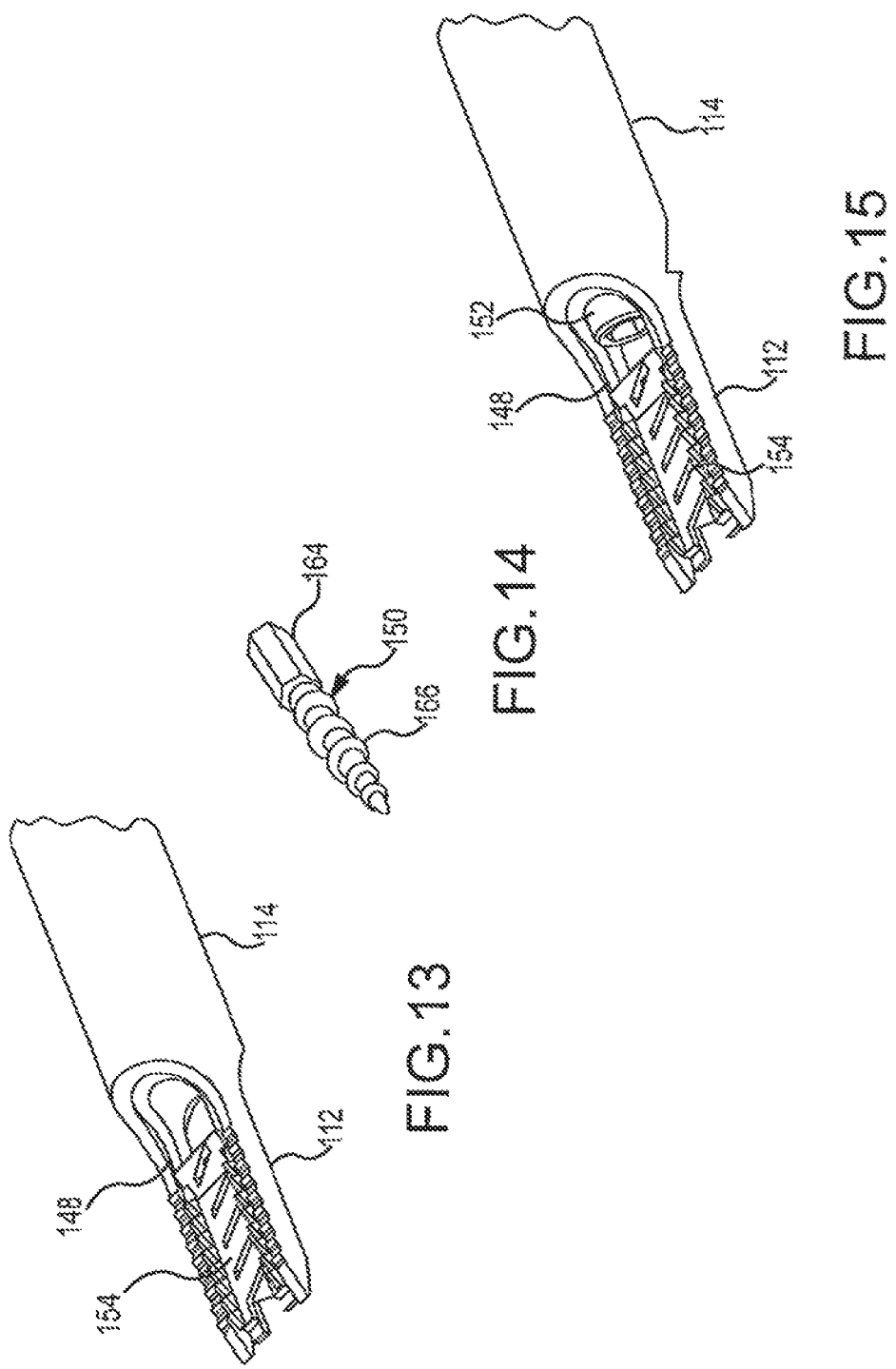

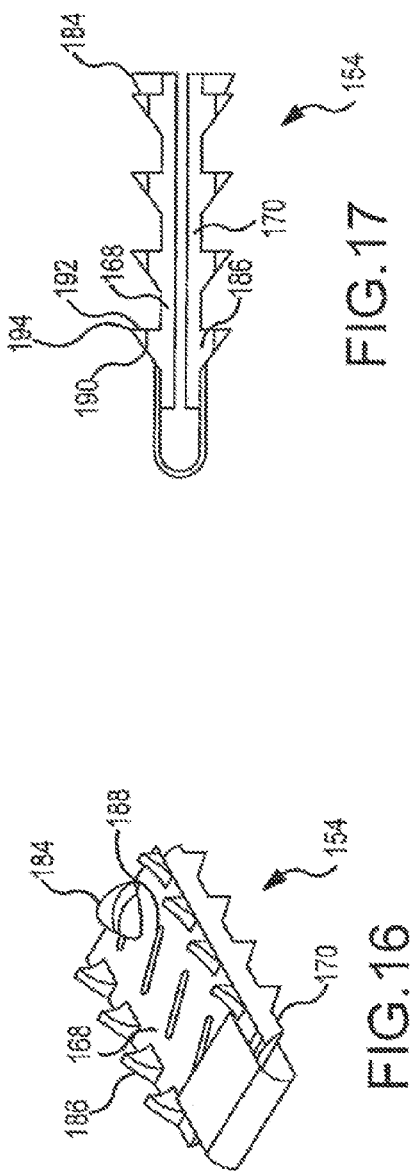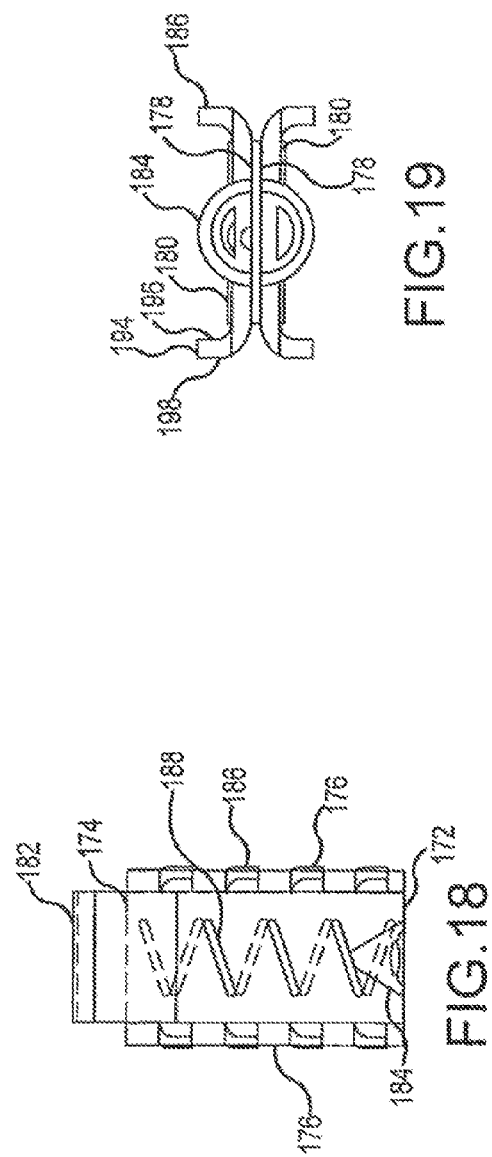

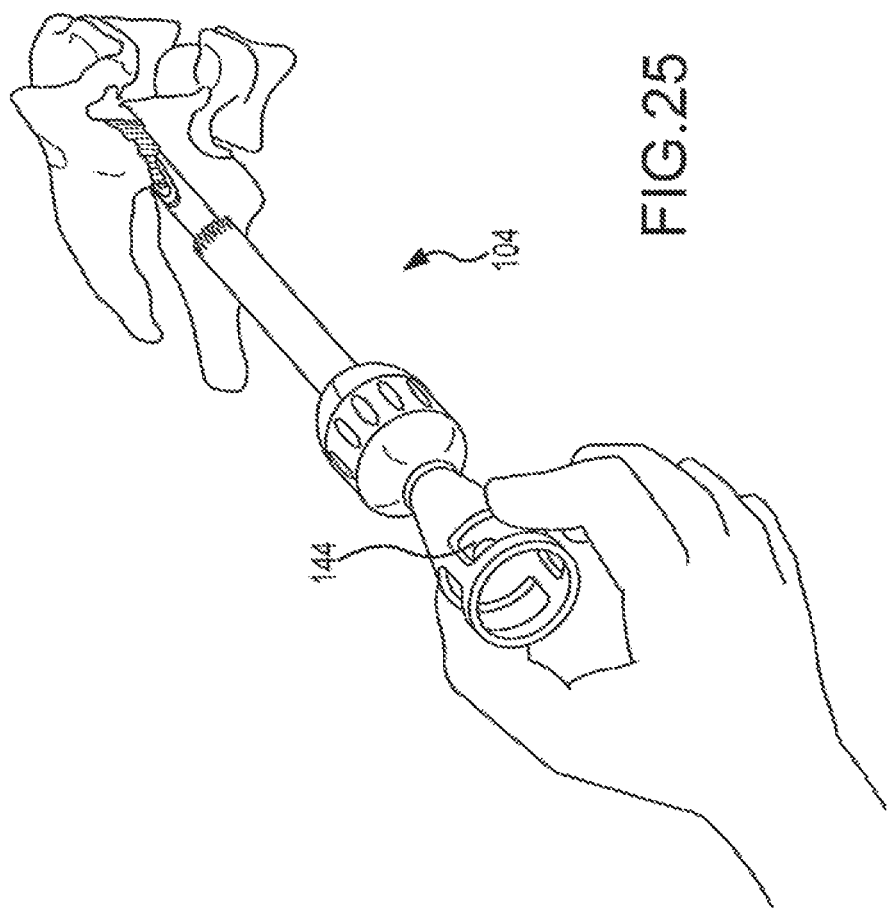

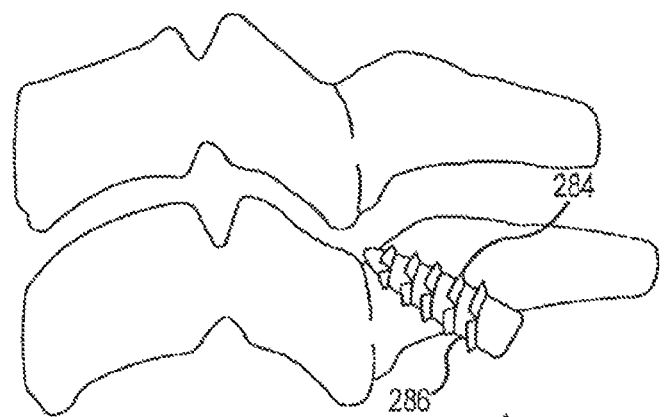
FIG.39A
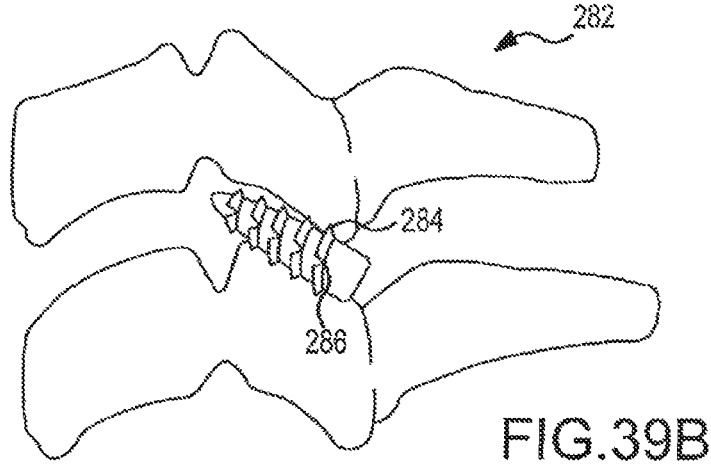
FIG.39B
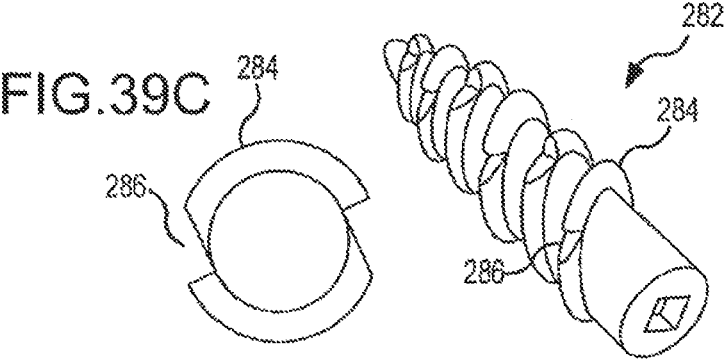
FIG.39C
FIG.39D

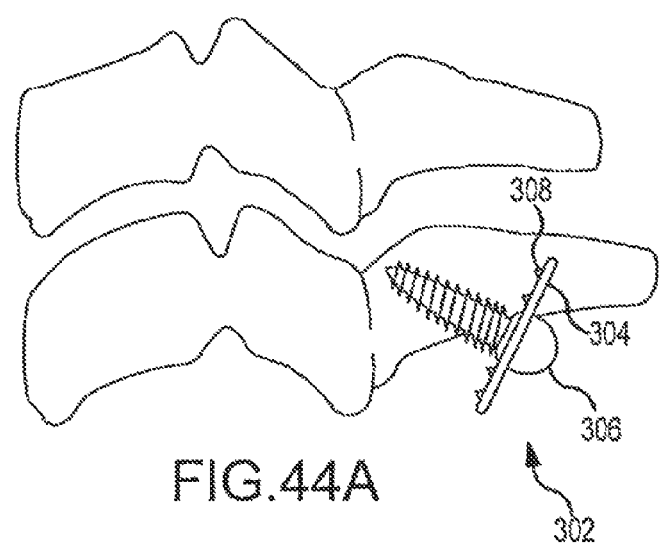
FIG.44A
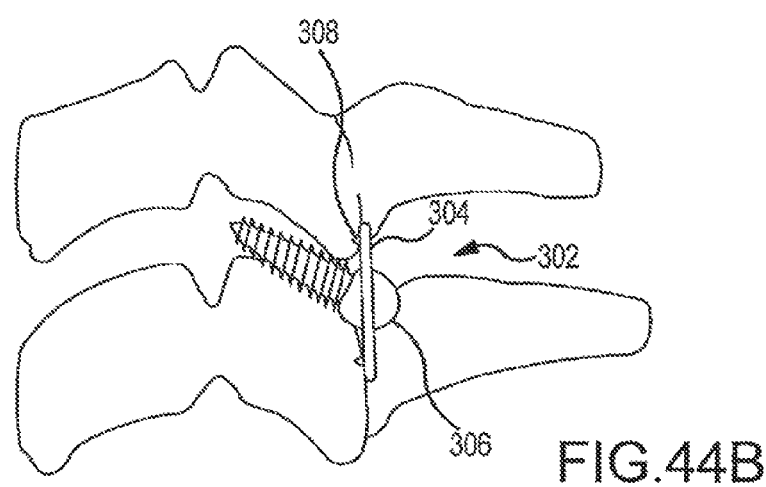
FIG.44B
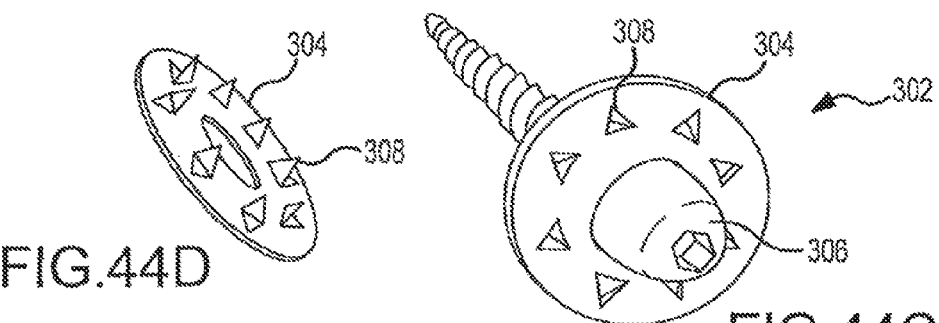
FIG.44D
FIG.44C

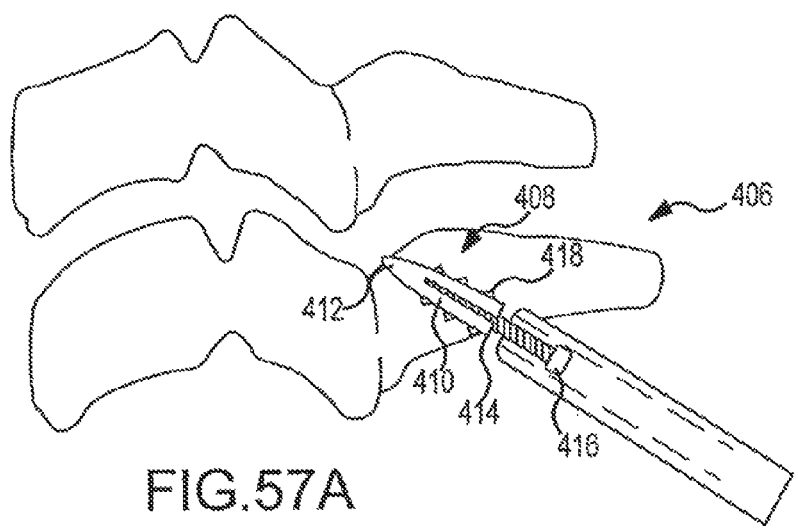
FIG.57A
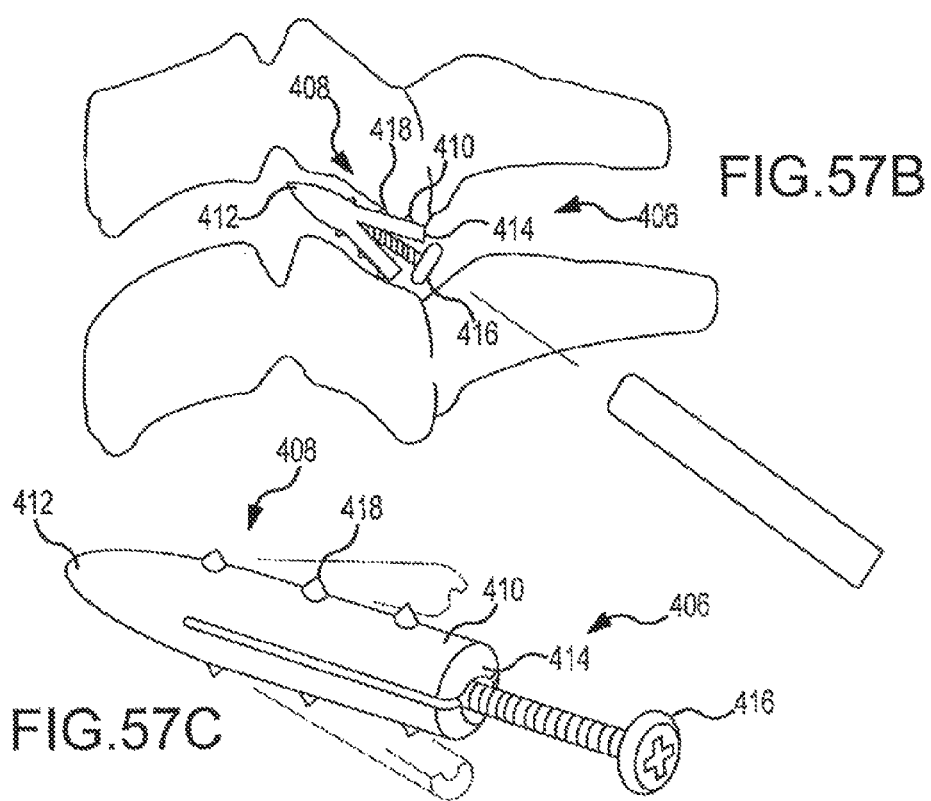
FIG.57B
FIG.57C

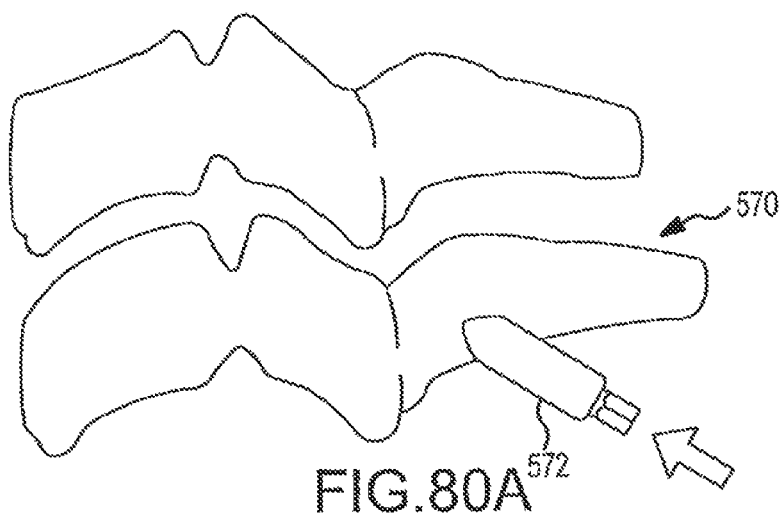
FIG.80A
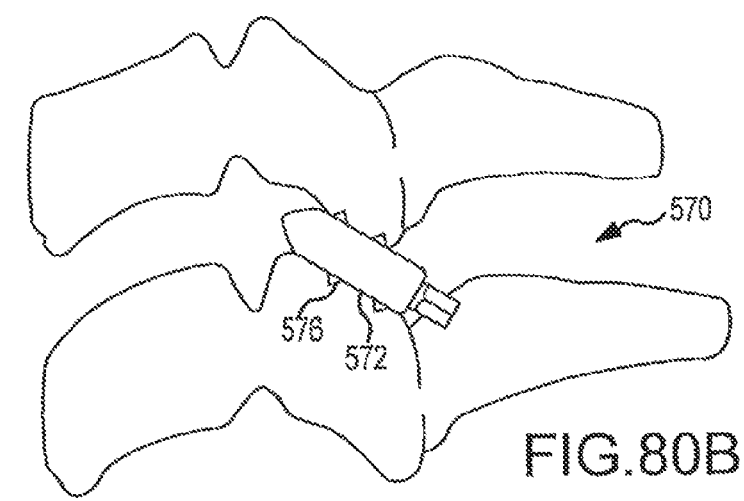
FIG.80B
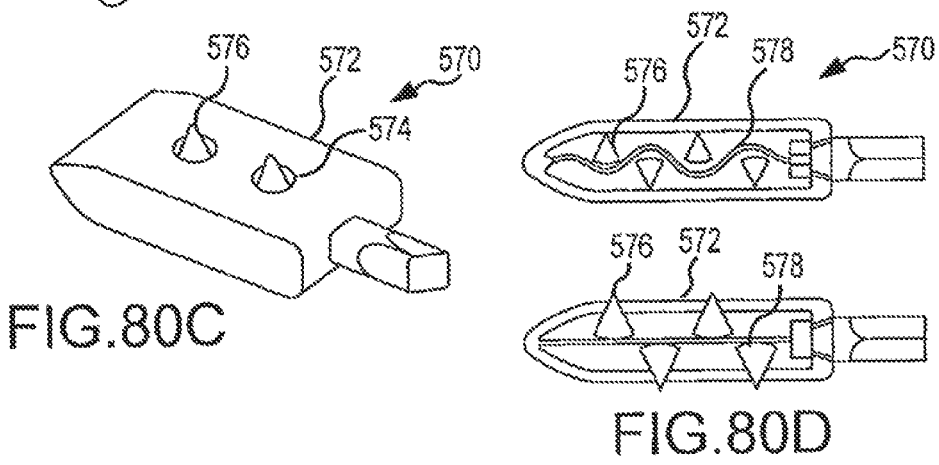
FIG.80C
FIG.80D

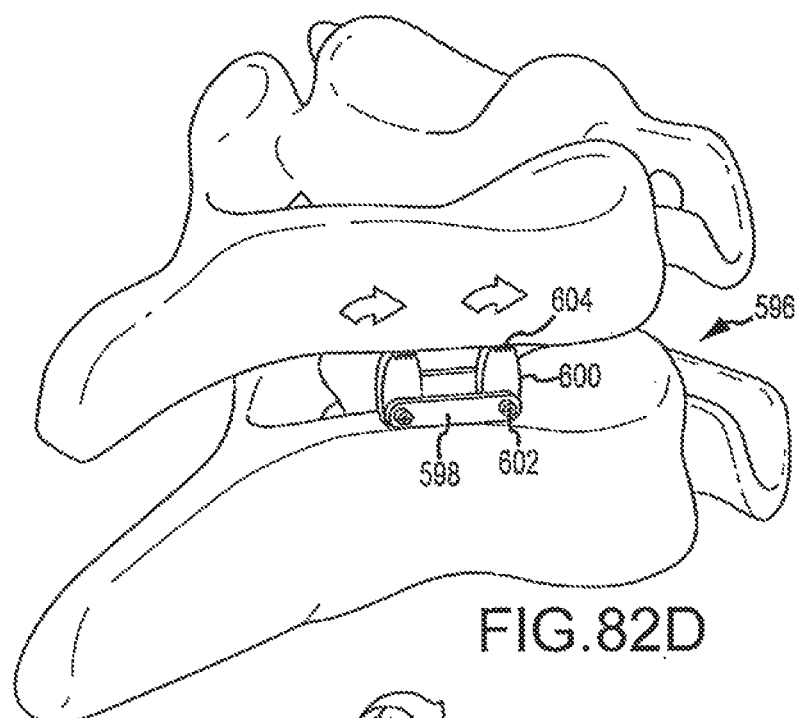
FIG.82D
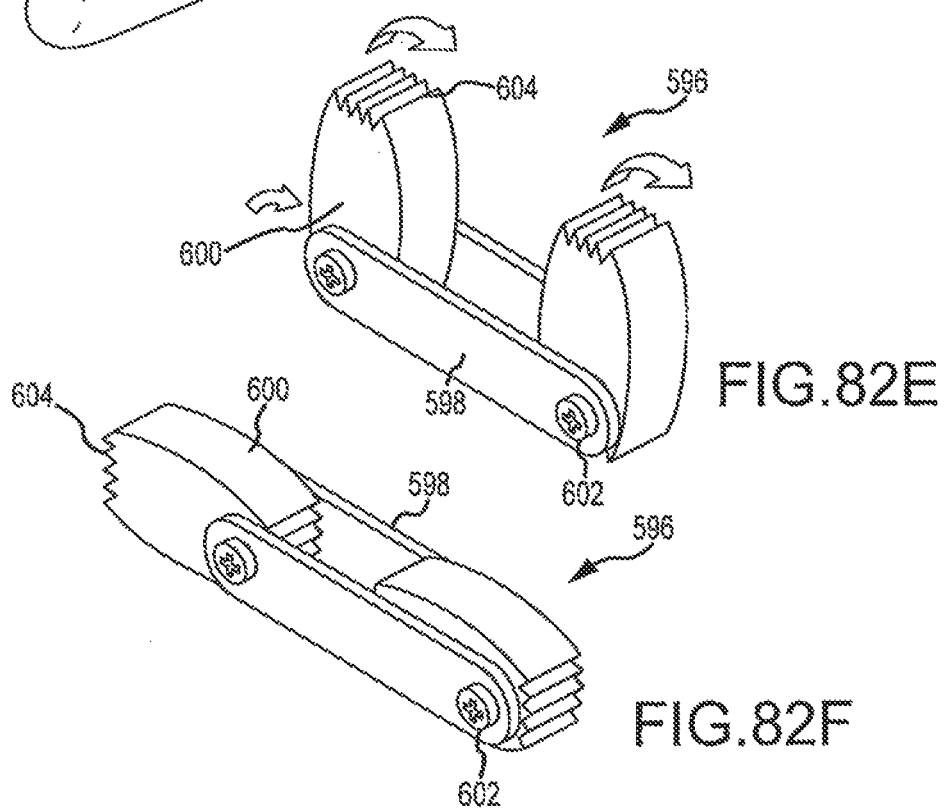
FIG.82E
FIG.82F

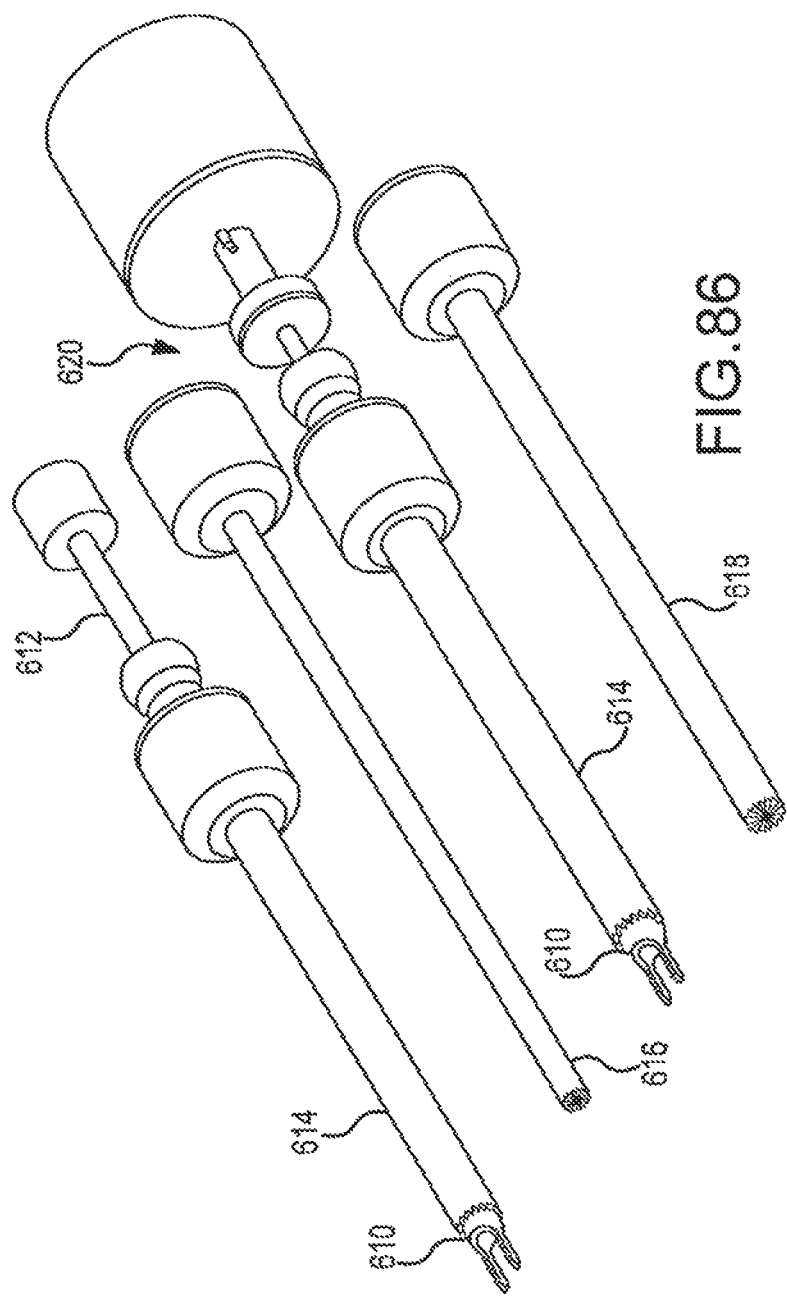

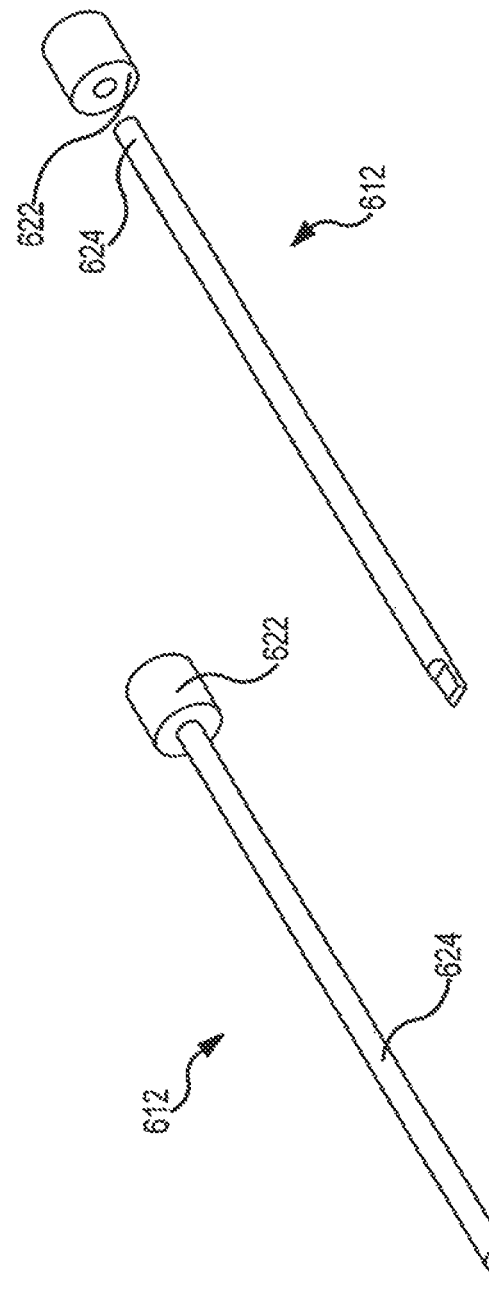

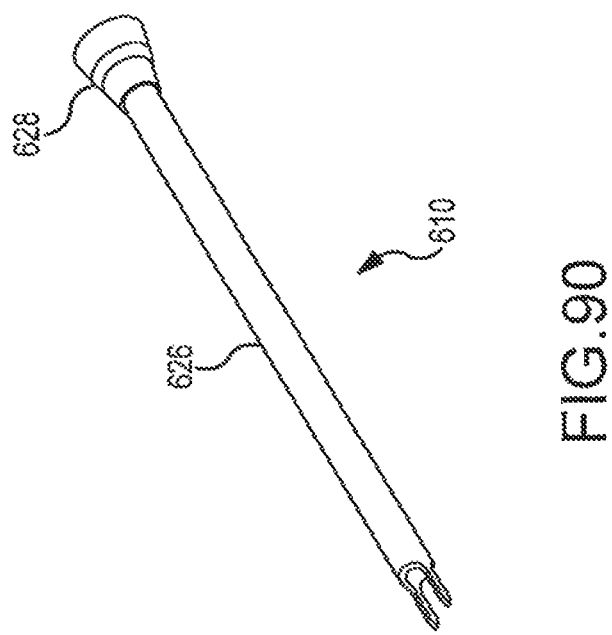
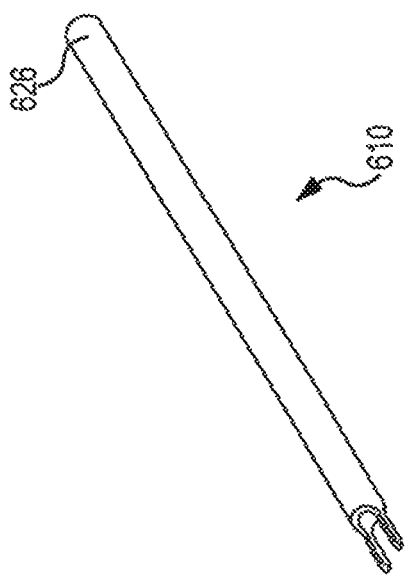

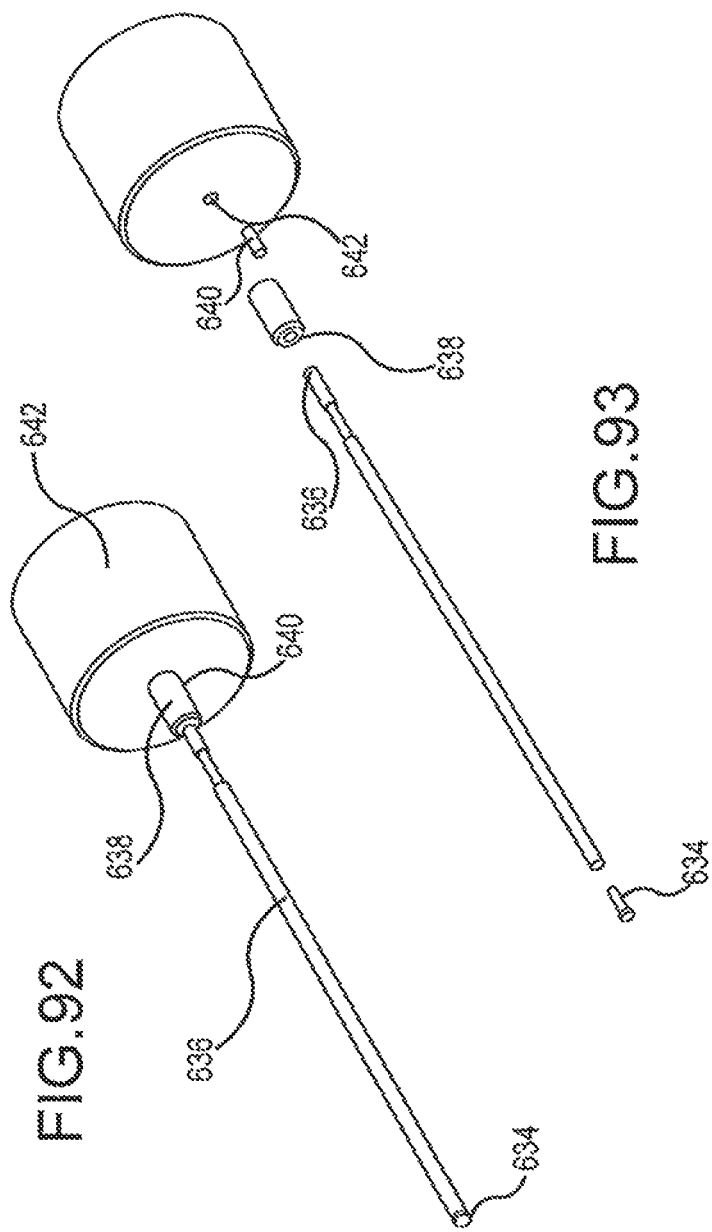

FACET JOINT IMPLANTS AND DELIVERY TOOLS

CROSS-REFERENCE TO RELATED APPLICATION(S)

This application is a continuation application of Ser. No. 13/614,281, filed Sep. 13, 2012, entitled "FACET JOINT IMPLANTS AND DELIVERY TOOLS," now U.S. Pat. No. 9,011,492, which is a divisional application of Ser. No. 12/317,682, filed Dec. 23, 2008, entitled "FACET JOINT IMPLANTS AND DELIVERY TOOLS," now U.S. Pat. No. 8,267,966, which claims priority to U.S. Provisional Patent Application No. 61/109,776, entitled "FACET JOINT IMPLANTS," filed on Oct. 30, 2008 and U.S. Provisional Patent Application No. 61/059,726, entitled "SPINE DISTRACTION DEVICE," filed on Jun. 6, 2008. The full disclosures of the above-listed patent applications are hereby incorporated by reference herein.

FIELD

The following detailed description relates to a device for distracting the spine. More particularly the description relates to a tool for distracting a facet joint of the spine and an implant for maintaining the distracted position of the joint. More particularly the description relates to an implant that may be used together with a tool to distract a facet joint, the implant remaining in place separated from the tool. In some instances, the implant itself may extract the joint.

BACKGROUND

Chronic back problems cause pain and disability for a large segment of the population. Adverse spinal conditions may be characteristic of age. In particular, spinal stenosis (including, but not limited to, central, canal, and lateral stenosis) and facet arthropathy may increase with age. Spinal stenosis results in a reduction of foraminal area (i.e. the available space for the passage of nerves and blood vessels), which may compress cervical nerve roots and cause radicular pain. Both neck extension and ipsilateral rotation, in contrast to neck flexion, may further reduce the foraminal area and contribute to pain, nerve root compression, and neural injury.

Cervical disc herniations may be a factor in spinal stenosis and may predominantly present upper extremity radicular symptoms. In this case, treatment may take the form of closed traction. A number of closed traction devices are available that alleviate pain by pulling on the head to increase foraminal height. Cervical disc herniations may also be treated with anterior and posterior surgery. Many of these surgeries are performed through an anterior approach, which requires a spinal fusion. These surgeries may be expensive and beget additional surgeries due to changing the biomechanics of the neck. There is a three percent incidence of re-operation after cervical spine surgery. Moreover, these surgeries may be highly invasive leading to long recovery times.

There is a need in the art for a device and procedure to increase foraminal height to reduce radicular symptoms of patients suffering the effects of spinal stenosis. There is also a need for the device to be adapted to allow for the procedure to be minimally invasive and to avoid modifying the biomechanics of the spine.

BRIEF SUMMARY

In one embodiment, a spinal joint distraction system may include a driver assembly including a tubular shaft having a longitudinal axis and a pair of implant holder arms positioned on a distal end of the tubular shaft, where the arms are configured to hold a spinal implant. In another embodiment, the driver assembly may also include an implant distractor positioned along the longitudinal axis near the distal end of the tubular shaft, an internal actuator positioned within the tubular shaft and adapted to advance the implant distractor, and a distractor knob adapted to control the internal actuator. In another embodiment, the system may also include a delivery device with a tubular shaft, a receiving assembly positioned on a proximal end of the tubular shaft, and a pair of forks extending from a distal end of the tubular shaft, where the may be adapted to penetrate a facet joint and the delivery device may be adapted to slidably receive the driver assembly. In some embodiments, the system may include an implant adapted for holding by the implant holding arms of the driver assembly. In some other embodiments, the system may include a chisel with a shaft portion, a tip at a distal end of the shaft, and a head at a proximal end of the shaft, where the delivery device is adapted to receive the chisel, and the head of the chisel is adapted to be tapped by a driving member to insert the tip of the chisel into a facet joint. In still other embodiments, the system may include an injector with a cannula with a closed distal end and two exit doors positioned on opposite sides of the distal end, a plunger with a seal positioned within the cannula, a stop disc at a proximal end of the cannula, and a handle positioned on a proximal end of the plunger, where the delivery device is further adapted to receive an injector.

In another embodiment, a spinal distraction implant may include an upper member and a lower member, the upper and lower member being generally rectangular and each having a distal edge, a proximal edge, and two parallel lateral edges, the upper and lower member positioned adjacent and substantially parallel to each other and having an inner surface and an outer surface, the distal edges of the upper and lower member connected to each other and the proximal edges adapted to receive an implant distractor, and teeth positioned along the lateral edges of at least one of the upper or lower member and extending outwardly. In another embodiment, the implant may include flanges extending substantially orthogonally from a proximal end of the upper and lower members. In some embodiments, the flanges may include openings for receiving anchors to anchor the implant to a lateral mass of a facet joint.

In another embodiment, a method of distracting a facet joint of the spine may include inserting a delivery device to access the facet joint of a patient, inserting a driver assembly holding an implant into the delivery device, and actuating the driver assembly thereby distracting the implant.

In another embodiment, a spinal distraction implant may include an upper member, a lower member, and a proximal member, the upper and lower members being generally rectangular and each having a distal edge and two parallel lateral edges, the upper and lower members extending generally continuously into each other to form the proximal member, the upper and lower member positioned adjacent and substantially parallel to each other and having an inner surface and an outer surface, the proximal member being generally perpendicular relative to the upper and lower members, at least one of the upper and lower members further including threaded slots adapted to receive threads of an implant distractor and outwardly extending teeth positioned along the lateral edges of at least one of the upper or lower members. In another embodiment, the proximal member may include a penetration for receiving an implant distractor.

In another embodiment, a spinal distraction implant may include a threaded bolt with a proximal end terminating in a head, a proximal non-threaded block positioned along the bolt and abutting the head of the bolt, a distal threaded block positioned a distance away from the proximal threaded block, and a plurality of expansion members positioned between the proximal and the distal threaded blocks. In one embodiment, the plurality of expansion members may be V-shaped members. In another embodiment, the plurality of V-shaped members may be adapted to deformably flatten out and expand laterally when compressed between the distal and proximal blocks. In another embodiment, the plurality of expansion members may be planar plates with slotted holes such that when freely positioned on the bolt, the plates are positioned in a skewed position relative to a longitudinal axis of the bolt. In another embodiment, the planar plates may be adapted to engage one another and thus position themselves perpendicular to the bolt when compressed between the distal and proximal blocks.

In another embodiment, a spinal distraction implant may include a pair of stacked structures separated by a sloping plane, the structures having an engagement surface along the plane including ratchet teeth. In one embodiment, a first structure of the pair of stacked structures increases in thickness in a proximal direction and a second structure of the pair of stacked structures increases in thickness in a distal direction.

In another embodiment, a spinal distraction implant may include a generally tapered shaft in the form of a screw, the shaft defining a longitudinal axis and having a length, the shaft having threads along an outer surface for engaging articular surfaces of a facet joint. In one embodiment, the threads may be notched along the length of the implant creating serrations for cutting into the articular surfaces of a facet joint. In another embodiment, the threads may include leaf springs for preventing backing out of the implant. In another embodiment, the threads may have a T-shaped cross-section. In another embodiment, the implant may include a relatively broad head with a decorticating feature on a distal surface thereof. In another embodiment, the decorticating feature may include tabs projecting distally from the head. In another embodiment, the decorticating feature may include spurs. In another embodiment, the head may be in the form of a floating collar and be free to pivot about the longitudinal axis of the implant in a ball and socket type fashion. In another embodiment, the implant may include a torque limiting mechanism. In another embodiment, the shaft may include a hollow cavity and take the form of a cone, the cone being made from a relatively malleable material, the implant further including an inner core support member for use when inserting the implant and for removal once the implant is in place. In still another embodiment, the generally tapered shaft may be a first tapered shaft and the implant may also include a second generally tapered shaft in the form of a screw where the second generally tapered shaft may be positioned adjacent to the first generally tapered shaft and have communicative threaded serrations such that when one shaft is rotated, the other shaft rotates in the opposite direction. In another embodiment, the implant may include an arm type locking mechanism, the arm being biased in a distal direction such that when implanted the arm provides a biasing force to maintain friction on the threads. In another embodiment, the arm may have engaging teeth. In another embodiment, the implant may include flaps extending from the head of the shaft and including teeth for engaging a lateral mass of a facet joint.

In another embodiment, a spinal distraction implant may include a plate and a orthogonally positioned bumper, the superior aspect of the bumper having a rounded surface for opposing the lateral mass of a superior vertebra, the implant including an anchoring screw for securing the implant to a lateral mass of a facet joint.

In another embodiment, a spinal distraction implant may include a wedge insertable between facet surfaces, the wedge having teeth on at least one of an anterior and inferior surface thereof. In another embodiment, the implant may also include a diagonally placed anchor screw positioned through the implant for advancing into the surface of a facet joint.

In another embodiment, a spinal distraction implant may include an anterior hook, a posterior hook, and a bolt joining the anterior and posterior hook. In another embodiment, the anterior hook may be C-shaped with a lip and the posterior hook may be S-shaped with a lip, the anterior hook adapted to engage the anterior aspect of the inferior facet and the posterior hook adapted to engage the posterior aspect of the posterior facet.

In another embodiment, a spinal distraction implant may include an insert and tabs positioned to extend orthogonally from a proximal end of the insert. In one embodiment, the insert may be rectangular and the tabs may have holes for receiving an anchor.

In another embodiment, a spinal distraction implant may include a collapsible diamond shaped structure including two opposing threaded corners, and two opposing non-threaded corners including pads. The implant may also include a bolt threaded through the threaded corners of the diamond shaped structure, where actuating the bolt draws the threaded corners together and extends the non-threaded corners.

In another embodiment, a spinal distraction implant may include an upper member, a lower member, a hinge connecting the upper member to the lower member, and a brace member for maintaining the implant in an open position.

In another embodiment, a spinal distraction implant may include a generally cylindrically shaped member including at least two sections separated by a slot, the sections connected together at distal ends to form a tip, the member adapted to receive a screw to cause it to expand, and the outer surface of the sections including teeth for engaging articular surfaces of a facet joint.

In another embodiment, a method of securing a superior vertebra may include applying a force to the superior vertebra to increase the foraminal area between the superior vertebra and an inferior vertebra and placing an angled screw through a superior facet, through a facet capsule, and into an inferior facet.

In another embodiment, a spinal distraction implant may include a collapsible triangular shaped implant including a central shaft and at least two springing leaves connected to the distal end of the shaft, extending proximally along the shaft, and biased in a direction to form an arrow shape, where the implant may be collapsed within a tube and delivered to a site where the tube is removed and the implant is allowed to expand.

In another embodiment, a spinal distraction implant may include a facet spacer plate and screw, wherein the screw may be inserted diagonally through a facet surface to engage the facet spacer plate thereby forcing separation of a facet joint. In another embodiment, the spacer may have a C-shape and the screw may pass through the spacer plate prior to entering the spinal structure.

In another embodiment, a spinal distraction implant may include a first bracket, second bracket, and a bolt extending between the brackets, where the brackets are adapted to separate when the bolt is turned. In another embodiment, the first and second brackets may be adapted to be attached to a lateral mass of a facet joint. In yet another embodiment, the first and second brackets may include a leg adapted to be inserted into a facet joint.

In another embodiment, a spinal distraction implant may include a triangular shaped wedge, an anchor screw positioned diagonally through the wedge, and a malleable flap extending from the wedge including teeth for engaging a lateral mass of a facet joint.

In another embodiment, a spinal distraction implant may include an anchoring plug, an expandable plate, and two external plates, where securing the external plates to a lateral mass of a facet joint and inserting the anchoring plug causes the facet joint to separate.

In another embodiment, a spinal distraction implant may include a delivery system and at least two nitinol hooks, where the hooks may be flattened and inserted with the delivery system and once in place may be allowed to assume their pre-flattened shape.

In another embodiment, a spinal distraction implant may include a hollow screw sleeve having barbs adapted to be ejected from a retracted position and a wedge adapted to be inserted in the hollow screw sleeve to eject the barbs.

In another embodiment, a spinal distraction implant may include a collapsible nut positioned over a bolt, the bolt defining a longitudinal axis, where advancing the bolt may cause the nut to collapse along the longitudinal axis in an accordion shape, thereby expanding laterally.

In another embodiment, a spinal distraction implant may include a collapsible plate positioned over a bolt, the bolt defining a longitudinal axis, where advancing the bolt causes the plate to collapse along the longitudinal axis in an accordion shape, thereby expanding laterally.

In another embodiment, a spinal distraction implant may include a wire surrounding a block in a helical fashion, the wire adapted to contract and expand laterally when pulled taught or released respectively.

In another embodiment, a spinal distraction implant may include an outer housing and an internal spring, where the housing may be biased to be in a laterally broad position when the spring is in a neutral position.

In another embodiment, a spinal distraction implant may include a pair of stacked structures separated by a sloping plane and a fastener positioned at an angle through the pair of structures thereby preventing relative movement along the plane.

In another embodiment, a spinal distraction implant may include a collapsible cylinder with side cutouts, the cylinder made from a resilient elastic material.

In another embodiment, a spinal distraction implant may include a distal tip of a delivery tool, where the tip is adapted to distract a facet joint and detach from the delivery tool.

In another embodiment, a spinal distraction implant may include a housing, a central gear rotatably positioned within the housing, and two plates slidably positioned in the housing and positioned opposite one another adjacent to the central gear and including teeth for engaging the gear, where rotating the gear slidably extends the plates beyond an outer surface of the housing in opposite directions.

In another embodiment, a spinal distraction implant may include a triangularly bent plate with a first and second bracket on each side, the first bracket adapted to receive an anchor screw and the second bracket including teeth for biting into a lateral mass of a facet joint.

In another embodiment, a spinal distraction implant may include a rotatable cone with a longitudinal axis including a shoulder with a ledge defining a cam surface and an anchor screw, where the shoulder is adapted to be inserted into a facet joint and the implant rotated to cause a superior facet to ride upward along the cam surface and distract the joint, wherein the screw may be advanced to secure the implant.

In another embodiment, a spinal distraction implant may include a housing with penetrations for ejection of spikes, internal spikes positioned with the housing and in alignment with the penetrations, and an internal wire routed through the spike positions, where pulling the wire taught forces the spikes from the housing to engage articular surfaces of a facet joint.

In another embodiment, a spinal distraction implant may include a housing, a cavity within the housing, penetrations on lateral surfaces of the housing extending from the cavity through the wall of the housing, spikes positioned to be ejected through the penetrations, the spikes having a beveled inner surface, and a piston having a torpedo shaped distal end positioned within the cavity, where advancing the piston engages the torpedo shaped distal end with the beveled inner surface of the spikes causing them to eject through the penetrations and engage articular surfaces of a facet joint.

In another embodiment, a spinal distraction implant may include two parallel equal length side bars and at least two struts pivotably positioned between the side bars at each end, the struts having textured surfaces on each end thereof, where the struts may be pivoted to lie in plane with and parallel to the side bars and once in position in a facet joint, may be pivoted substantially perpendicular to the side bars to distract the facet joint.

Further aspects of the invention will be brought out in the following portions of the specification, wherein the detailed description is for the purpose of fully disclosing preferred embodiments of the invention without placing limitations thereon.

BRIEF DESCRIPTION OF DRAWINGS

The invention will be more fully understood by reference to the following drawings which are for illustrative purposes only:

FIG. 6A-6C are perspective views of a delivery device and an internal decorticator, according to certain embodiments.

FIG. 8 is a perspective view of a delivery device with a driver assembly and implant poised for insertion into the delivery device, according to certain embodiments.

FIG. 9 is a close-up view of a distal end of a driver assembly and a delivery device, according to certain embodiments.

FIG. 10 is close-up view of a distal end of a driver assembly, according to certain embodiments.

FIG. 11 is a perspective view of an implant and a distal end of a driver assembly, according to certain embodiments.

FIG. 12 is a perspective view of distal end of a driver assembly holding an implant, according to certain embodiments.

FIG. 13 is a perspective view of a distal end of a driver assembly positioned within a delivery device, according to certain embodiments.

FIG. 14 is a perspective view of an implant distractor, according to certain embodiments.

FIG. 15 is a perspective view of a distal end of a driver assembly positioned within a delivery device, according to certain embodiments.

FIG. 16 is a perspective view of an implant according to certain embodiments.

FIG. 17 is a side view of an implant according to certain embodiments.

FIG. 18 is a top view of an implant according to certain embodiments.

FIG. 19 is a proximal end view of an implant according to certain embodiments.

FIG. 25 is perspective view of a deliver device with a driver assembly inserted and advance, according to certain embodiments.

FIGS. 39A-D include side and perspective views of an implant, according to certain embodiments.

FIGS. 44A-D include side and perspective views of an implant, according to certain embodiments.

FIGS. 57A-C include side and perspective views of an implant, according to certain embodiments.

FIGS. 80A-D include side and perspective views of an implant, according to certain embodiments.

FIGS. 82A-F include side and perspective views of an implant, according to certain embodiments.

FIG. 86 is an assembled perspective view of a kit, according to certain embodiments.

FIGS. 87 and 88 are perspective views of a chisel portion of the kit shown in FIGS. 85 and 86.

FIGS. 89 and 90 are perspective views of a delivery device portion of the kit shown in FIGS. 85 and 86.

FIGS. 92 and 93 are perspective views of a part of a driver assembly portion of the kit shown in FIGS. 85 and 86.

DETAILED DESCRIPTION

The following description generally relates to devices and methods for treating spinal stenosis. Spinal stenosis reflects a narrowing of one or more areas of the spine often in the upper or lower back. This narrowing can put pressure on the spinal cord or on the nerves that branch out from the compressed areas. Individual vertebrae of the spine are positioned relative to each other and their separation is maintained by discs separating main vertebral bodies and by capsules positioned within facet joints. The discs and capsules are separated from the bone of their respective joints by cartilage. Spinal stenosis is often indicative of degeneration of a disc, a capsule, or the cartilage in a joint, which leads to a compression of the joints and the narrowing mentioned.

As such, the following detailed description includes discussion of a device for distracting a facet joint of the spine to remedy this condition. The device may include a tool and an implant for distracting and maintaining the distracted position of the joint. Several embodiments of an implant are described in addition to several embodiments of a tool. In addition, several embodiments are described where the implant and the tool work together to distract the facet joint and thereafter leave the implant behind to maintain the distraction of the joint. In short, the device may be adapted to access a facet joint by inserting a delivery tool and an implant, forcibly separate the associated articular surfaces with the tool, the implant, or both, and leave the implant in place to maintain the separation of the articular surfaces. This approach may allow for maintaining the distraction of the joint, thereby relieving symptoms associated with spinal stenosis.

The present application hereby incorporates the following U.S. patent applications by reference herein in their entireties: U.S. patent application Ser. No. 11/618,619, which was filed on Dec. 29, 2006 and is entitled Cervical Distraction Device; U.S. Provisional Patent Application No. 61/020,082, which was filed on Jan. 9, 2008 and is entitled Methods and Apparatus for Accessing and Treating the Facet Joint; U.S. Provisional Application No. 61/059,723, which was filed on Jun. 6, 2008 and is entitled Spine Distraction Device; U.S. Provisional Application No. 61/097,103, which was filed on Sep. 15, 2008 and is entitled Cervical Distraction/Implant Delivery Device; and U.S. Provisional Application No. 61/109,776, which was filed on Oct. 30, 2008 and is entitled Facet Joint Implants.

Figure 1:
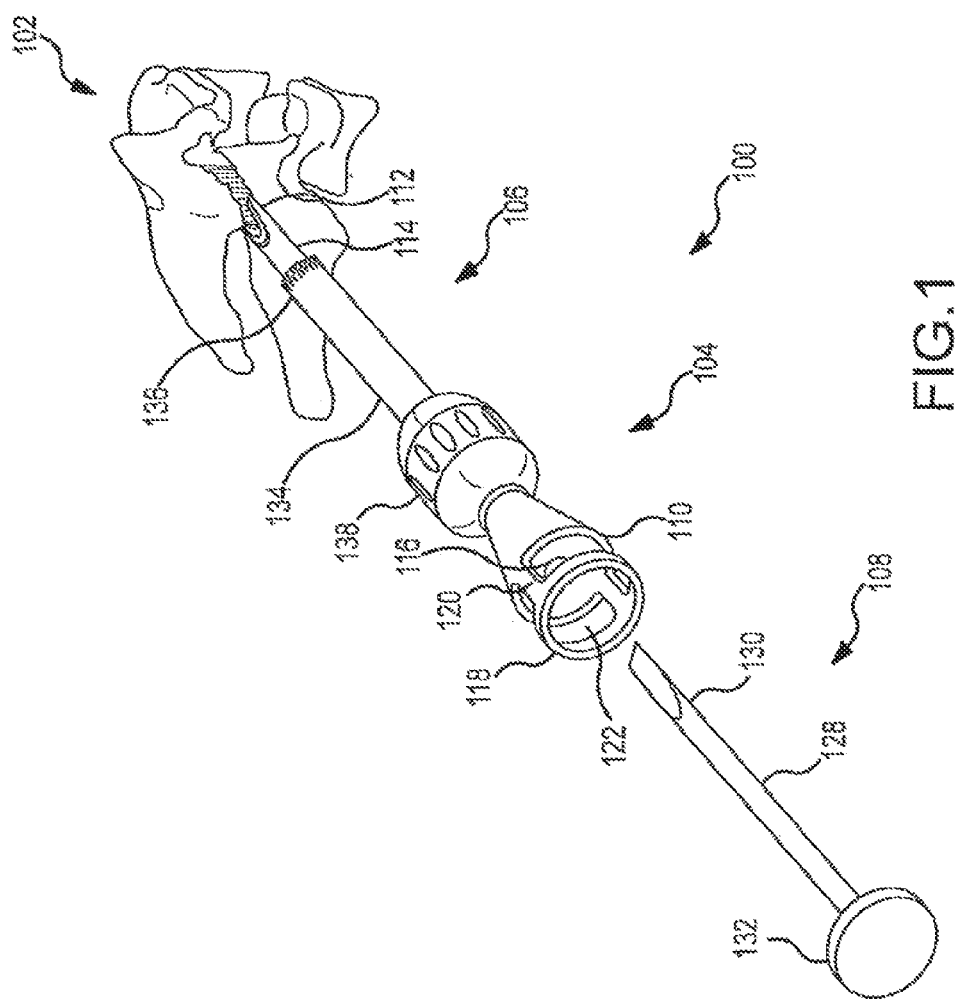
FIG. 1 is a perspective view of a delivery device and chisel positioned relative to a facet joint of a spine, according to certain embodiments.

Referring now to FIGS. 1-28, a first embodiment of a tool and an implant is shown. FIG. 1 shows the tool 100 in position posterior to the spine 102. The tool 100 includes a delivery device 104, a decorticator 106, and a chisel 108.

The delivery device 104 may include a receiving assembly 110 at a proximal end, anchoring forks 112 at a distal end, and a generally tubular shaft 114 defining a longitudinal axis and extending between the receiving assembly 110 and the anchoring forks 112. The tubular shaft 114 may have an annular shaped cross-section with an inner radius and an outer radius, where the difference between the two radii defines a thickness of the tubular shaft 114.

The receiving assembly 110 of the delivery device 104 may have a generally conical outer surface defining a generally hollow volume or solid mass. The conical outer surface may have a longitudinal axis that coincides with that of the tubular shaft 114. The conical outer surface may be defined by a first radius at a proximal end and a second radius at a distal end. Where the tubular shaft 114 and the receiving assembly 110 are manufactured as one piece, the second radius may match the outer radius of the tubular shaft. Alternatively, the distal end of the receiving assembly 110 may be adapted for a press fit over the proximal end of the tubular shaft 114. The receiving assembly 110 may also include a longitudinally extending bore 116 having an inner radius matching that of the tubular shaft 114 or may have a conically shaped inner surface leading to the tubular shaft 114. The receiving assembly 110 may also include a relatively thin annular ring 118 offset from its distal end by two relatively thin extension elements 120. The space between the proximal end of the conical portion of the receiving assembly 110 and the distal end of the annular ring 118 may define an access opening 122.

In another embodiment as shown in FIGS. 6A-6C, a receiving assembly 111 may not include the annular ring 118 and the extension elements 120, but may remain generally conical and may include the longitudinally extending bore 116. In addition, near the proximal end of the receiving assembly 111, seating recesses 119 may be included. These recesses 119 may be positioned on opposing sides of the bore 116 and may recess into the proximal end of the receiving assembly 111 and the inner surface of the bore 116. These recesses may function to receive positionally matched protrusions from any one or all of the devices being inserted into the deliver device. As such, the recesses 119, may allow for orienting the devices properly relative to the forks 112 positioned in the facet joint. It is noted that any number of recesses may be provided and that any orientation may be used, either symmetrical or non-symmetrical, such that one or several orientations may be controlled. That is, an asymmetrical arrangement may allow for only one proper insertion position as opposed to the symmetrical orientation shown, which may allow for two proper insertion positions.

Figure 2:
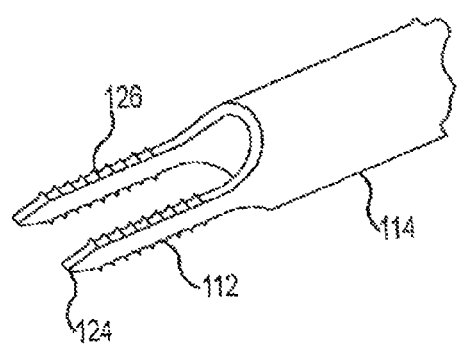
FIG. 2 is a perspective view of a distal end of a delivery device, according to certain embodiments.

As shown in more detail in FIG. 2, the delivery device 104 may include two anchoring forks 112 formed by coping two opposing portions of the distal end of the tubular shaft 114. The forks 112 may have a generally V-shaped tip 124 at their distal end and may have a generally rectangular cross-section extending from the V-shaped tip 124 to the proximal end of the forks 112. The rectangular cross-section may have an inside face and an outside face where the inside face faces the longitudinal axis of the delivery device 104. The rectangular cross-section may also have opposing surfaces connecting the inside face to the outside face and completing the rectangular cross-section. At the proximal end of the forks 112, as suggested by the coping mentioned above, the cross-section may gradually change from rectangular to a shape matching that of half of the annular shape of the tubular shaft portion. The forks 112 may also include serrations or teeth along the opposing surfaces to assist with anchoring the delivery device 104.

Referring again to FIG. 1, the chisel 108 may have a generally cylindrical cross-section forming a shaft 128. The shaft 128 may have a radius substantially equal to the inner radius of the tubular shaft 114 portion of the delivery device 104 allowing for slidable insertion of the chisel 108 within the delivery device 104. The chisel 108 may include a basic single or doubly chamfered tip 130 at a distal end or may have a coped distal end. The chisel 108 may also include a head 132 at a proximal end. The head 132 may be a generally solid material and may have a generally flat distal face and a spherically shaped proximal face. The shaft 128 and tip 130 portion of the chisel 108, measured from the distal face of the head 132 to the distal end of the chamfered tip 130, may have a length substantially equal to the distance from a proximal face of the annular ring 118 of the delivery device 104 to the distal tip of the delivery device 104.

Figure 1A:
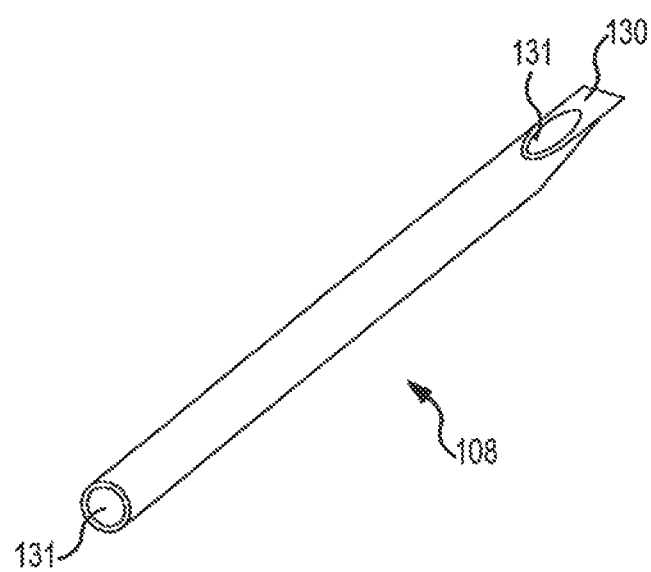
FIG. 1A is a perspective view of a chisel according to certain embodiments.

In another embodiment, the chisel 108 may include a longitudinal lumen 131 as shown in FIG. 1A. While not shown, this embodiment may also include the head 132 shown in FIG. 1 and the lumen 131 may extend there through. The lumen 131 in the chisel 108 may be used for advancing a scope along with the chisel 108 to properly place the chisel 108 and the delivery device 104. The lumen 131 may also be used to provide suction or fluid flushing to the surgical site to remove or flush debris created by inserting the serrated forks 112 of the delivery device 104 and the tip 130 of the chisel 108.

Figure 3:
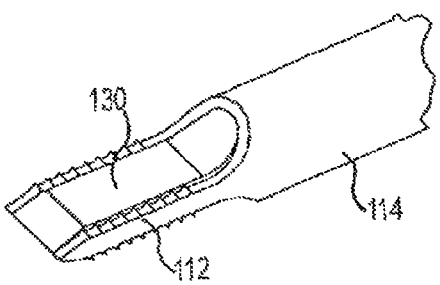
FIG. 3 is a perspective view of a distal end of a delivery device with an advanced chisel, according to certain embodiments

As shown in FIG. 3, the tip 130 of the chisel 108 may have a coped shaped similar to that of the forks 112 of delivery device 104. In this condition, the tip 130 may include a generally V-shaped distal end matching that of the forks 112. The tip 130 may have a width substantially equal to twice the inner radius of the tubular shaft 114 of the delivery device 104 such that the tip 130 extends between the two inside faces of the forks 112.

Figure 4:
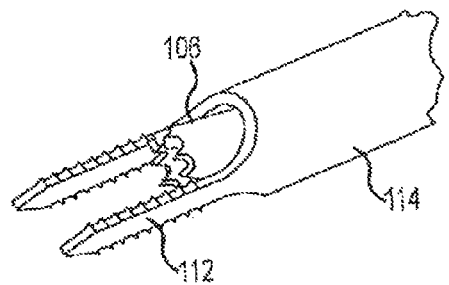
FIG. 4 is a perspective view of a distal end of a delivery device with an advanced internal decorticator, according to certain embodiments.

Referring again to FIG. 1, the decorticator 106 may have a tubular shaft 134 portion, an abrasive distal end 136, and a handle 138 at a proximal end. The tubular shaft 134 may have an inner radius substantially equal to the outer radius of the tubular shaft 114 of the delivery device 104 and may allow for sliding movement of the decorticator 106 along the length of the delivery device 104 and rotationally around the delivery device 104. The abrasive distal end 136 may include serrated teeth as shown, or may include a more flat annular surface with a gritty surface. The handle 138 may have a generally cylindrical portion with randomly or patterned raised portions or recesses adapted to assist gripping the handle. The proximal and distal ends of the handle 138 may be generally spherical. It is noted that the decorticator 106 may alternatively be separate from the delivery device 104 and may be slidably inserted within the delivery device 104 as shown in FIG. 4. In this embodiment, the decorticator 106 may be inserted, advanced to the implantation site, and rotated similar to the decorticator 106 described above to roughen the bone surface.

In still another embodiment, a decorticator 106 may take the form of a relatively sharp pick, as shown in FIG. 6A-6C. As shown in FIG. 6A, the decorticator 106 may include a control handle 139 for advancing and pivoting the device. The control handle 139 may be connected to a tubular shaft 135, which may be connected to a sharp flexible tip 137. As shown, the tip 137 may be relatively thin and may have a neutral position relative to the longitudinal axis of the delivery device 104 so as to position the tip 137 within the boundary defined by the inner surface of the delivery device 104. As such, when inserted in the delivery device 104, the tip 137 may slide readily through the delivery device 104. When the decorticator 106 is advanced to the distal end of the delivery device 104, the tip 137 may be rotated and maneuvered to decorticate the surface of the lateral mass. It is noted that the shaft 135 may be relatively narrow when compared to the inner bore of the delivery device 104 to facilitate better maneuverability of the tip of the decorticator as it extends out the end of the deliver device. The decorticator may be used as shown in FIGS. 6B and 6C to rotationally scrape or longitudinally penetrate the lateral mass of a facet joint. A driving member may be used to assist the decorticating process.

Figure 5:
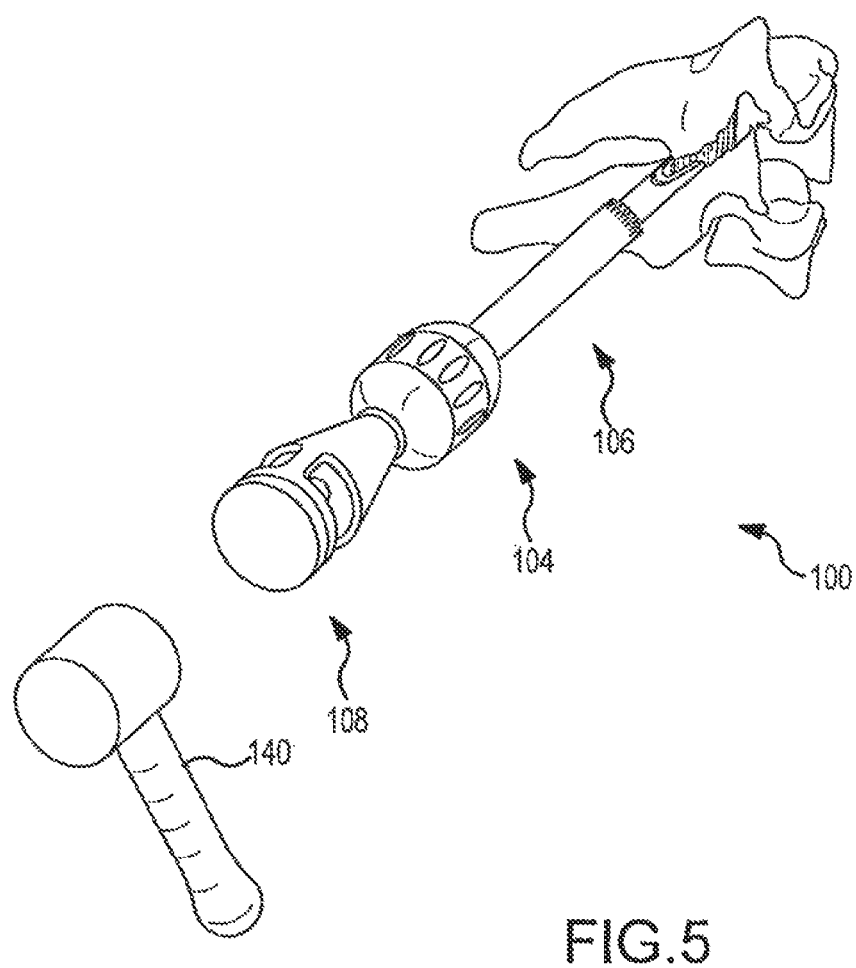
FIG. 5 is a perspective view of a delivery device and chisel positioned relative to a facet joint of a spine with a driving member positioned proximally to the chisel head, according to certain embodiments.

Referring now to FIG. 5, the tool 100 is shown with the chisel 108 fully inserted into the delivery device 104 such that the distal face of the head 132 of the chisel 108 is in abutting relationship with the annular ring 118 of the receiving assembly 110 on the delivery device 104. The distal tip 130 of the chisel 108 thus extends to the distal end of the delivery device 104. A hammer 140 is shown for use in tapping the proximal end of the chisel 108 and thus advancing the forks 112 of the delivery device 104 and the tip 130 of the chisel 108 into the facet joint. As the chisel 108 and the delivery device 104 are advanced into the joint, the forks 112 of the delivery device may channel into the fact surface and displace or remove tissue. In some embodiments, this may be removed by a suction lumen in the chisel. Once the chisel 108 and delivery device 104 are tapped into place, the chisel 108 may be removed and the serrations on the opposing surfaces of the forks 112 may aid in anchoring the delivery device 104 in the joint and preventing dislodgement.

Figure 6:
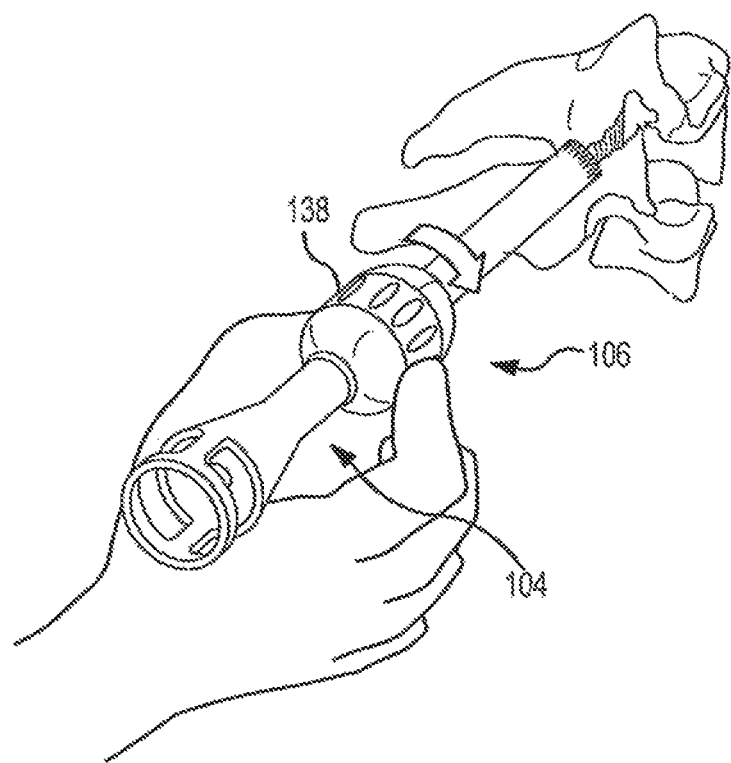
FIG. 6 is a perspective view of a delivery device with an exterior decorticator in an advanced position, according to certain embodiments.

FIG. 6 shows the decorticator 106 in an advanced position along the length of the delivery device 104 such that the distal end is in contact with the bone surfaces surrounding the facet joint. The handle 138 is being used to rotate the decorticator 106 around the perimeter of the delivery device 104 to roughen the associated bone surfaces. Alternatively, either of the internal decorticators shown in FIG. 4 or 6A-6C may be used.

Figure 7:
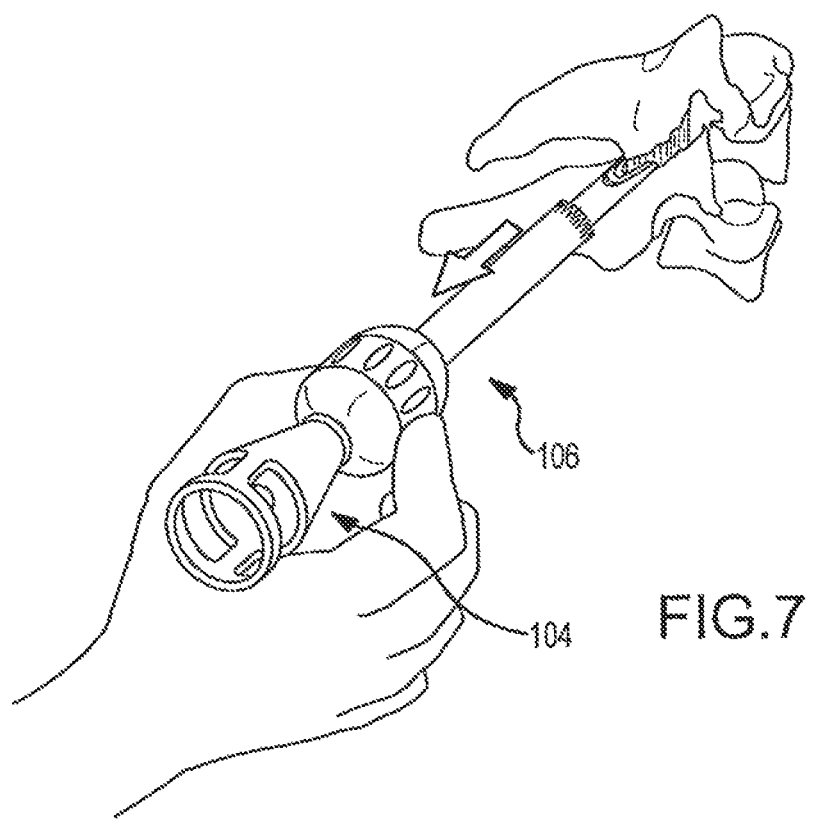
FIG. 7 is a perspective view of a delivery device with an exterior decorticator being retracted, according to certain embodiments.
Figure 18A:
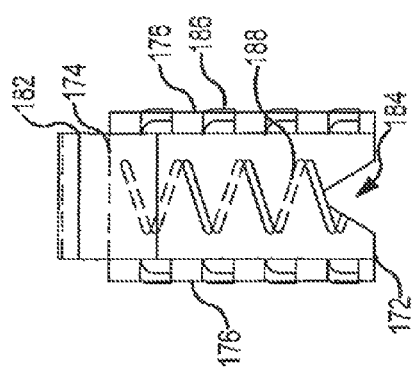
FIG. 18A is a top view of an implant showing the guide feature of FIG. 16A, according to certain embodiments.
Figure 18B:
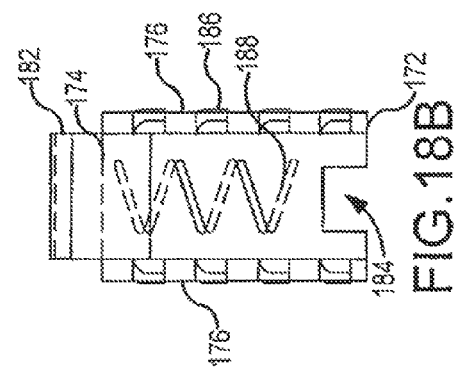
FIG. 18B is a top view of an implant showing the guide feature of FIG. 16B, according to certain embodiments.

FIG. 7 shows the decorticator 106 retracted and also shows the resulting roughened bone surfaces.

Referring now to FIG. 8, the tool 100, including the delivery device 104 and retracted decorticator 106, is shown lodged in a facet joint. Also shown is a driver assembly 142 portion of the tool 100. The driver assembly 142 includes a distractor knob 144, an implant shaft 146, implant holding arms 148, an implant distractor 150, and an internal actuator 152 (not shown). The driver assembly 142 shown is holding an implant 154 and is poised for insertion into the delivery device 104.

Referring now to FIGS. 9-15 several views of the driver assembly 142 are shown. In FIG. 9, a portion of the delivery device 104 is shown for receiving the driver assembly 142. The distal end of the driver assembly 142 is also shown. FIG. 10 shows a close-up view of the distal end of the driver assembly 142 where the implant 154, the implant distractor 150 and the internal actuator 152 are not shown. As shown, the implant shaft 146 of the driver assembly 142 defines a longitudinal axis thereof and has a generally annular cross-section with an inner radius and an outer radius where the difference between the two radii defines the wall thickness of the shaft 146. The outer radius of the implant shaft 146 is substantially equal to the inner radius of the tubular shaft 114 of the delivery device 104. The implant shaft 146 also includes a keyway feature 156 for preventing relative rotation between the tubular shaft 114 of the delivery device 104 and the implant shaft 146 of the driver assembly 142 when inserted. As shown, the keyway feature 156 may include a pair of tabs on opposing sides of the implant shaft 146 for engaging with a corresponding longitudinal slot in the inner surface of the tubular shaft 114 of the delivery device 104. In another embodiment, this keyway feature 156 may be in the form of a longitudinal slot in the outer surface of the implant shaft 146 of the driver assembly 142, as shown in FIG. 11, which may receive an internal ridge, tab, or other protrusion from the inner surface of the tubular shaft 114 of the delivery device 104.

With continued reference to FIG. 10, two arms 148 are shown extending from the distal end of the implant shaft 146. The arms 148 may be formed by coping opposing surfaces of the implant shaft 146. As shown, the arms 148 have a generally rectangular cross-section with an inside face facing the longitudinal axis of the implant shaft 146 and an opposite outside face. The inside and outside faces of the cross-section are connected by two opposing faces. The arms 148 may include an engagement feature 158 at a distal end for engaging an implant 154. As shown, the engagement feature 158 may include a generally rectangular element positioned orthogonal to the arms 148 and flush with the outside face of the arms. As shown in FIG. 9, the implant 154 may slide over the distal end of the arms 148 and may include a receiving feature 160 for receiving the engagement feature 158 of each of the arms 148.

Referring now to FIG. 11, another embodiment of the arms 148 is shown in relation to an implant 154. In this embodiment, the arms 148 may still be formed by coping opposing surfaces of the implant shaft 146. In this embodiment, the outside face of the arm 148 may be a continuation of the outside surface of the implant shaft 146. However, the inside face of the arm 148 is more detailed than that of the embodiment shown in FIG. 10. That is, as shown in FIG. 11, the inside surface may include a longitudinal ridge 162 extending the length of the arm 148. The arm 148 may also include a bull nose engagement feature 158 extending transverse to the longitudinal axis of the implant shaft 146 along the inside face of the arm 148. As shown in FIG. 12, where the arms 148 are engaged with and holding the implant 154, the longitudinal ridges 162 of each arm 148 are positioned between upper and lower planar members of the implant 154 and the bull nose engagement features 158 are positioned in the U-shaped receiving feature slots 160 on the lateral edges of the implant 154.

The implant distractor 150 is shown in FIG. 9 and a close-up view is shown in FIG. 14. The implant distractor 150 may be a generally narrow conical element tapered to a point at a distal end. At a proximal end, the implant distractor 150 is shown to include an extruded hexagon shape 164. In the present embodiment, the outer surface of the implant distractor 150 includes a continuous coil-shaped thread feature 166. The implant distractor 150 is shown positioned proximal to the implant 154 and engaged by the internal actuator 152. Those of skill in the art will understand and appreciate that the implant distractor 150 may take on a variety of shapes and sizes other than that shown in the present embodiment. For example, the implant distractor 150 may be a triangular shaped wedge, a generally conical shape without threads, or other shape adapted to cause separation and distraction of a facet joint.

Referring again to FIG. 9, the internal actuator 152 is visible extending from the distal end of the implant shaft 146. The internal actuator 152 generally includes a longitudinal shaft positioned within the driver assembly 142. The internal actuator 152 may have a radius substantially equal to the inner radius of the driver assembly 142 and may be adapted for slidable longitudinal and rotational movement relative to the driver assembly 142. The internal actuator 152 may be moved relative to the implant shaft 146 longitudinally, rotationally, or both via the distractor knob 144 and may cause a corresponding motion of the implant distractor 150. As such, the internal actuator 152 may advance the implant distractor 150 into the implant 154 thus expanding the implant 154 in the joint causing distraction of the joint. The distal end of the internal actuator 152 may include a hex driver type tip as most clearly shown in FIG. 15 for engaging the extruded hexagonal shaped proximal end of the implant distractor 150. Those skilled in the art will understand and appreciate that several driving engagements are known in the art including flat screwdriver types, phillips head types, square drive, etc. and that these are within the scope of the invention.

In one embodiment, when the driver assembly 142 is inserted, it may carry the internal actuator 152, the implant distractor 150, as well as the implant 154 with it. However, to properly position the driver assembly 142 and the implant 154, some force may be required via a mallet or other member driving member. In this embodiment, the internal actuator 152 may be slightly isolated from the driver assembly 142, so as to avoid advancing the internal actuator 152, and thus the implant distractor 150, when forcing the driver assembly 142 into the joint. This isolation may help to avoid inadvertently advancing the internal actuator 152 and the implant distractor 150, thus avoiding inadvertent distraction prior to proper placement. The isolation of the internal actuator 152 from the driver assembly may take the form of a loosely fitting threaded engagement between the driver assembly 142 and the internal actuator 152. Alternatively, this isolation may be in the form of a clip between the two features.

For a detailed discussion of an implant 154 according to certain embodiments, reference is now made to FIGS. 16-24.

Figure 23:
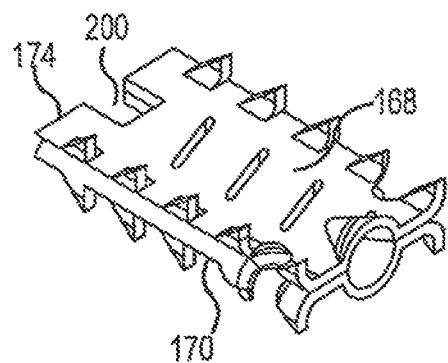
FIG. 23 is a perspective view of an implant according to certain embodiments.
Figure 24:
FIG. 24 is a top view of an implant according to certain embodiments.
Figure 23A:
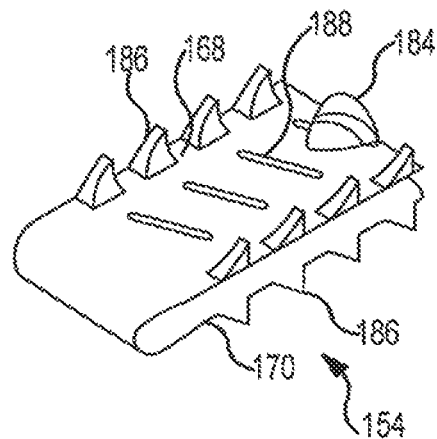
FIG. 23A is a perspective view of an implant according to certain embodiments.
Figure 24A:
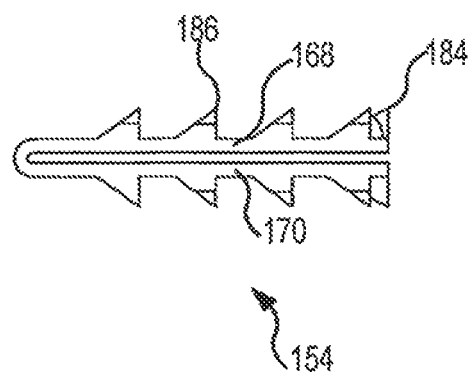
FIG. 24A is a side view of the implant shown in FIG. 23A, according to certain embodiments.

As can be understood from FIGS. 16 and 17, the implant 154 may include upper 168 and lower 170 members. The members 168, 170 may be generally planar and may also be generally rectangular. As most clearly shown in FIG. 18, each of the upper 168 and lower 170 members may include a proximal edge 172, a distal edge 174, and a pair of parallel lateral edges 176 extending longitudinally between the distal edges 174 and the proximal edges 172. The distal 174 and proximal edges 172 may be generally square edges, while the lateral edges 176 may be defined by a radiused curve. As shown in cross-section in FIG. 19, the inner surface 178 of the upper 168 and lower 170 member may be generally flat as it approaches the lateral edge 176. Gradually, the inner surface 178 departs from generally flat and follows a radiused curve until it intersects with the outer surface 180. The members 168, 170 may be joined at their respective distal edges 174 by a U-member 182 to form a leading end. Alternatively, as shown in FIGS. 23 and 24, the leading end may be formed via a weld (not shown) that couples the distal edges 174 of the planar members 168, 170 together. In yet another embodiment, the upper 168 and lower 170 members may be formed from a single plate bent to create the implant as shown in FIGS. 23A and 24A. In any or all of these embodiments, the planar members 168, 170 may be biased by the leading end to be generally parallel to each other, the inner faces 178 of the planar members 168, 170 facing each other in an opposed fashion and abutting or nearly abutting each other. A guide feature 184 may be included on each of the upper 168 and lower 170 members as well as teeth 186 projecting outwardly from the outer faces 180 of the members 168, 170. The receiving features 160 mentioned above with respect to FIGS. 11 and 12 may also be included. Threaded slots 188 may also be included in each planar member 168, 170 for receiving the coil-shaped thread feature 166 on the implant distractor 150.

Figure 16A:
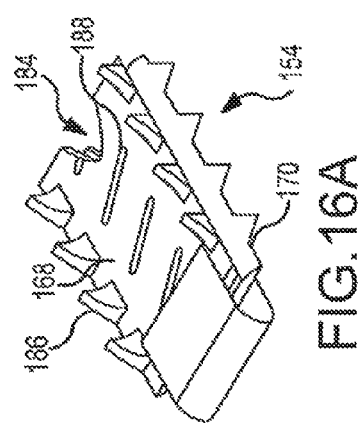
FIG. 16A is a perspective view of an implant showing a guide feature, according to certain embodiments.
Figure 16B:
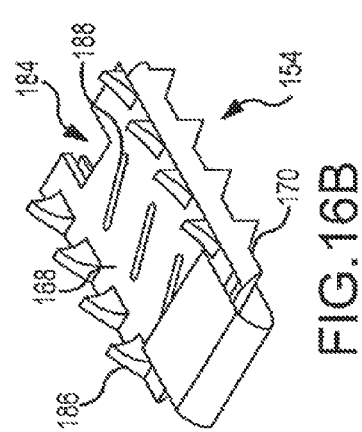
FIG. 16B is a perspective view of an implant showing a guide feature, according to certain embodiments.

With continued reference to FIGS. 16 and 17, the guide feature 184 may take the form of a half-conical feature and may be positioned at or near the proximal edge 172 of each of the upper 168 and lower 170 members. The half-conical feature may begin at the proximal edge 172 with the widest radius of the half-conical feature and may taper to a zero or approximately zero radius as the half-conical feature extends in the direction of the distal edge 174. Where the upper 168 and lower 170 members are in parallel position, the half conical features may oppose one another and function to receive and guide an advancing implant distractor 150. As such, like the upper 168 and lower 170 members described above, the half-conical features may also include threaded slots 188 for receiving the coil-shaped thread feature 166 on the implant distractor 150. In other embodiments, the half-conical feature may not actually be a full half cone. Instead, the proximal end of the feature may be a segment of a circle and the feature may be relatively subtle in the form of a cone segment. In another embodiment the guide feature 184 may include a V-shaped notch or a rectangular notch in the proximal end of the upper 168 and lower 170 members as shown in FIGS. 16A and 18A and FIGS. 16B and 18B respectively. Those skilled in the art will understand and appreciate that other shaped notches or elements may be positioned on proximal end of the upper 168 and lower 170 members to guide the implant distractor 150, and these elements are within the scope of the present disclosure.

As shown, the upper 168 and lower 170 members may also each include teeth 186 projecting outwardly (e.g. a direction opposite the position of the other upper or lower member) from the outer surfaces 180 of the upper 168 and lower 170 members. As shown in FIG. 17, the teeth 186 may be equally spaced along each lateral edge 176 and may have a linearly sloped distal face 190 and a proximal face 192 oriented orthogonally to its respective upper 168 or lower 170 member. The distal face 190 and proximal face 192 may intersect to form a point 194. The teeth 186 may also be bounded by opposing inside 196 and outside 198 lateral faces separated by a thickness approximately equal to the thickness of the upper 168 and lower 170 members. As shown in FIG. 19, the outside face 198 of the teeth 186 follows an extension of the radiused curve formed by the inner surface 178 of the upper 168 or lower 170 member at the lateral edge 176, this curve being referred to as a first radiused curve. Additionally, the inside face 196 of the teeth 186 follows a second radiused curve offset from the first radiused curve, such that the teeth 186 have a generally constant thickness from the location where they depart from the outer surface 180 of the upper 168 or lower 170 member to the point 194. The radiused shape of the teeth 186 allows the implant 154 to slidably engage the inside of the delivery device 104 when it is advanced toward the implantation site. Those skilled in the art will understand and appreciate that one, as opposed to both, of the upper 168 and lower 170 members may include teeth 186 to facilitate freedom of motion of the facet joint once the implant 154 is in place.

Figure 20:
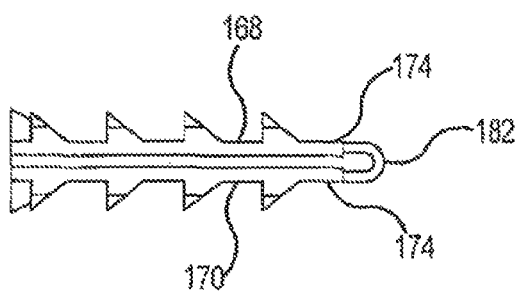
FIG. 20 is a side view of an implant according to certain embodiments.
Figure 21:
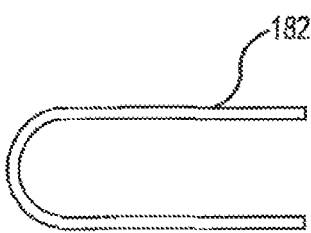
FIG. 21 is side view of a U-member according to certain embodiments.
Figure 22:
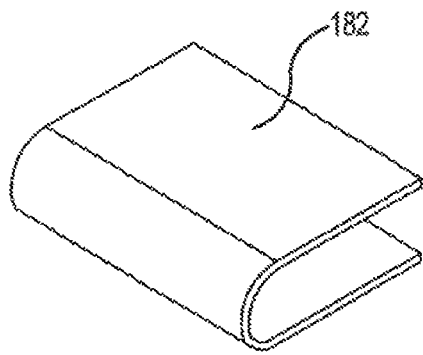
FIG. 22 is a perspective view of a U-member according to certain embodiments.

As shown in FIGS. 16 and 17, where a U-member 182 is used to connect the upper 168 and lower 170 members, the U-member 182 may overlap the upper 168 and lower 170 members. Alternatively, as shown in FIG. 20, the U-member 182 may attach to the distal ends 174 of the upper 168 and lower 170 members via a butt joint. In either case, the U-member 182 may be fastened via welding, fusing, or other techniques known in the art. As shown in FIGS. 21 and 22, the U-member 182 may be a relatively thin, generally rectangular piece of material formed into the shape of the letter 'U'. The rectangular piece of material may have a length defined by the amount of overlap of the upper member 168 and the lower member 170 in addition to the length associated with hairpin or U portion of the member 182. The width of the rectangular plate may be substantially equal to the distance between the teeth 186 of the upper 168 and lower 170 members. The U-member 182 may be adapted to provide the parallel biased position mentioned and yet allow distraction of the upper 168 and lower 170 member when a separation force is applied, the proximal edge 172 of the upper 168 and lower 170 member distracting more than the distal edge 174.

As shown in FIGS. 23 and 24, where the distal edges 174 of the upper 168 and lower 170 member are joined via welding, the distal edges 174 may include a notch to facilitate more weld length and to cause flexure to occur in the upper 168 and lower 170 members rather than in the weld itself. Also shown in FIGS. 23 and 24 are the U-shaped receiving feature slots 160 for receiving the bull nosed engagement features 158 of the arms 148 of the driver assembly 142. As shown most clearly in FIG. 24, the U-shaped receiving feature slots 160 are positioned between the equally spaced teeth 186 and extend into the lateral edges 176 of the upper 168 and lower 170 member just beyond the inside edge of where the teeth 186 begin extending from the outer surfaces 180.

The receiving feature 160 may take several forms including a rectangular notch in the lateral edge 176 of the upper 168 and lower 170 member or a U-shaped notch. The receiving feature 160 may be adapted to receive an engagement feature 158 positioned on the arm 148 of the driver assembly 142. The receiving feature 160 may be any shaped recess and may be adapted to be engaged by the engagement feature 158 so as to prevent or limit relative longitudinal motion between the arms 148 and the implant 154, when the implant 154 is in the neutral position. However, when in an expanded or distracted position, the receiving features 160 may be such that they are lifted free of the engagement feature 158 of the arms 148, thus allowing relative longitudinal motion between the driver assembly 142 and the implant 154.

Figure 26:
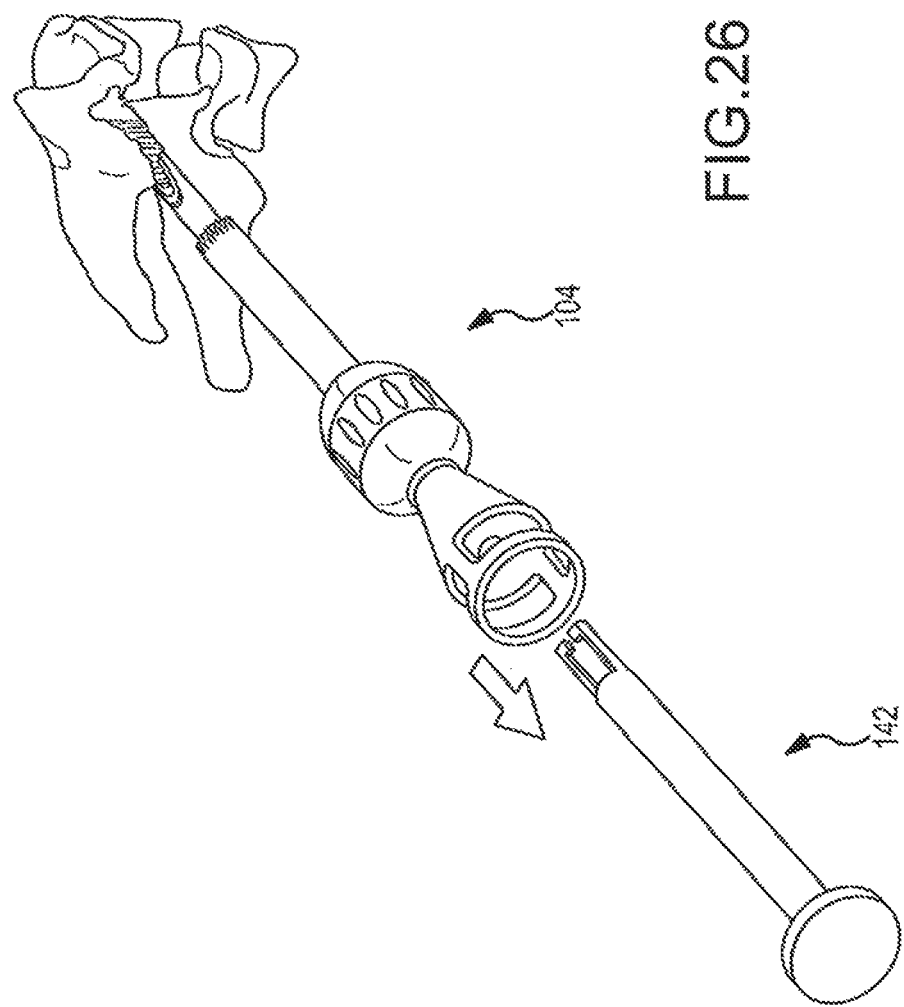
FIG. 26 is perspective view showing the removal of the driver assembly from the delivery device having left the implant behind, according to certain embodiments.

The driver assembly 142 and implant 154 described with respect to FIGS. 8-24, may be used to distract a facet joint. With the delivery device 104 positioned as shown and described with respect to FIG. 7, the implant 154 may be positioned to be held by the arms 148 of the driver assembly 142. The driver assembly 142 and implant 154 may then be inserted into the delivery device 104 and slidably advanced such that the implant 154 is positioned between the forks 112 of the delivery device 104 and within the facet joint. The advanced position of the driver assembly 142 and implant 154 within the delivery device 104 may be most clearly seen in FIG. 13. The proximal end of the driver assembly 142 may be tapped on to fully advance the driver assembly 142 and properly position the implant 154. The implant shaft 146 of the driver assembly 142 may be prevented from rotating by the keyway feature 156 securing it against relative rotation with respect to the delivery device 104. As such, once positioned, the distractor knob 144 of the driver assembly 142 may be turned, as shown in FIG. 25, thereby advancing the internal actuator 152 and further advancing the implant distractor 150. In the embodiment described, the coil-shaped thread feature 166 on the implant distractor 150 may engage the threaded slots 188 of the half-conical features 184 of the upper 168 and lower 170 members of the implant 154. As such, the implant distractor 150 may be guided and remain in position to further engage the threaded slots 188 on the upper 168 and lower 170 members. As the implant distractor 150 continues to advance, those of skill in the art will understand and appreciate that its tapered shape advancing between the upper 168 and lower 170 members will force the upper 168 and lower 170 members of the implant 154 apart causing them to pivot about a point defined by the attachment to each other at their distal ends 174. As the implant 154 continues to be distracted, the upper 168 and lower 170 members of the implant 154 are laterally separated such that they clear the engagement features 158 on the arms 148 of the driver assembly 142. As shown in FIG. 26, when the implant distractor 150 has been fully advanced and the implant 154 is in place, the driver assembly 142 may be slidably removed from the delivery device 104 leaving behind the implant distractor 150 and the implant 154.

Figure 27:
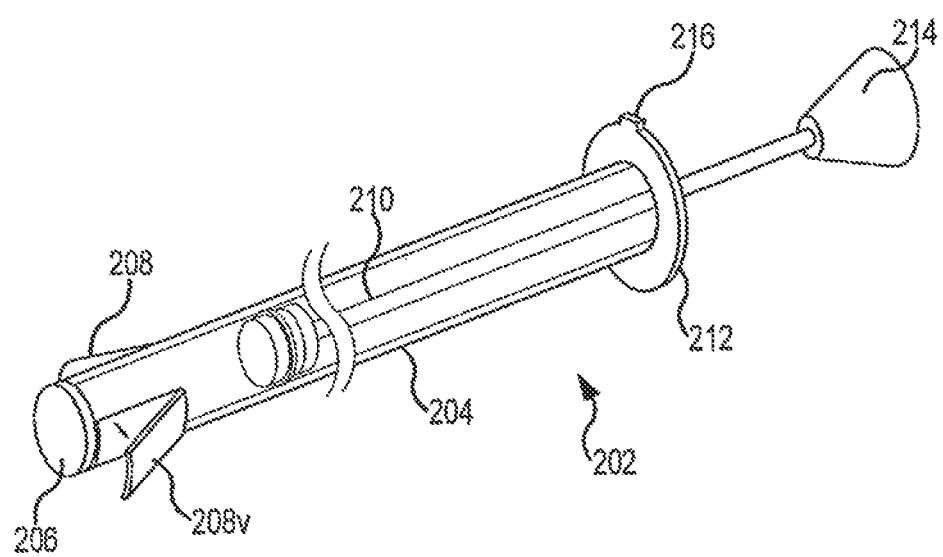
FIG. 27 is a perspective view of an injector, according to certain embodiments.

FIG. 27 shows yet another device, the device being adapted for placing bone paste over the implant 154 in the joint. An injector 202 is shown and includes a syringe type cannula 204 with a closed distal end 206 and two exit doors 208 positioned on opposite sides of the distal end 206 of the cannula 204. The cannula 204 includes a plunger 210 with a seal and further includes a stopping disc 212 at its proximal end, the plunger 210 penetrating the stopping disc 212 and having a handle 214. The cannula 204 may have an outer radius substantially equal to that of the inner radius of the delivery device 104 to allow for slidable engagement of the two devices. The disc 212 at the proximal end is generally flat and is adapted to engage the receiving assembly 110 of the delivery device 104 and provide a stop point for the injector 202 when inserted into the delivery device 104. As shown, the cannula 204 may contain a bone paste material in a liquid form.

Figure 28:
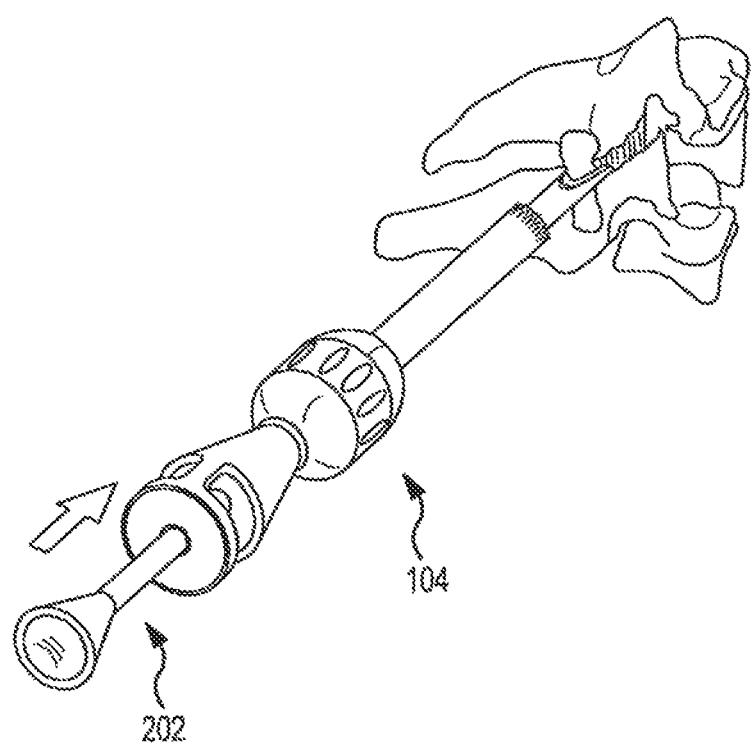
FIG. 28 is a perspective view of a delivery device with an advanced injector inserted and ejecting a material, according to certain embodiments.

As shown in FIG. 28, the injector 202 may be inserted into the delivery device 104 and slidably advanced such that the distal end 206 is near the implantation site and the disc 212 abuts the annular ring 118 of the receiving assembly 110 of the delivery device 104. The injector 202 may be rotatably positioned such that the doors 208 are positioned to open perpendicular to a line connecting the distal ends of the forks 112. The disc 212 may include tabs 216 for such positioning relative to the annular ring 118 on the receiving assembly 110. Once in position, the plunger 210 may be actuated to compress the bone paste material creating an internal pressure which forces the exit doors 208 open allowing the bone paste to escape and flow over the implantation site.

The above description has included some references to use to allow for a better understanding of the structure. Below is a more detailed discussion of that use including the devices and techniques for distracting and retaining a facet joint in a distracted and forwardly translated condition. The implantation procedure may be performed under conscious sedation in order to obtain intra-operative patient symptom feedback.

Initially an incision may be made in the patients back. Tools known in the art may be used to create this incision and to open an access path through the tissues of the back to access the spine. Once an access path is created, the chisel 108 described above may be inserted into the delivery device 104 and the two of them may be inserted through the incision and the distal tip 130 may be positioned adjacent the target facet joint. It is noted that visualization may be provided by first inserting a scope down the delivery device 104 rather than the chisel 108. Additionally, an incision in the facet joint capsule may be made prior to beginning the procedure, and thus prior to insertion of the chisel 108. Once the distal tip of the delivery device 130 is properly positioned adjacent the facet joint and any other preparation steps are completed, the chisel 108 may be inserted. Once the chisel 108 and delivery device 104 are properly positioned, the head 132 of the chisel 108 may be tapped with a driving device 140 such as a hammer or other instrument to advance the distal tip 130 of the chisel 108 and the forks 112 of the delivery device 104 into the facet joint. Once the delivery device 104 is properly positioned, the chisel 108 may be removed. At this point, the implant 154 may be placed in the driver assembly 142 and the implant 154 and driver assembly 142 may be slidably advanced through the delivery device 104. The forks 112 of the delivery device 104 may be holding the facet joint slightly distracted. As such, the implant 154, in its flat and parallel position, may slide relatively easily into the facet joint. To the extent that it does not, the proximal end of the driver assembly 142 may be tapped to properly advance and position the implant 154. Once properly positioned, the distractor knob 144 on the driver assembly may be rotated or otherwise actuated to activate the internal actuator 152. The internal actuator 152 advances the implant distractor 150 into the implant 154 and thus distracts the implant 154. It is noted here that the distraction of the implant 154 may cause the upper 168 and lower 170 member of the implant 154 to clear the engagement features 158 of the holder arms 148 thus allowing the driver assembly 142 to be freely removed from the delivery device 104 leaving the implant 154 and the implant distractor 150 behind. The injector 202 may then be advanced through the delivery device 104 and positioned to allow the doors 208 to open in a direction approximately perpendicular to the forks 112 of the delivery device 104. The handle 214 may be depressed thus advancing the plunger 210 and ejecting the bone paste or other anchoring material. The injector 202 may then be removed. The delivery device 104 may also be removed and the incision closed.

Figure 29:
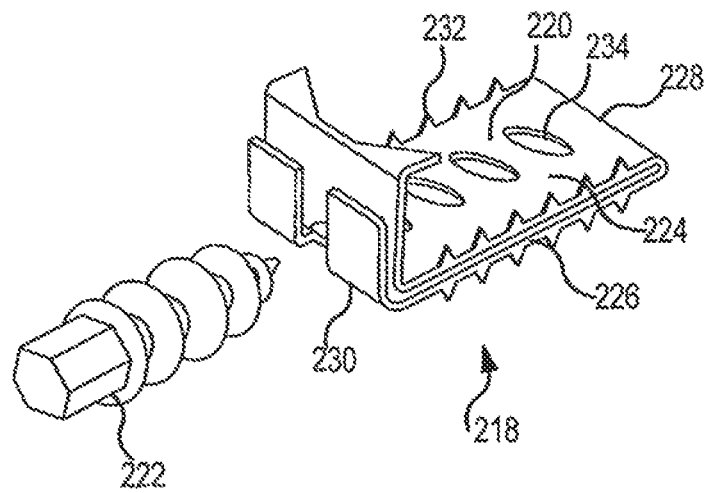
FIG. 29 is a perspective view of an implant in a collapsed position according to certain embodiments.
Figure 30:
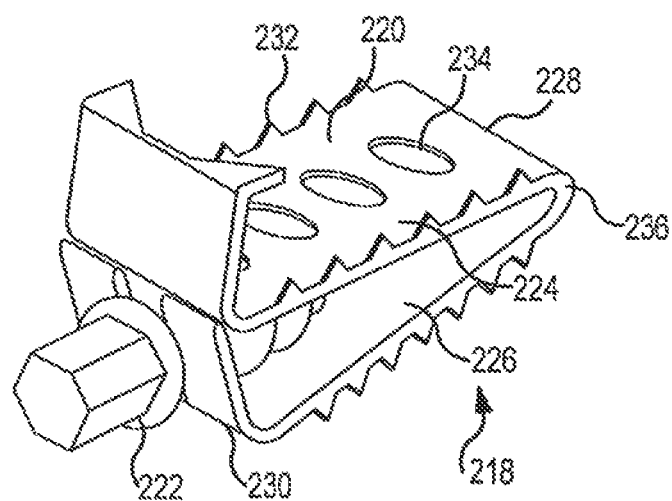
FIG. 30 is a perspective view of an expanded implant according to certain embodiments.

Those skilled in the art will understand and appreciate that several modifications or variations from the above the identified embodiments may be made while still falling within the scope and spirit of the present disclosure. For example, several alternative actuation mechanisms at the proximal end of the tool for actuating the distracting elements of the tool may be available. Additionally, several alternative implants may be available. For example, as shown in FIGS. 29 and 30, an implant 218 similar to that previously described is shown and includes a body 220 and a screw 222. The body 220 includes an upper 224 and lower 226 face joined together at a leading end 228 and separated from each other at a trailing end 230.

As shown in FIG. 29, when the screw 222 is not received in the body 220, the upper 224 and lower 226 faces may reside against each other such that the body 220 is generally flat. As shown in FIG. 30, when the screw 222 is received in the body 220, the upper 224 and lower 226 faces may be separated from each other, the degree of separation increasing as the screw 222 is increasingly received in the body 220. As the upper 224 and lower 226 faces are separated from each other, the body 220 takes on more of a wedge shape, with the leading end 228 being the narrow end of the wedge and the trailing end 230 being the wide end. The faces may include teeth 232 and the trailing end 230 of the upper face 224 may be formed to project towards the leading end, both of these features assisting in the implant 218 anchoring to the bone facet surfaces. Holes 234 may exist in the faces 224, 226 such that when the screw 222 is received in the body 220, the thread edges of the screw 222 may project through the holes 234 to bite into the facet surfaces. The wedge shape of the implant 218 may facilitate anchoring the implant 218 within the facet joint and may also facilitate distraction, translation, or subluxation of the facet surfaces relative to each other.

As can be understood from FIG. 29, the collapsed and flattened body 220 may be placed between the opposing surfaces of the facet joint. The posterior or trailing end 230 of the body 220 is configured to be capable of receiving a screw, bolt, or some other inserted component 222. As indicated in FIG. 30, upon insertion of the screw, bolt, etc. 222, the body 220 begins to expand. This expansion and separation is enabled by a hinge 236 at the anterior or leading end 228 of the body 220. As the body 220 expands, sharp directional teeth, cleats, or keels 232 on the opposing (superior & inferior) surfaces or faces 224, 226 of the body 220 may become anchored in the cortical bone of the opposing facet surfaces. These teeth, cleats, or keels 232 may engage the facet surfaces and provide acute fixation of the body 220 within the facet joint. The teeth, cleats, or keels 232 may be included on only one surface 224, 226 as opposed to both surfaces 224, 226 so as to allow for a movement of the joint after placement of the implant 218.

The distraction and separation of the facet joint via the expanded implant (see FIG. 30) may increase foraminal area and reduce the symptoms associated with nerve root compression.

Figure 31:
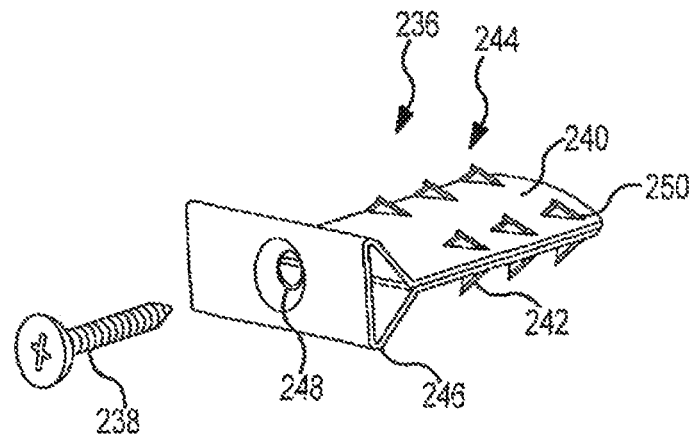
FIG. 31 is a perspective view of an implant in a collapsed position according to certain embodiments.
Figure 32:
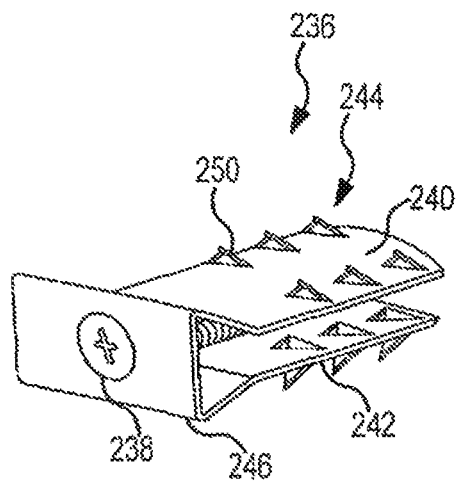
FIG. 32 is a perspective view of an expanded implant according to certain embodiments.

Another implant embodiment is depicted in FIGS. 31 and 32, wherein a screw 238 also acts to spread apart the faces 240, 242 of the body 244 of the implant 236. In this embodiment, the implant 236 may have an upper 240 and a lower 242 member positioned adjacent to each other. The upper 240 and lower 242 member may be substantially rectangular with a distal edge a proximal edge and parallel lateral edges. The distal edge may be slightly radiused. The upper 240 and lower 242 members may be connected along their distal edge by a connection member 246 in the form of a triangularly bent plate or other connection. The connection member may include a penetration 248 adapted to receive an implant distractor 238. As with the previous embodiments, the implant 236 may include teeth 250 on the outer surface of the upper member 240 or the lower member 242 or both as shown. In one embodiment, the implant 236 may be formed from a single plate and folded to create the shape shown. In use, the implant 236 may be positioned in a facet joint and the implant distractor 238 may be advanced thereby separating the upper 240 and lower 242 member and distracting the joint. Similar to that discussed above with respect to FIGS. 29 and 30, such an embodiment as depicted in FIGS. 31 and 32 may have holes (not shown in FIGS. 31 and 32) in the body surfaces 240, 242 so as to allow the threads of the implant distractor 238 to extend through the surfaces of the body 244 to bite into the facet surfaces.

Figure 33:
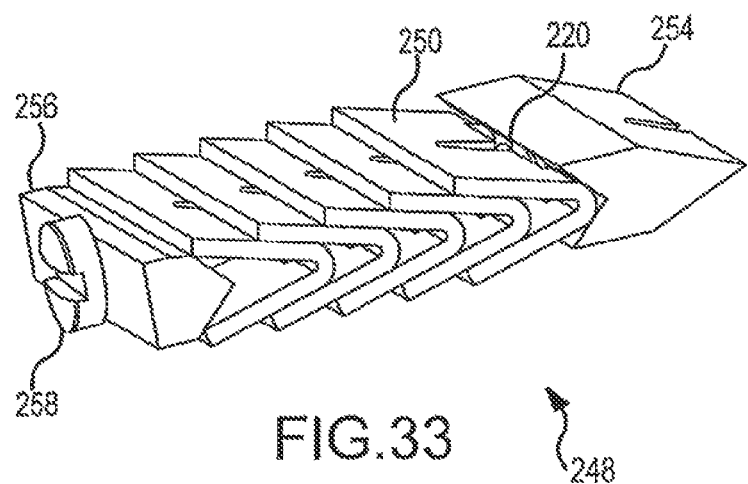
FIG. 33 is a perspective view of an implant in a collapsed position according to certain embodiments.
Figure 34:
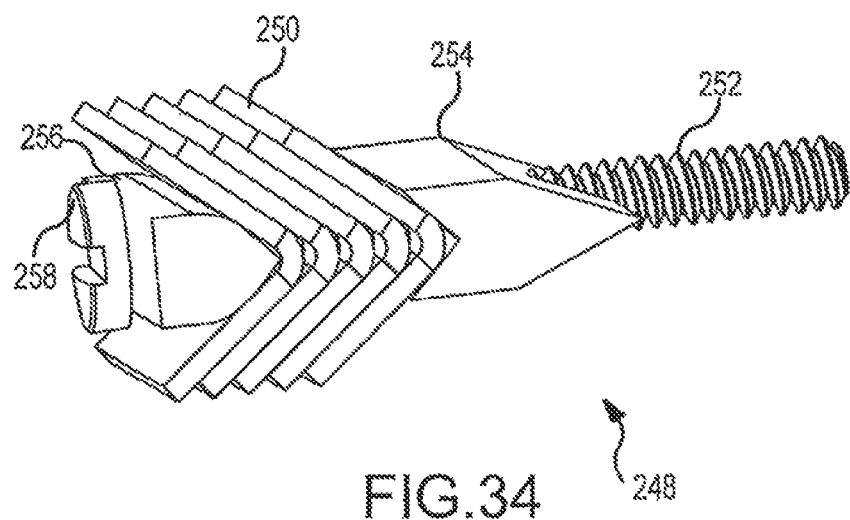
FIG. 34 is a perspective view of an expanded implant according to certain embodiments.

FIGS. 33 and 34 depict isometric views of another implant 248 with V-shaped members 250 residing on a threaded bolt 252 between an anterior threaded block 254 and a posterior non-threaded block 256. The V-shaped members 250 may slidably engage the bolt 252. As shown in FIG. 33, the V-shaped members 250 are in a non-expanded state and are spaced apart from each other along the length of the bolt 252. The implant 248 may be inserted into the facet joint in the non-expanded state depicted in FIG. 33. As can be understood from FIG. 34, the bolt 252 may be rotated to cause the anterior threaded block 254 to travel along the bolt 252 towards the posterior non-threaded block 256. It is noted that in use, the rotation of the blocks 254, 256 may be prevented by their position within a facet joint, thus causing the anterior threaded block 245 to travel rather than rotate when the bolt 252 is rotated. The posterior non-threaded block 256 may be in abutting position against the head 258 of the bolt 252 thereby preventing it from moving away from the anterior thread block 254. Thus, as the anterior threaded block 254 advances toward the posterior non-threaded block 256, the V-shaped members 250 are squeezed together. As the V-shaped members 250 are increasingly squeezed together between the blocks 254, 256, the V-shaped members 250 are increasingly expanded outward, thereby biting into the facet joint surfaces to anchor the implant 248 in the facet joint and distract, translate and/or subluxate the facet surfaces relative to each other.

Figure 35:
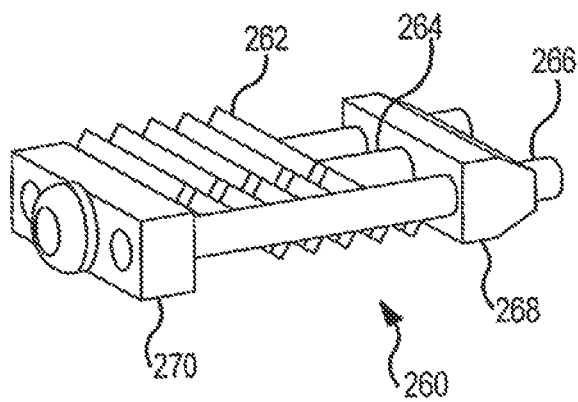
FIG. 35 is a perspective view of an implant in a collapsed position according to certain embodiments.

FIGS. 35-36 and 37A-D, depict isometric views of another implant 260 with planar plates or leaves 262 residing on a threaded bolt 264 and parallel shafts 266 between an anterior threaded block 268 and a posterior non-threaded block 270. As shown in FIG. 35, the planar plates 262 are in a skewed non-expanded state and are spaced apart from each other along the length of the bolt 264 such that may lie generally flat or, more specifically, at approximately 45 degrees on the bolt 264 and shafts 266. The plates 262 may include a slotted hole for receiving the bolt 264, which allows for the position described. The implant 260 may be inserted into the facet joint in the non-expanded state depicted in FIG. 35. As can be understood, the bolt 264 may then be rotated to cause the anterior threaded block 268 to travel along the bolt 264 towards the posterior non-threaded block 270, thereby causing the planar plates 262 to squeeze together. As the planar plates 262 are increasingly squeezed together between the blocks 268, 270, the planar plates 262 are increasingly expanded outward or, more specifically, are caused to be generally perpendicular to the bolt 264 and shafts 266. As a result, the planar plates 262 bite into the facet joint surfaces to anchor the implant 260 in the facet joint and distract, translate and/or subluxate the facet surfaces relative to each other.

Figure 36:
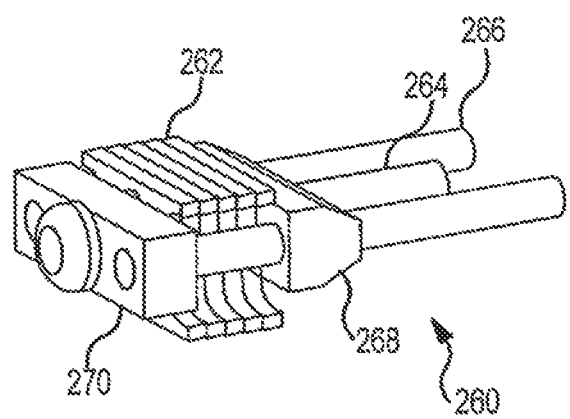
FIG. 36 is a perspective view of an expanded implant according to certain embodiments.
Figure 37A:
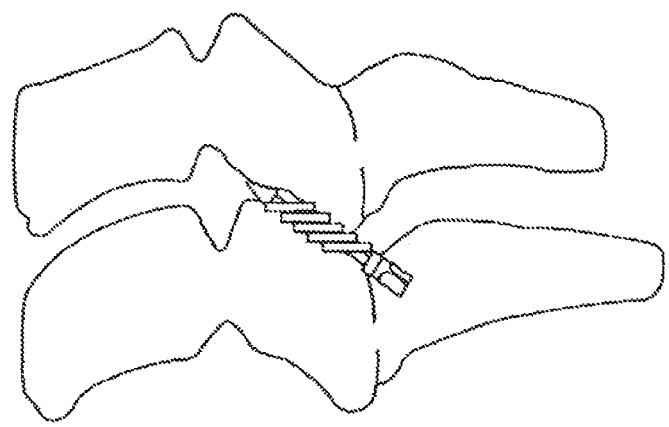
FIGS. 37A-D include side and perspective views of an implant, according to certain embodiments.
Figure 37B:
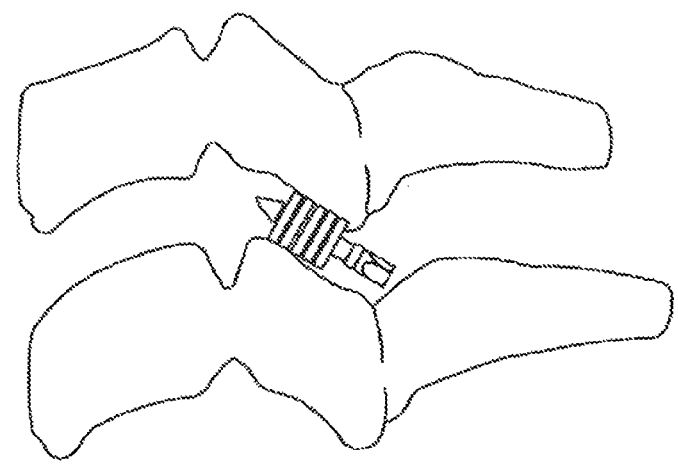
Figure 37C:
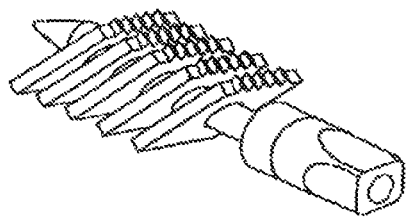
Figure 37D:
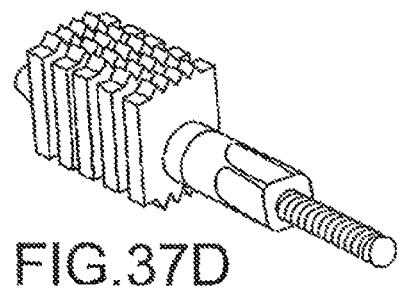

FIGS. 37A-D show an embodiment, which combines features of the embodiment shown in FIGS. 33 and 34 with features of the embodiment shown in FIGS. 35 and 36.

Figure 38A:
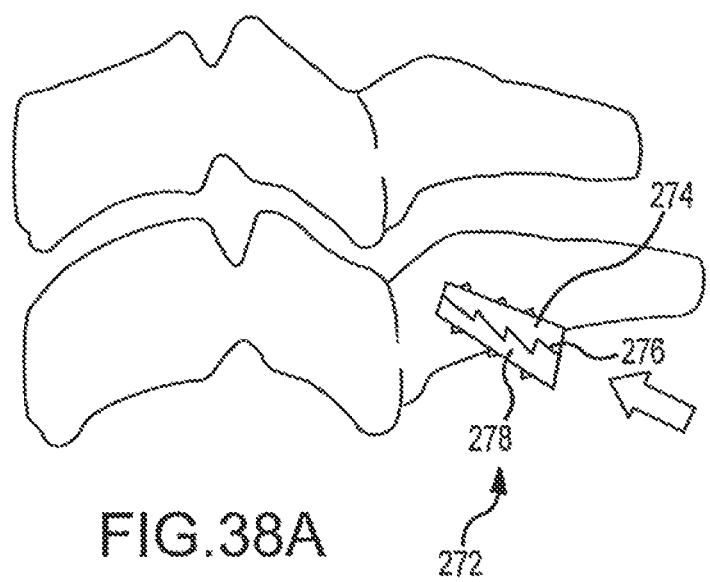
FIGS. 38A-C include side and perspective views of an implant, according to certain embodiments.
Figure 38B:
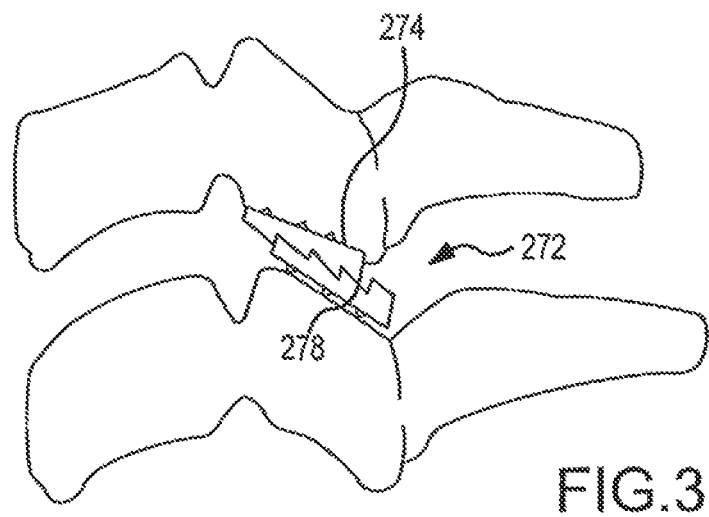
Figure 38C:
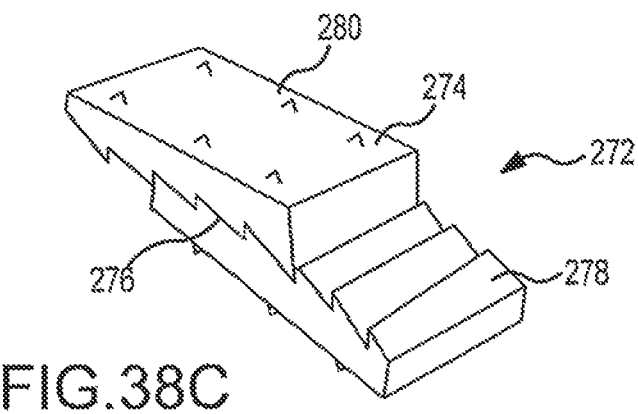

FIGS. 38A-C shows another embodiment of an implant 272. The implant 272 may include two stacked structures 274 that interface along a plane 276. Each structure 274 may include opposing ratchet teeth 278 along the plane. The position and orientation of the ratchet teeth 278 may be such that relative translation between the two structures 274 is allowed when a force is applied to each structure 274 in opposing directions. That is, once the implant 272 is properly positioned within the facet, a device may be use to apply a force to the superior structure 274 which causes forward translation of that structure 274 relative to the inferior structure 274. The ratchet teeth 278 on the superior structure 274 may slide up the slope of the teeth 278 on the inferior structure 274 until opposing apexes of teeth 278 pass by each other causing the two structures 274 to nest in a new relative position, the displacement being equal to the length of the teeth 278. Each structure 274, or only one of the structures 274, may increase in thickness along its length, such that continual relative ratcheted displacement creates a greater overall thickness. The increasing thickness of the implant structures 274 may cause distraction and forward translation in the facet joint. The opposing facet surfaces may be separated and the superior vertebra may be pushed anterior relative to the inferior vertebra. In addition, anchoring teeth 280 may be provided on the outer surface of both structures 274 of the implant 272 to provide acute fixation to the articular surfaces. The implant 272 may be configured in a number of different shapes including, but not limited to, a wedge, a double wedge, a rectangular box, and "v" shaped.

Figure 40A:
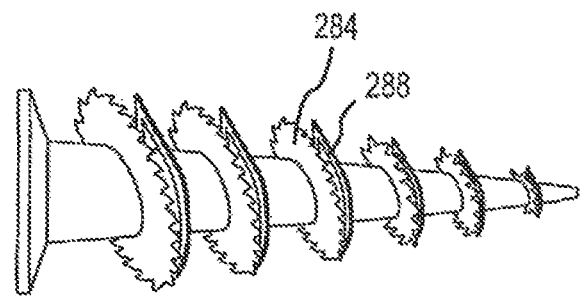
FIGS. 40A-C include side views of an implant, according to certain embodiments.
Figures 40B, 40C:
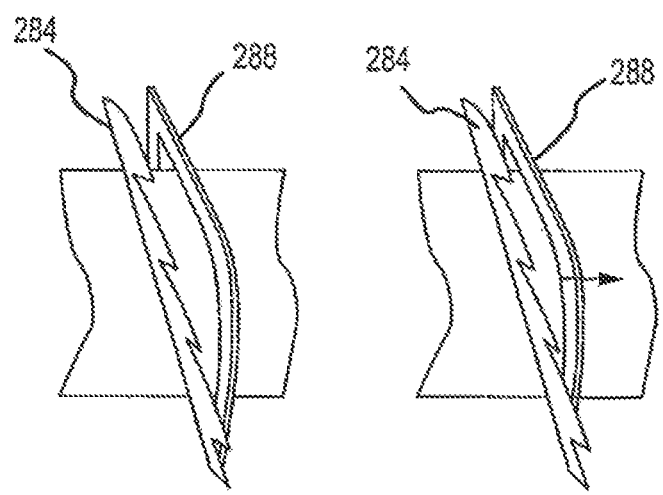

FIGS. 39A-D show another embodiment of an implant 282. In this embodiment, a screw like implant 282 may be inserted between the facet. The insertion of this screw may serve to distract the joint surfaces resulting in a decompression of the nerve root. Additionally, the threads 284 of the screw may include V-shaped notches 286 in the threads 284 spaced throughout the length of the screw creating serrated teeth. As the screw implant 282 is threaded progressively further anterior, the serrated teeth may cut/bore into the cortical bone of the opposing facet surfaces. The defect in the bone these serrations produce may prevent the implant 282 from backing out posteriorly or migrating medial/lateral because the threads 284 are configured with the serrated teeth to allow the implant 282 to catch or "bite" in the bone if any posterior withdraw or backing out occurs. Additionally or alternatively, as shown in FIGS. 40A-C, the screw threads 284 may include a leaf spring 288 to maintain friction of the threads 284 against the newly cut threads in the bone thereby preventing the screw from backing out.

Figure 41A:
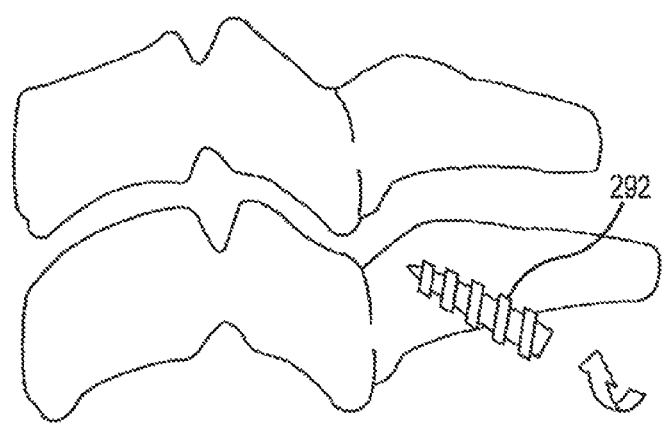
FIGS. 41A-D include side and perspective views of an implant, according to certain embodiments.
Figure 41B:
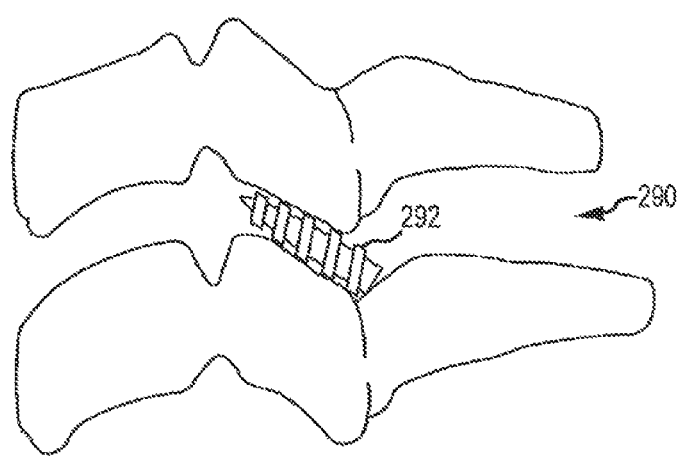
Figures 41C, 41D:
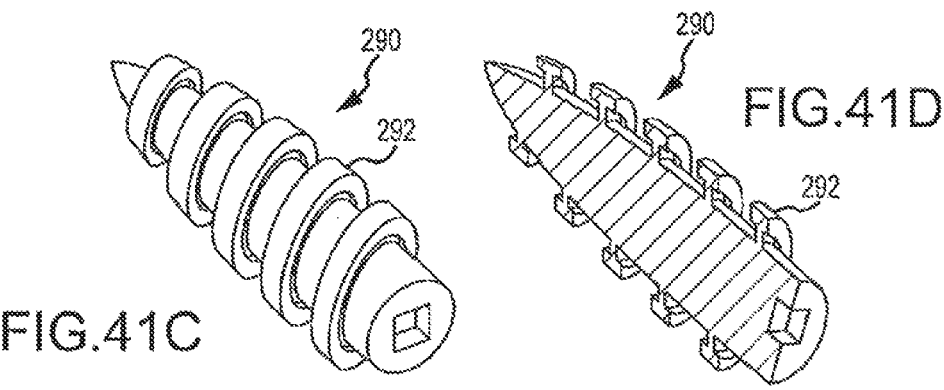

FIGS. 41A-D show another embodiment similar to the one shown in FIGS. 39A-D. That is, in this embodiment, the implant 290 may take the form of a screw, but the threads 292 of the screw may have a T-shaped profile as shown in FIG. 41D. In addition, the flat surface of the T-shaped profile may define a diameter at any given point along the length of the screw. In one embodiment, the diameter may increase over the length of the screw and not be limited to just the tip like a traditional screw. As such, when the implant 290 is placed, the more it is advanced into the facet joint, the more separation it creates.

FIGS. 42A-F show another embodiment of an implant 294. In this embodiment, the implant 294 may again take the form of screw. The screw may have a washer or extra broad head 296 with sharp protrusions 298 on the distal surface of the head 296 that engage the superior and inferior lateral mass surfaces as the screw is inserted into the facet joint. The engagement of the sharp protrusions 298 may occur as a result of both the longitudinal translation of the screw together with the rotational motion causing the sharp protrusions 298 to cut into the lateral mass surface as the screw is advanced and rotated. As the washer 296 rotates, the sharp protrusions 298 roughen the lateral masses and create a fracture environment. This fracture environment causes osteoblastic activity that will lead to bone production and assist in fusion of the joint at the lateral mass. Moreover, the moat created by the rotating and cutting protrusions 298 may begin to lock the facet surfaces together.

Figure 42A:
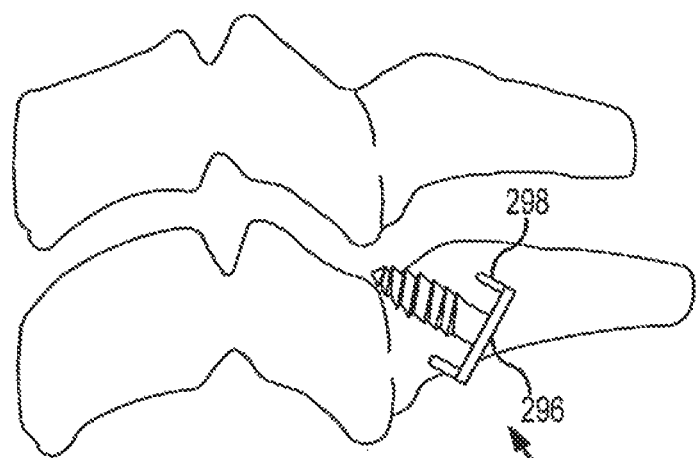
FIGS. 42A-F include side and perspective views of an implant, according to certain embodiments.
Figure 42B:
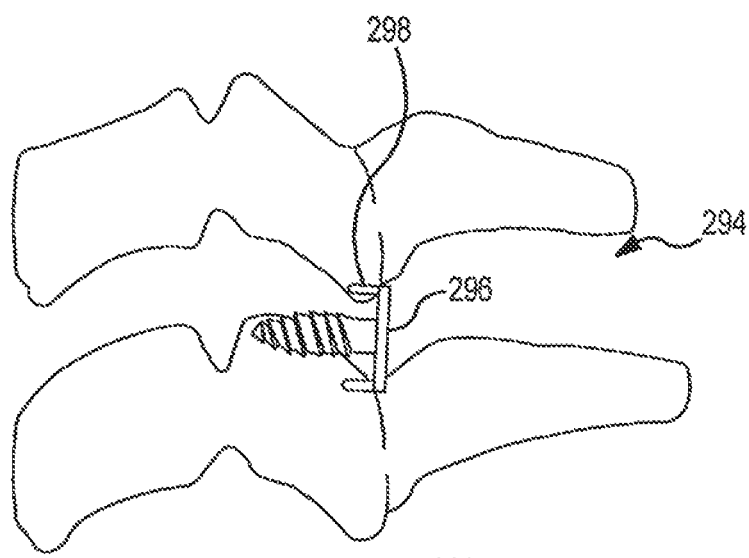
Figure 42C:
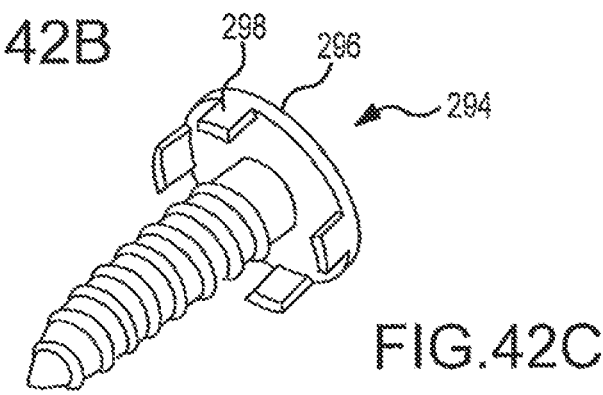
Figure 42D:
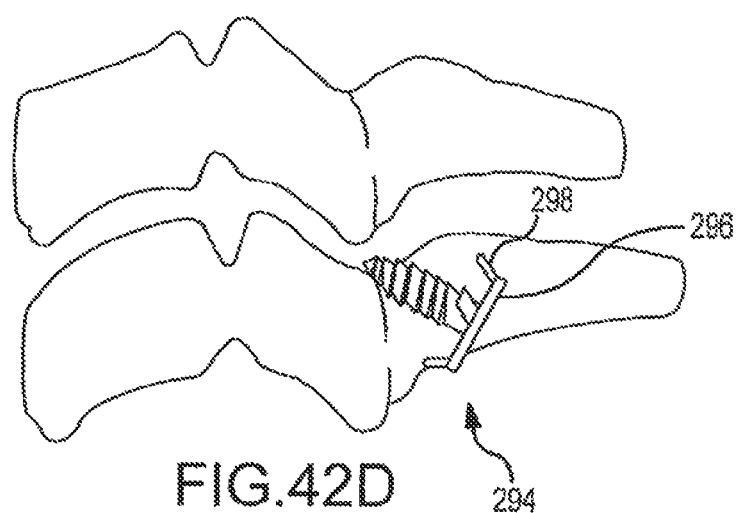
Figure 42E:
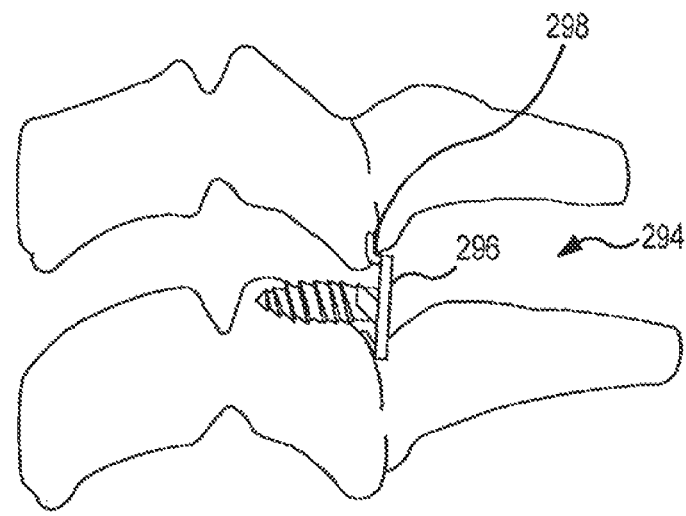
Figure 42F:
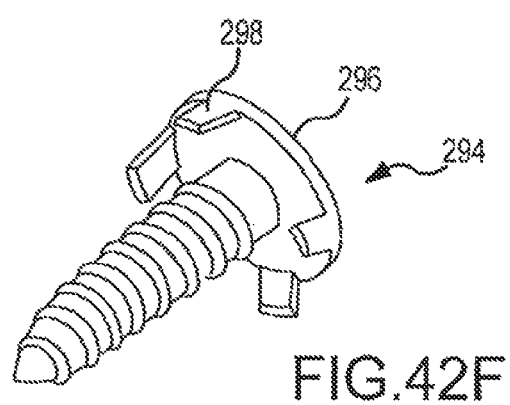
Figure 43A:
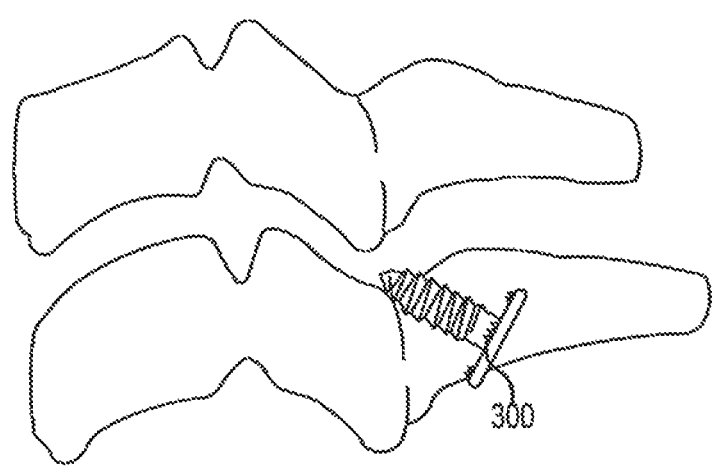
FIGS. 43A-C include side and perspective views of an implant, according to certain embodiments.
Figure 43B:
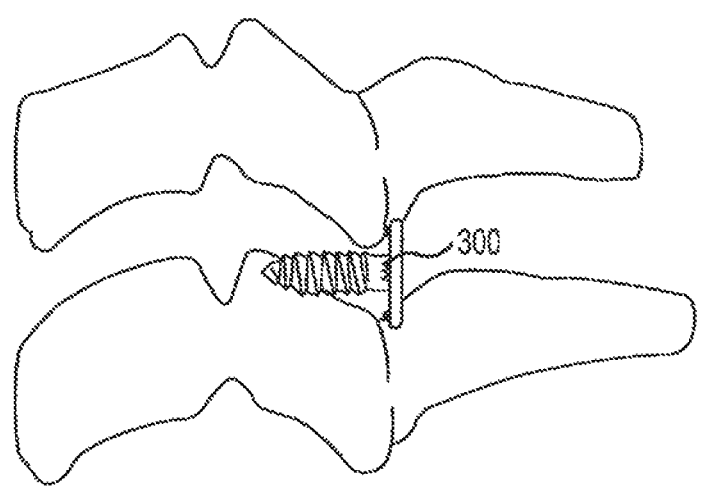
Figure 43C:
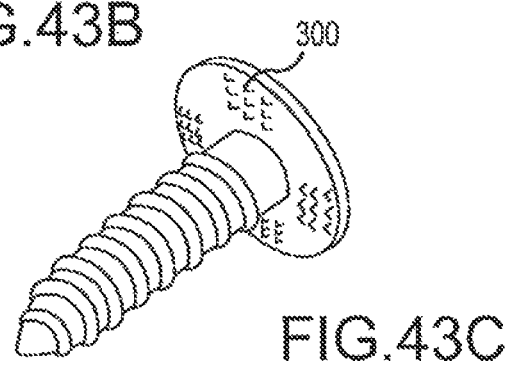
Figure 45A:
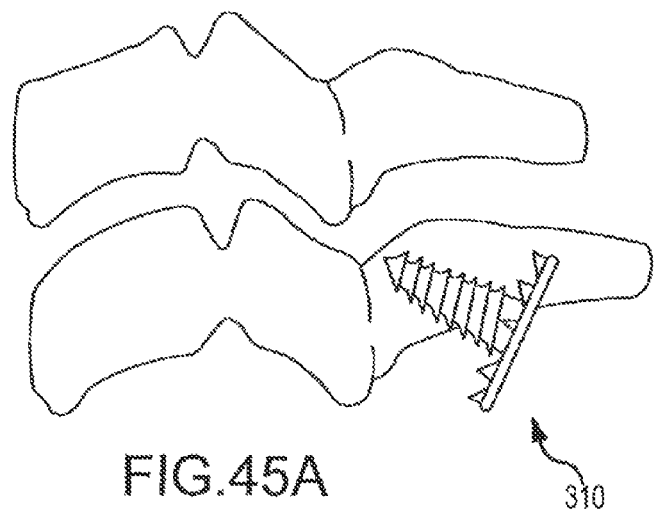
FIGS. 45A-D include side and perspective views of an implant, according to certain embodiments.
Figure 45B:
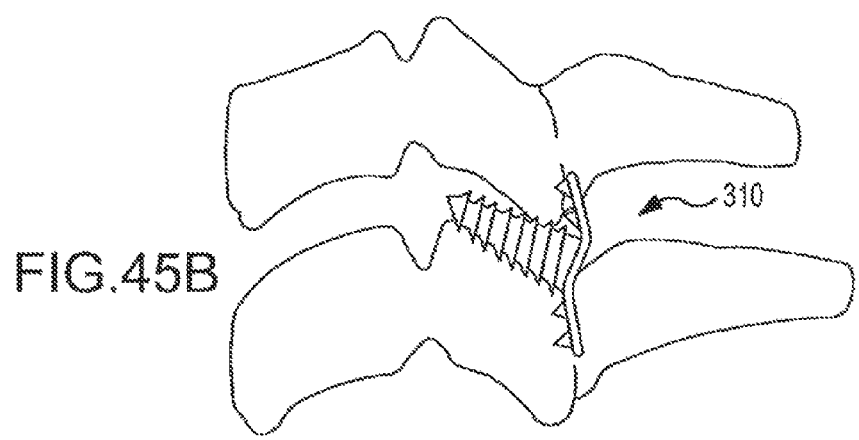
Figure 45C:
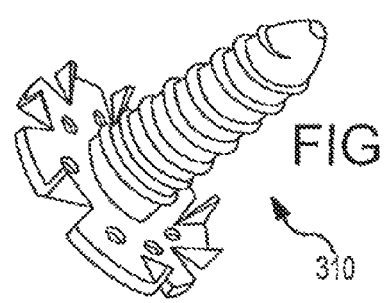
Figure 45D:
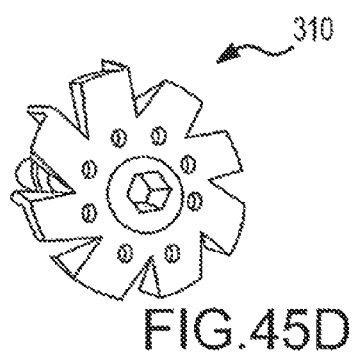
Figure 46A:
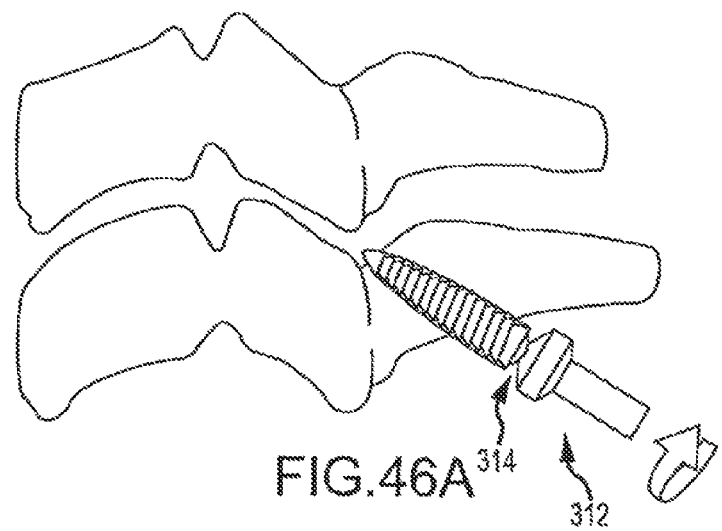
FIGS. 46A-D include side and perspective views of an implant, according to certain embodiments.
Figure 46B:
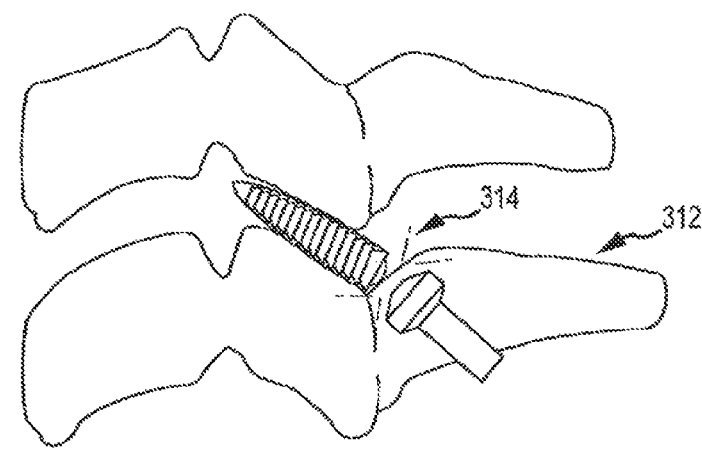
Figures 46C, 46D:
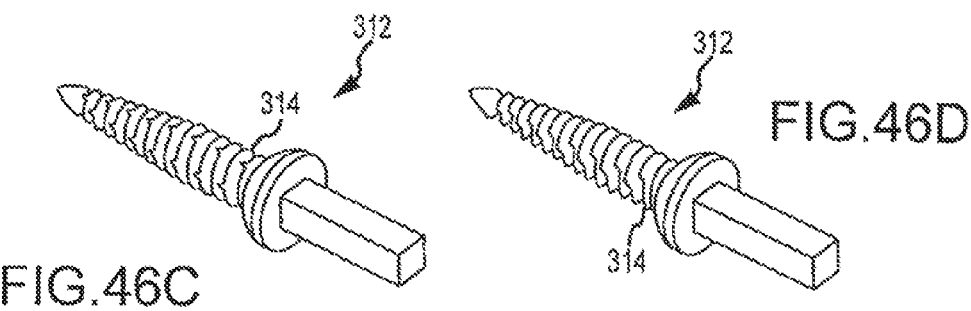

In the present embodiment, the protrusions 298 may be tab like and cut relatively deeply into the lateral mass. In addition as shown in FIGS. 42D-F, the tabs may position themselves as shown where the superior tab is flared to engage the lateral mass and the inferior tab is wedged into the joint. In this configuration, the tabs may act to further distract the joint beyond that provided by the diameter of the screw portion of the implant. In other embodiments, as shown in FIGS. 43A-C, the sharp protrusions 300 may be sharp prongs or spurs adapted to roughen the surface.

FIGS. 44A-D show another embodiment of an implant 302. In this embodiment, a facet distraction implant 302 has a floating collar 304 for use with a screw type implant. As shown, the collar 304 may be positioned to pivot about the head 306 of the screw due to the spherical shaped head 306 on the screw in a ball and socket fashion. The floating collar 304 allows the screw implant to accommodate irregular, non-planar surfaces of the lateral mass and may aid in the prevention of reverse threading of the implant 302 once the screw has been advanced to the proper position within the facet. As shown, the screw may be implanted to provide distraction and forward translation of the joint. The floating collar 304 may include teeth or spikes 308 that roughen/decorticate the cortical bone of the superior and inferior lateral masses resulting in the creation of a fracture environment. This may improve the chance of posterior lateral mass facet fusion.

FIGS. 45A-D show yet another embodiment of a decorticating screw type implant 310.

FIGS. 46A-D show another embodiment of an implant 312. In this embodiment, a structural implant 312 is inserted between the opposing surfaces of a facet joint. This implant 312 may be in the form of a screw as described above or may be a different implant requiring a torque or other force to be applied to anchor the implant 312 in the facet joint. As shown, when the implant 312 is inserted increasingly more anterior within the facet, a torque limiting mechanism 314 within the device may measure the force or torque applied to the system. Once a predetermined value of torque or force is achieved, the distal end of the system may detach causing the implant 312 to become a permanent distraction implant.

In the case of a screw implant, the torque limiting mechanism 314 may be a necked down portion of the device creating a calibrated weakened portion intended to fail when a specified torque is exceeded.

In this embodiment, the implant 312 may also include a number of anit migration features to prevent backout. These features may include directional teeth, roughened surfaces, keels, spikes, or other features known in the art. As with other implants, the geometry of the implant may cause distraction of the joint and lead to a more pronounced forward translation of the joint as the opposing facet surfaces separate.

Figure 47A:
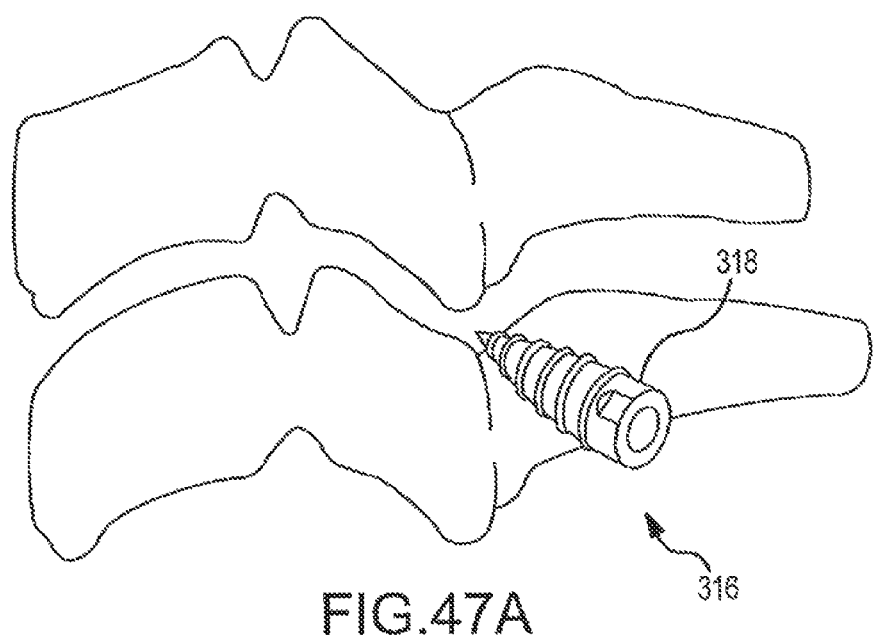
FIGS. 47A-B include side views of an implant, according to certain embodiments.
Figure 47B:
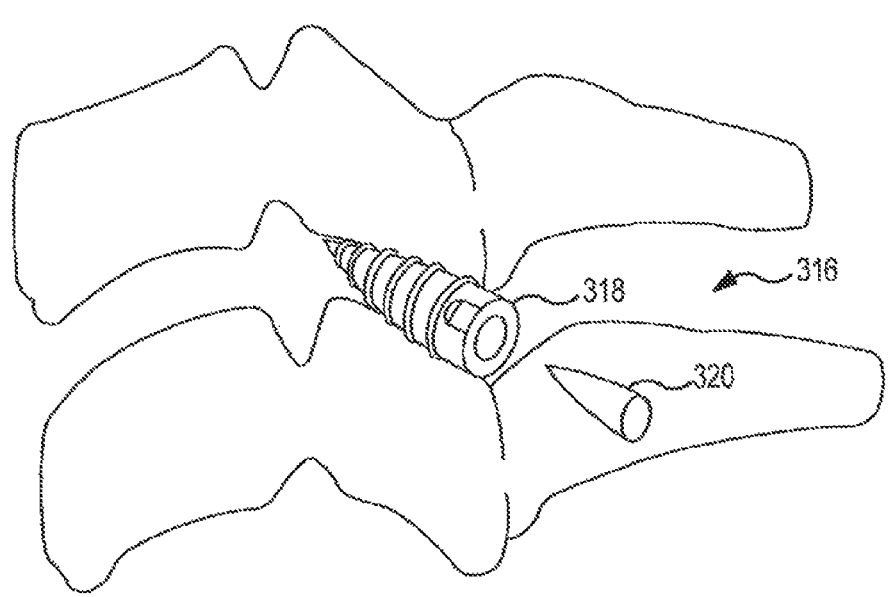

FIGS. 47A-B show another embodiment of an implant 316. In this embodiment, again a screw shaped implant 316 may be inserted into the facet to distract the facet surfaces and increase foraminal height resulting in a decompression of a symptomatic nerve root. In this embodiment, however, the implant may include two main components. First, the implant 316 may include a relatively stiff but malleable cone-shaped screw structure 318 with aggressive threads for biting into the opposing surfaces of the facet joint. These threads may have a number of variations for preventing movement of the implant after it is implanted. Second, the implant may include an inner core support member 320. The core support member 320 may be in place when the implant 316 is placed to assist in maintaining the shape of the screw structure 318. After placement, the core support member 320 may be removed. The malleability of the screw structure 318 may allow it to collapse slightly once the implant 316 is properly positioned and inserted. The collapsing of the screw structure 318 would change the alignment of the threads and prevent reverse threading that could lead to posterior migration.

Figure 48A:
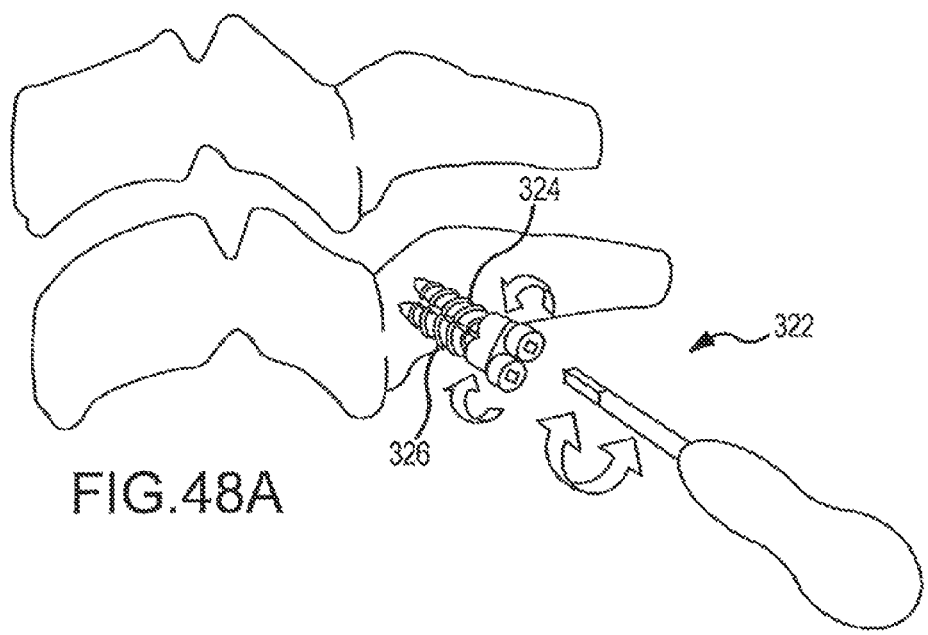
FIGS. 48A-C include side and end views of an implant, according to certain embodiments.
Figure 48B:
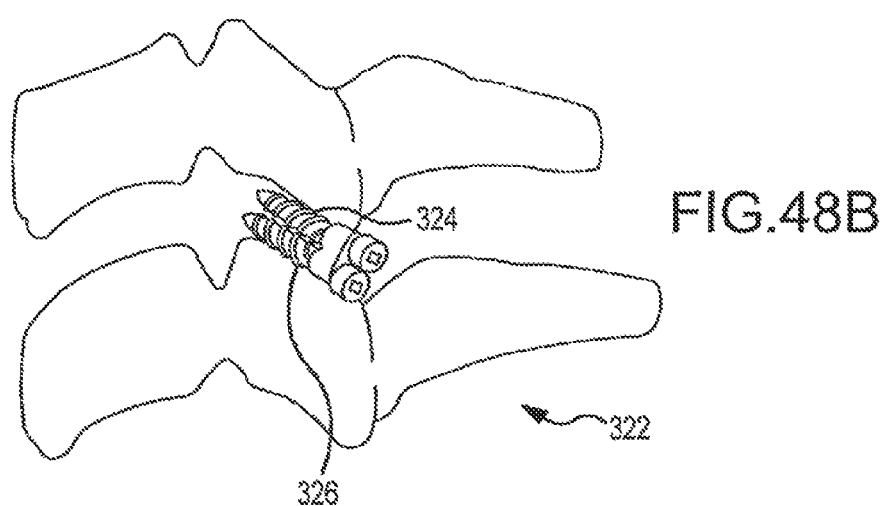
Figure 48C:
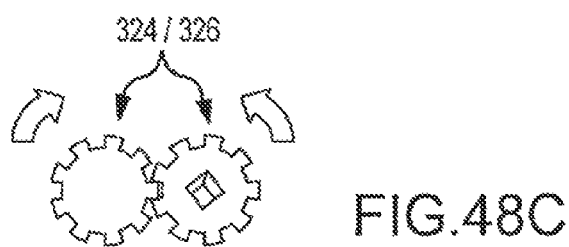

Yet another embodiment is show in FIGS. 48A-C. In this embodiment, a superior 324 and an inferior 326 screw may be used to create an implant 322. The two screws 324, 326 may have communicative threaded serrations that work in opposition to one another. As such, when the inferior screw 326 is rotated, the threads may interact with the superior screw 324 causing it to rotate in the opposite direction. Moreover, the threads on the inferior screw 326 and superior screw 324 are such that opposite direction rotation draws both screws 324, 326 in to the facet joint. As the screws 324, 326 enter the joint, the facet surfaces are distracted apart from one another and the threads of the screw bite into the facet surfaces. The opposing rotation of the two screws 324, 326 may also assist in preventing back out of the implant or reverse threading/unscrewing. It is noted that several configurations may be used to create the opposite rotation of the screws. In one embodiment, a housing may be placed over each screw allowing the screws to freely rotate relative to the housing, but securing the screws adjacent to one another. In this embodiment, the opposite rotation may occur due to the threads engaging with one another as described above or the screw heads may have gear teeth for engaging one another and causing opposite rotation. In another embodiment, the screws may have gears on them positioned within the housing to engage one another and cause opposite direction rotation.

Figure 49A:
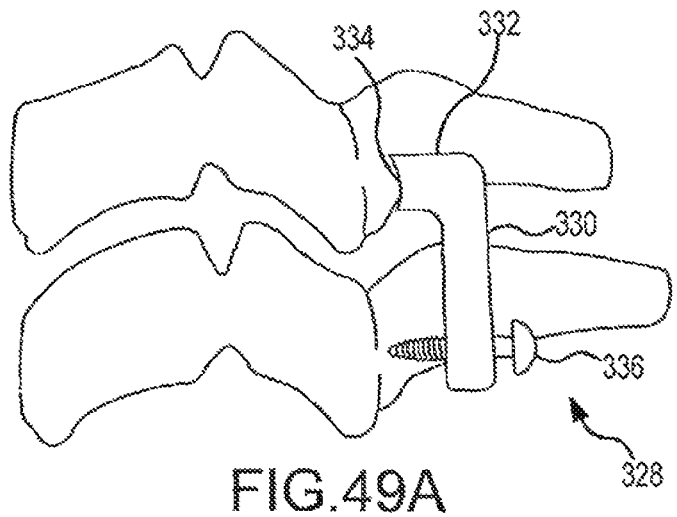
FIGS. 49A-C include side and perspective views of an implant, according to certain embodiments.
Figure 49B:
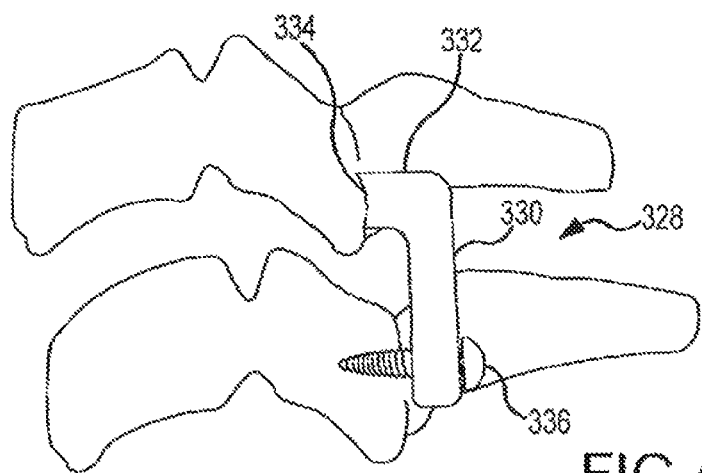
Figure 49C:
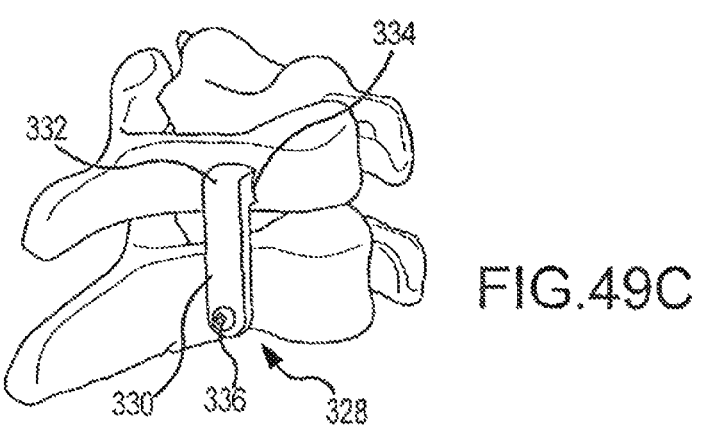

FIGS. 49A-C show yet another embodiment of an implant 328. In this embodiment, a translating system including a vertical plate 330 and a bumper 332 may be included. The superior aspect 334 of the bumper 332 may have a rounded concave surface for opposing the lateral mass of a superior vertebra. The translating system may be secured by anchoring a screw 336 to the lateral mass of an inferior vertebrae. The screw 336 may act as the foundation for a bumper system intended to push a superior vertebra forward (anterior) creating translation of the superior vertebra relative the inferior vertebra. This forward translation may create an increase in foraminal area and results in a decompression of the nerve root. The implant 328 may be configured to maintain permanent forward translation in order to prevent foraminal narrowing and nerve root compression. In addition, the implant 328 may provide rigid resistance when the superior vertebra exerts posterior translation vectors because it is anchored by the inferior lateral mass screw. The prevention of this posterior translation may keep the segment in a state of forward translation and preserve the associated increase in foraminal area.

Figure 50A:
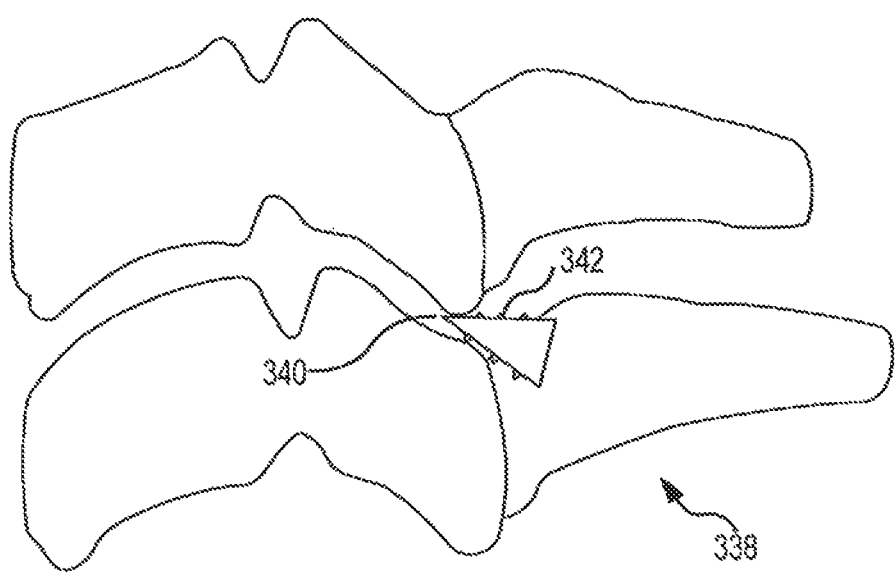
FIGS. 50A-B include side views of an implant, according to certain embodiments.
Figure 50B:
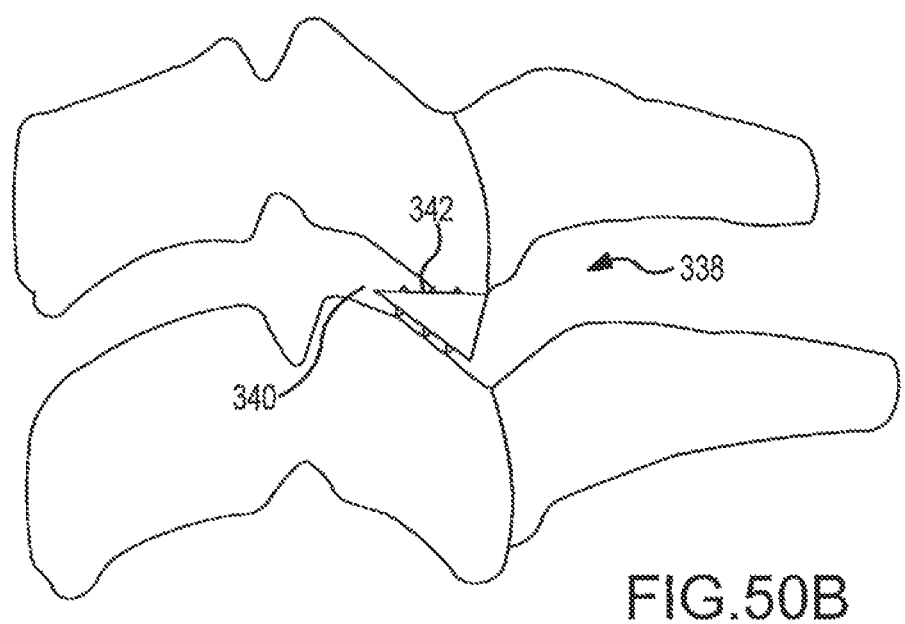

FIGS. 50A-B show another embodiment of an implant 338. In this embodiment, a wedge shaped or triangular implant 338 may be inserted between the face surfaces. The angled/pointed portion 340 with two acute line segments may allow the implant 338 to enter into the flat facet joint when sufficient force is applied. As the implant 338 is inserted progressively more anterior, the distraction of the opposing facet surfaces may increase. This separation results in an increase of foraminal height and decompresses the symptomatic nerve root.

Figure 51A:
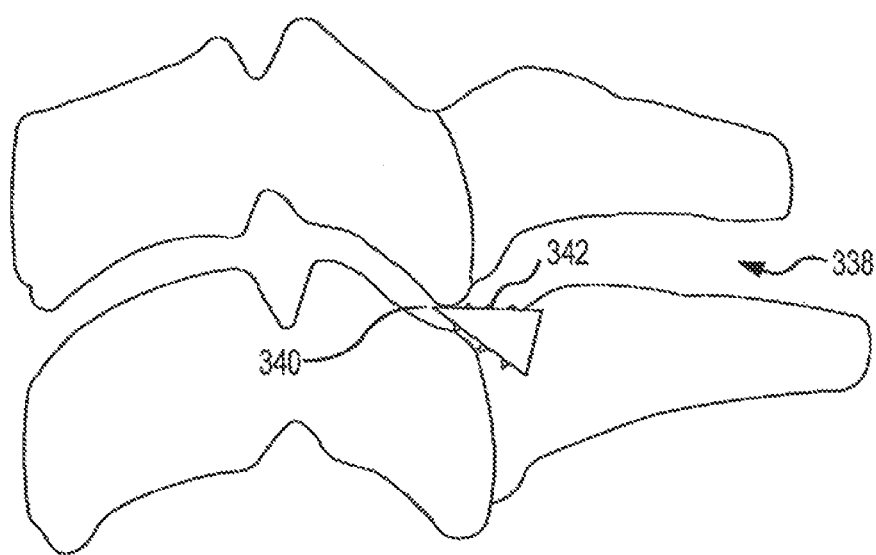
FIGS. 51A-B include side views of an implant, according to certain embodiments.
Figure 51B:
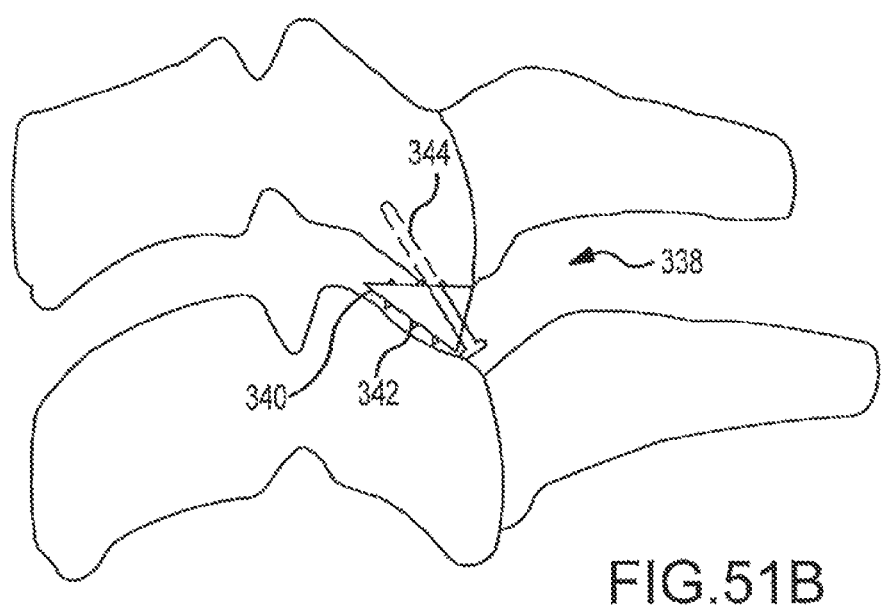

The surfaces of this implant 338 may include teeth, spikes, cleats, surface roughening, and/or keels 342 to help prevent migration or backout. In another configuration of this embodiment, as shown in FIGS. 51A-B, the wedge shaped or triangular implant 338 may be anchored in position by one or two (one shown in FIG.) lateral mass screws/nails 344 that would connect the superior & inferior aspects of the implant 338 to the corresponding superior & inferior lateral masses of the affected segment.

Figure 52A:
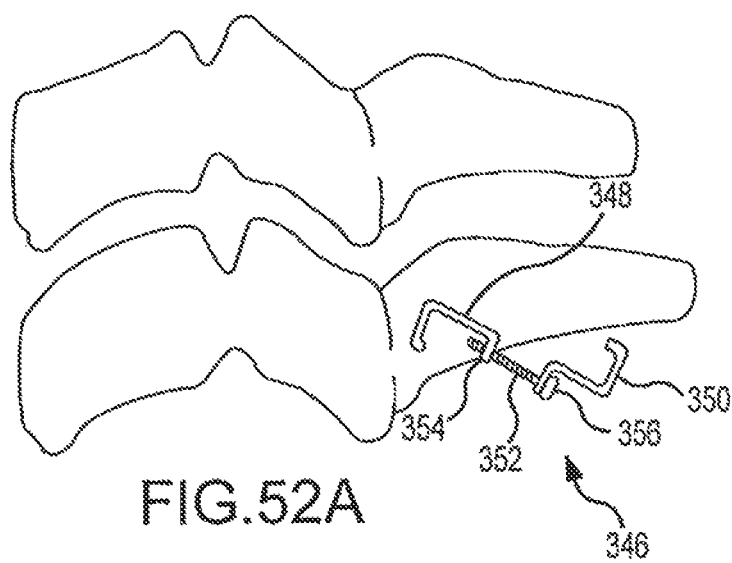
FIGS. 52A-C include side and perspective views of an implant, according to certain embodiments.
Figure 52B:
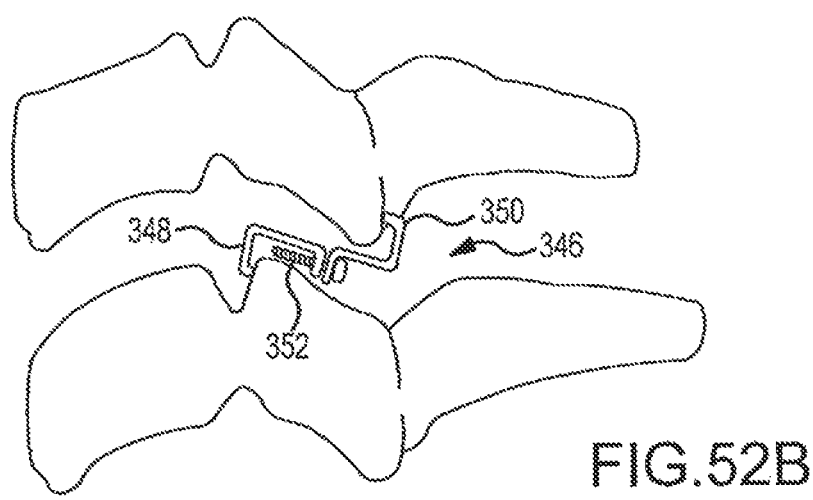
Figure 52C:
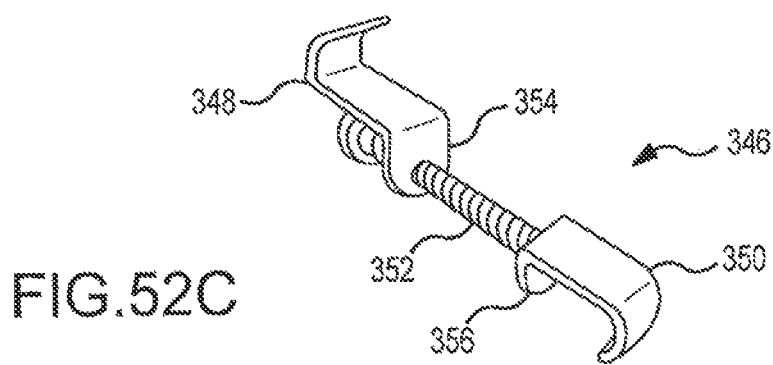

FIGS. 52A-C show another embodiment of an implant 346. In this embodiment, a distraction/translation system may include an anterior hook 348 and a posterior hook 350 joined by a threaded bolt 352. The anterior hook 348 may be placed over the anterior aspect of the inferior facet and the posterior hook 350 may be positioned posterior to the superior facet. The anterior hook 348 may have a C-shaped profile with a lip for engaging the anterior aspect of the inferior facet. The posterior hook 350 may have a S-shaped profile with a lip for engaging the posterior aspect of the superior facet. The threaded bolt 352 may be positioned through the facet joint and may threadably engage a posterior leg 354 of the anterior hook 348 and an anterior leg 356 of the posterior hook 350 as shown. As the bolt 352 is tightened and the hooks 348, 350 are drawn together, they create anterior translation of the superior vertebra relative to the inferior vertebra. This translation may result in increased foraminal area and nerve root decompression. The translation is maintained through the permanent placement of the hooks and bolt.

Figure 53A:
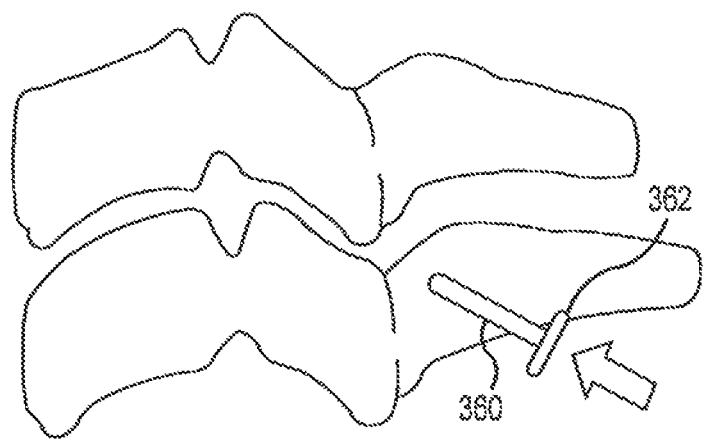
FIGS. 53A-C include side and perspective views of an implant, according to certain embodiments.
Figure 53B:
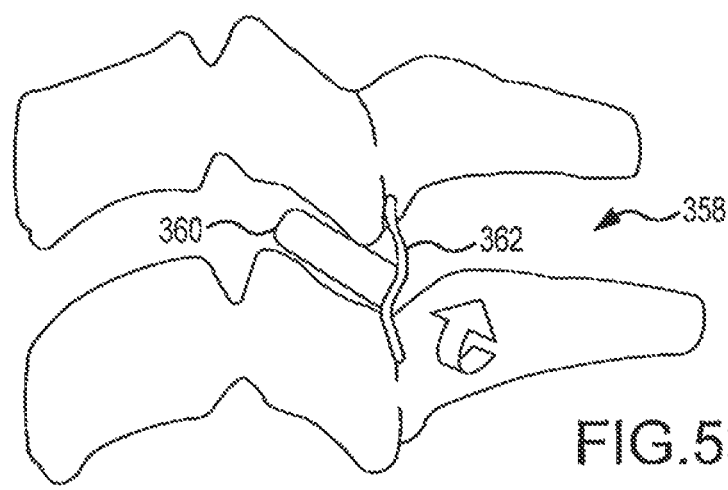
Figure 53C:
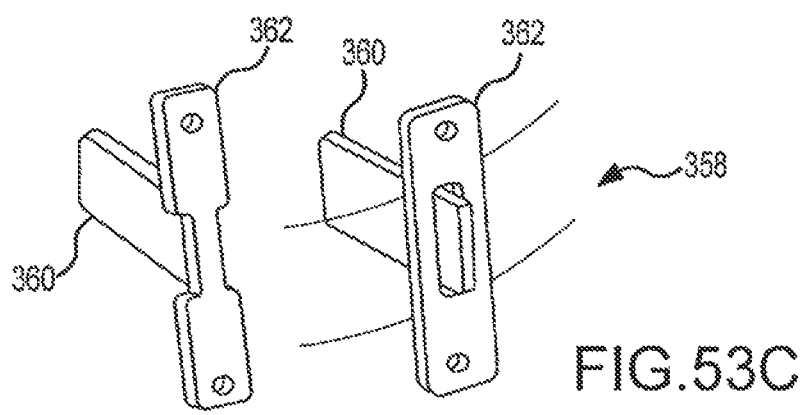

FIGS. 53A-C show another embodiment of an implant 358. In this embodiment, an insert 360 may be placed in the facet joint between two opposing facet surfaces. The geometry of the implant 358 could take a number of shapes including, but not limited to, rectangular, conical, triangular, or trapezoidal shape. Once the implant 358 is properly positioned, it may then be rotated some degree of rotation. This rotation may result in an increased height of the implant and cause facet surface separation and thus increased foraminal area and decompression of the symptomatic nerve root. In another configuration as shown in FIG. 53C, the rotated implant 358 may have outer tabs 362 that are capable of receiving a bone screw, nail, or pin that can be anchored in the superior and inferior lateral masses. These tabs 362 and anchors may assist in the prevention of implant migration leading to a reduction in the foraminal area.

Figure 54A:
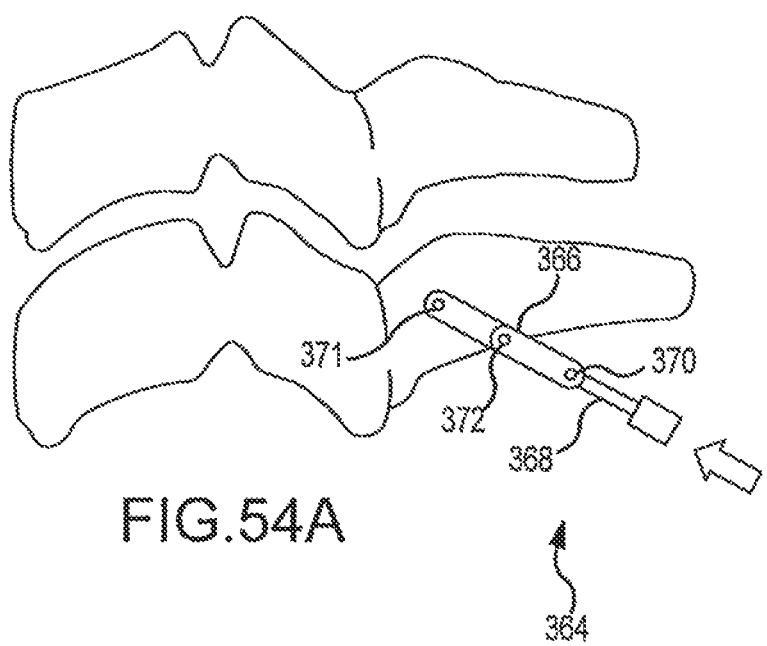
FIGS. 54A-C include side and perspective views of an implant, according to certain embodiments.
Figure 54B:
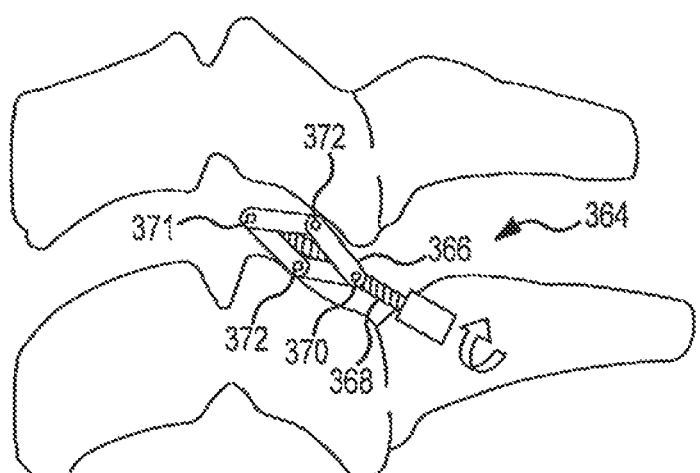
Figure 54C:
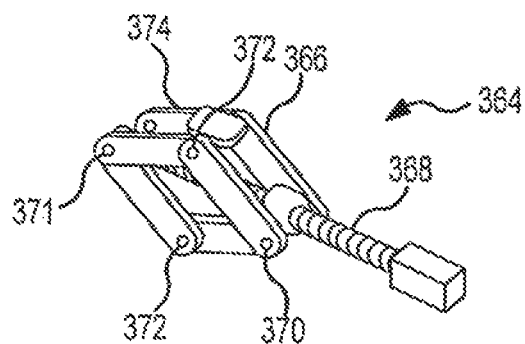

FIGS. 54A-C show another embodiment of an implant 364. In this embodiment, an implant 364 may take the form of a collapsible diamond shape 366 with an adjustment bolt 368 abutting a first corner 371 and threaded through an opposing corner 370 of the shape. The other corners 372 may include pads 374 for positioning against opposing articular faces of a facet joint. The implant 364 may be placed into the facet joint in a collapsed position and the adjustment bolt 368 may then be actuated to draw the opposing corners 371, 372 of the shape together thereby expanding the shape and pressing the pads 374 against the articular faces. As the shape expands, additional facet distraction is achieved resulting in an increased foraminal opening. This implant 364 may be provided in a number of geometries or materials to provide directional distraction where, for example, more distraction occurs near the posterior edge of the facet relative to the anterior edge of the facet. Additionally, the surface of the pad 374 may include teeth or keels to enable bone purchase in the facet.

Figure 55A:
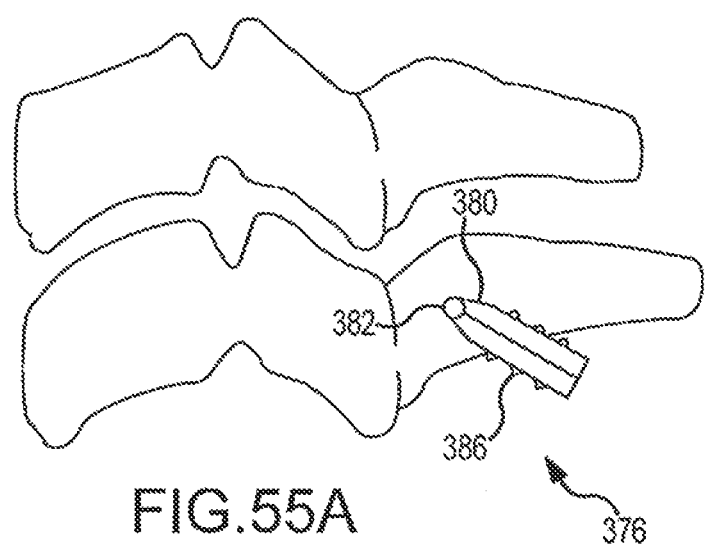
FIGS. 55A-C include side and perspective views of an implant, according to certain embodiments.
Figure 55B:
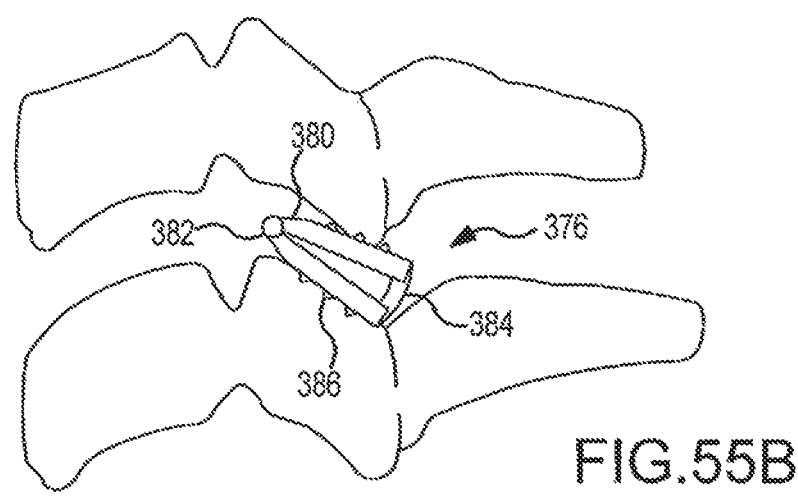
Figure 55C:
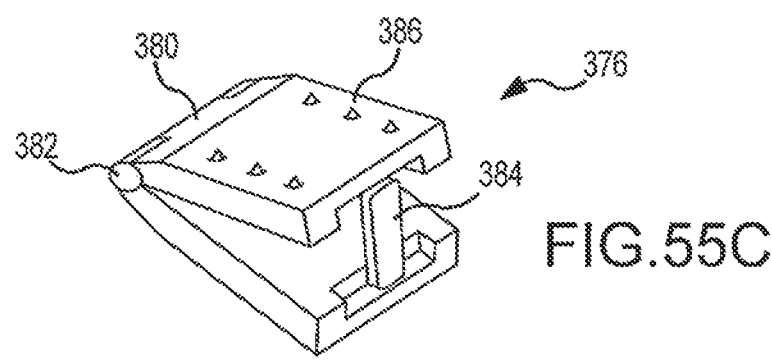

FIGS. 55A-C show another embodiment of an implant 376. In this embodiment, the implant 376 may take the form of an expandable hinged structure with an upper member 378 and a lower member 379 connected at their distal ends 380 by a hinge 382. The implant 376 may be placed between the facet surfaces in a collapsed state. The posterior aspect of the implant 376 may include a receiving slot that is able to receive a screw, bolt, or other activation system. Engaging this slot with an activator would cause the implant 376 to expand on its hinge 382 creating distraction and translation of the joint. For example, the activator may be a wedge, a turnable flat tool, a tapered screw, or any other device that may be inserted into the receiving slot to forcibly expand the upper 378 and lower 379 members. As shown, the hinge 382 may also include a brace member 384 for maintaining the posterior halves of the hinge in a separated position. The brace member 384 may be spring loaded or otherwise engaged with the hinge halves 378, 379 such that when expanded the brace 384 moves into position to support the open position of the hinge 382. In some embodiments, the upper 378 and lower 379 member of the implant 376 may have teeth, cleats, or keels 386 to engage the cortical bone of the opposing facet surfaces. These mechanisms would provide fixation of the implant 376 to the joint.

Figure 56A:
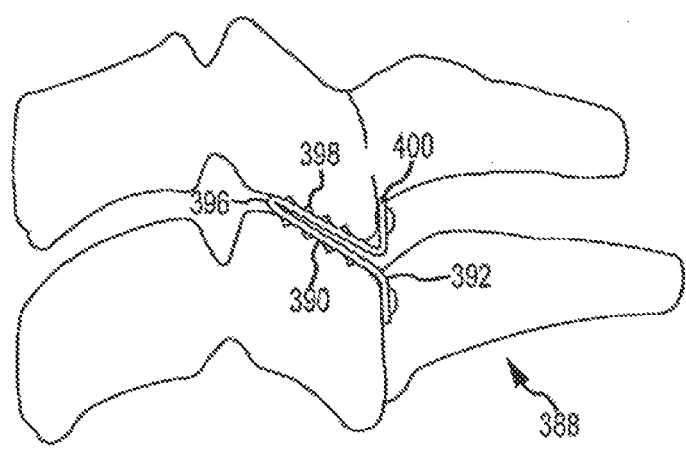
FIGS. 56A-C include side and perspective views of an implant, according to certain embodiments.
Figure 56B:
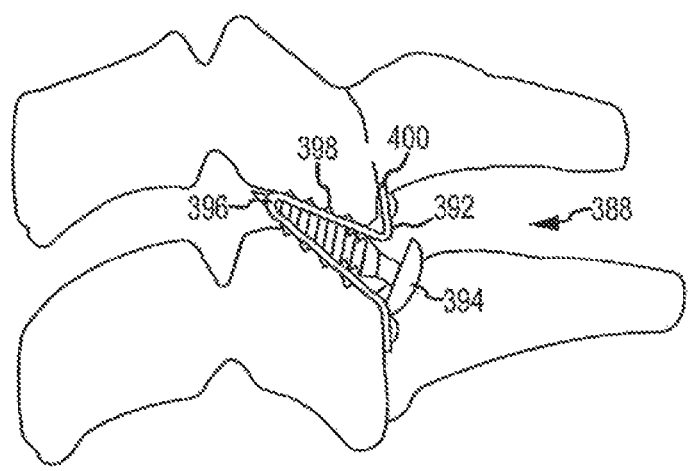
Figure 56C:
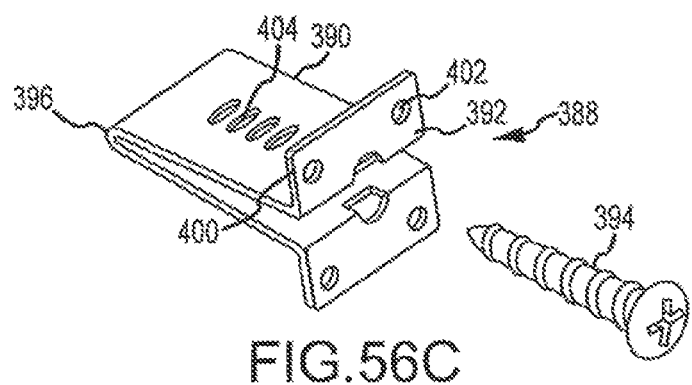

FIGS. 56A-C include another embodiment of an implant 388. In this embodiment, a collapsed and flattened structure 390 may be placed between the opposing surfaces of the facet joint. The posterior aspect 392 of the structure 390 may be configured to be capable of receiving a screw, bolt, or some other inserted component 394. Upon insertion of the screw, bolt, etc. 394, the structure may begin to expand. This expansion and separation may be enabled by a hinge 396 at the anterior aspects of the structure 390. As the structure 390 expands, sharp directional teeth, cleats, or keels 398 on the opposing (superior & inferior) surfaces of the structure may become anchored in the cortical bone of the opposing facet surfaces. These teeth, cleats, or keels 398 may engage the face surfaces and provide acute fixation of the structure within the facet joint. Together with the these teeth, cleats, or keels 398, or as an alternative to them, as shown, the proximal end of the implant 388 may also include flanges 400 that overlap the lateral mass of the facet joint. These flanges 400 may include holes 402 for anchoring the implant 388 to the superior and inferior facet masses, or to only one of the masses. In a related embodiment, the superior and inferior surfaces may have open ports 404 that enable the screw threads to exit the structure and gain purchase in the opposing facet surfaces. The distraction and separation of the joint may increase foraminal area and reduce the symptoms associated with nerve root compression.

FIGS. 57A-C show yet another embodiment of an implant 406. In this embodiment, the implant 406 may resemble a screw and wall anchor. The wall anchor portion 408 may be generally cylindrically shaped and include two half sections 410 separated by a slot or it may include a multitude of longitudinally extending sections 410. These sections 410 may be connected together at the tip 412 as shown or they may be connected together at the proximal end 414 of the implant 406 and at the tip 412 and may include several connections along the length of the implant 406. The implant 406 may have a sharp, triangular or conical tip 412 that allows for access into the flattened facet joint. Once the implant 406 is inserted into the facet surface, a screw, bolt, or other insertion component 416 may be inserted into the implant 406. As this component 416 is advanced the sections 410 may expand creating additional separation of the joint and allowing for measured distraction of the space. The sections 410 of the wall anchor portion 408 may include sharp directional teeth, cleats, or keels 418 that engage the cortical bone of the opposing facet surfaces.

Figure 58A:
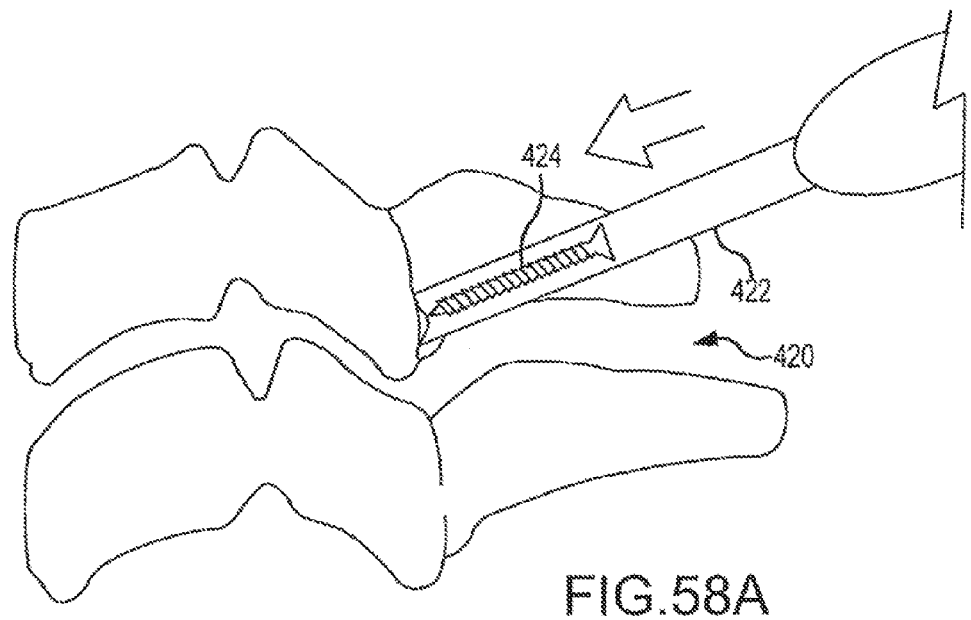
FIGS. 58A-B include side views of an implant, according to certain embodiments.
Figure 58B:
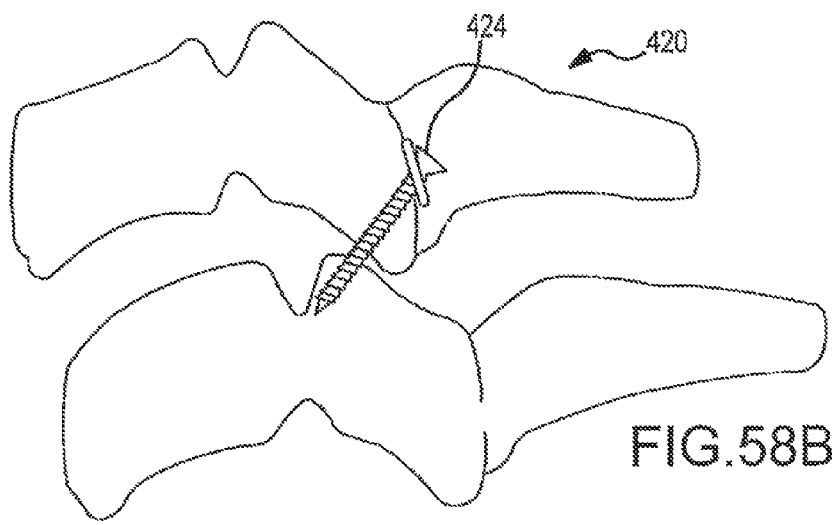

FIGS. 58A-B show yet another embodiment of an implant 420. In this embodiment, a tool 422 may be used to apply a force to the superior vertebra of a motion segment. This forward translation would result in an increase in foraminal area and reduced nerve root decompression. Following the forward translation of the motion segment, an angled screw 424 would be placed through the superior facet surface, facet capsule, and inferior facet surface. This screw 424 would provide temporary immobilization of the joint which leads to fusion.

Figure 59A:
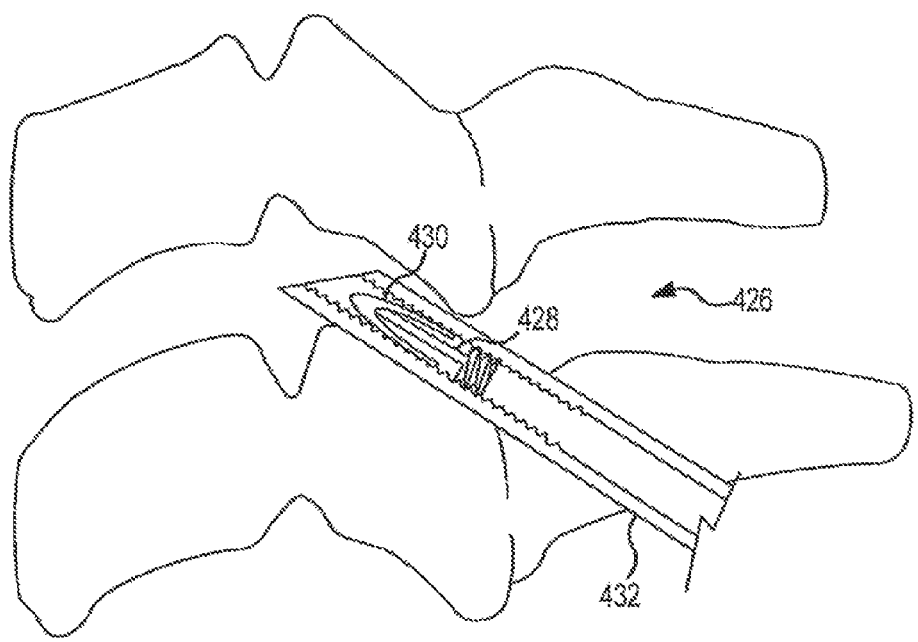
FIGS. 59A-B include side views of an implant, according to certain embodiments.
Figure 59B:
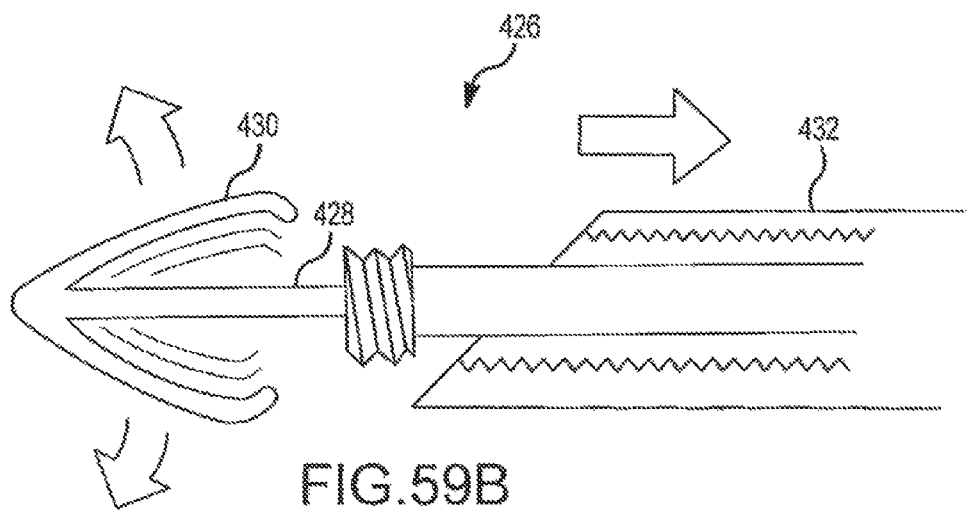

FIGS. 59A-B show yet another embodiment of an implant 426. In this embodiment, a collapsed, triangular shaped implant is inserted into the facet. The implant 426 may include a central shaft 428 and two or more springing leaves 430. The leaves 430 may be connected to the distal end of the shaft 428 and may extend proximally along the shaft 428. The leaves 430 may be connected at the distal end so as to be biased in a direction to form an arrow shape. The leaves 430 may be held in the compressed state by an insertion & delivery tool 432. The delivery tool's compression of the implant 426 prevents the superior and inferior surfaces of the implant 426 from springing open to a distracted position. Once the compressed implant 426 is positioned correctly, the delivery tool 432 may be removed. Removing the tools causes the leaves 430 to open/expand causing distraction and separation of the facet joint thus resulting in increased foraminal area and reduced nerve root compression.

Figure 60A:
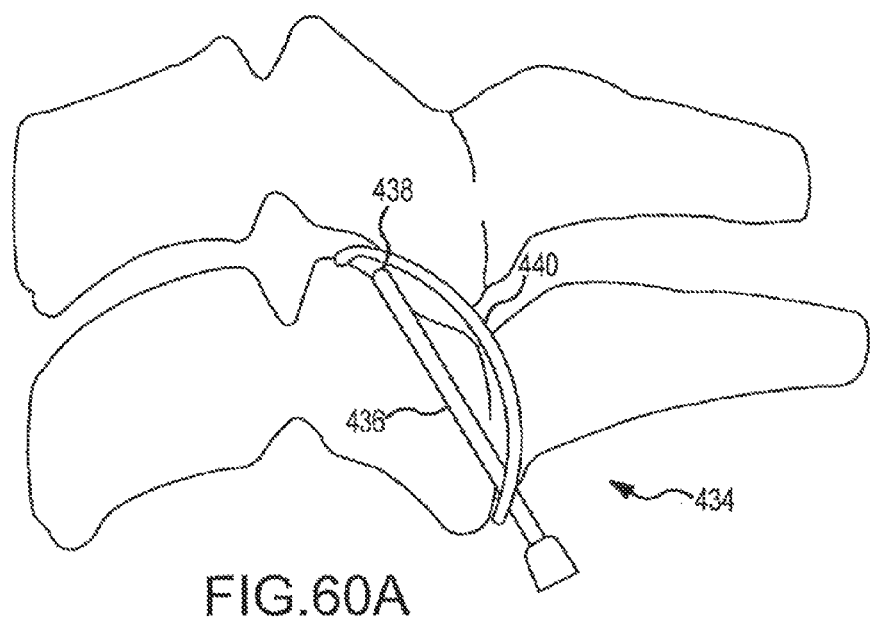
FIGS. 60A-B include side views of an implant, according to certain embodiments.
Figure 60B:
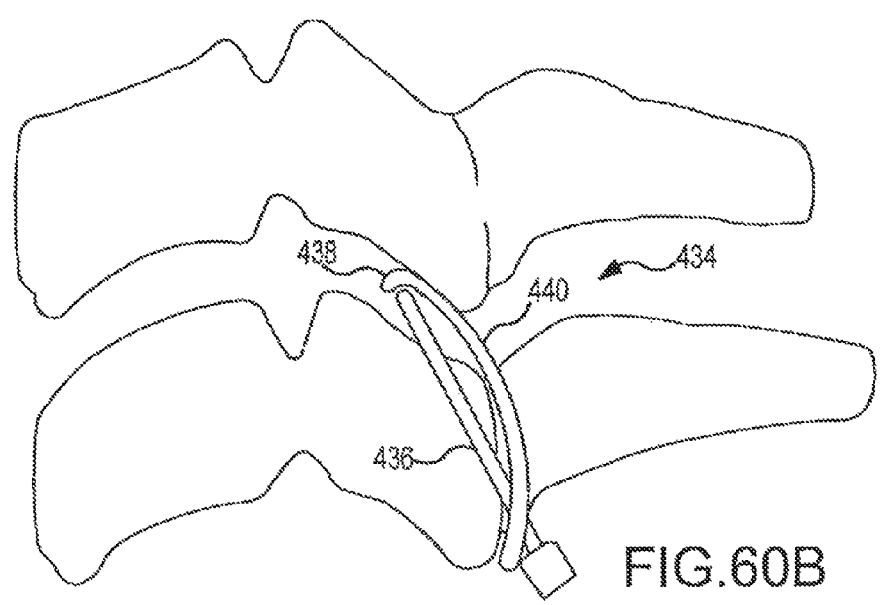

FIGS. 60A-B show yet another embodiment of an implant 434. This concept has at least three embodiments. The first embodiment consists of a direction facet joint screw 436 that is advanced through an inferior facet until it makes contact with the opposing superior facet. Once the screw 436 makes contact with superior facet surface, the energy applied to advance the screw 436 results in distraction and separation of the joint due to bearing of the screw tip 438 on the underside of the superior articular surface. In one variation of this embodiment, the hole for the screw in the inferior facet may be pre-drilled. When the screw is installed and encounters the superior facet, the screw may bite into the superior facet as it forces the fact upward and distracts the joint. Alternatively, in this embodiment, the screw may have a blunt tip 438 to distract the joint without biting into the superior facet.

In the second embodiment, as shown, a directional facet screw 436 may be advanced through the inferior facet surface until it engages with a facet spacer/plate 440 that is inserted in between the facet surfaces within the facet capsule. As the screw 436 makes contact with the facet spacer/plate 440, the flat surface of the spacer/plate 440 may push up against the opposing superior facet surface causes distraction and forward translation. This separation of the facet surfaces results in increased foraminal area and reduced nerve root compression.

In a third embodiment, the spacer/plate 440 may have a shape to allow the screw 436 to pass through a first end and the other end to be placed in the facet joint. In this embodiment, the C-shaped spacer 440 may be positioned in the joint, thereby slightly distracting the joint. The screw may then penetrate a first end of the spacer 440 thereby anchoring the spacer 440 in the joint. The screw may then be advanced through the inferior facet surface until it engages with the spacer/plate 440. As the screw 436 makes contact with the facet spacer/plate 440, the flat surface of the spacer/plate 440 may push up against the opposing superior facet surface causes distraction and forward translation. In some embodiments, the screw may penetrate the spacer and aid in fixing the joint.

Figure 61A:
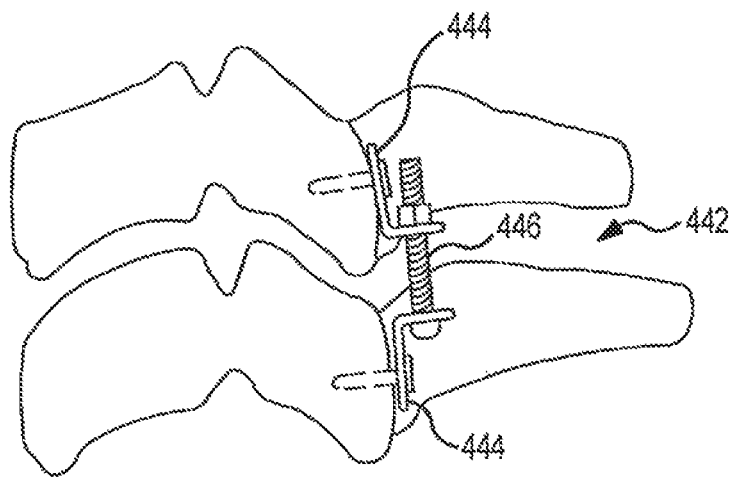
FIGS. 61A-C include side and perspective views of an implant, according to certain embodiments.
Figure 61B:
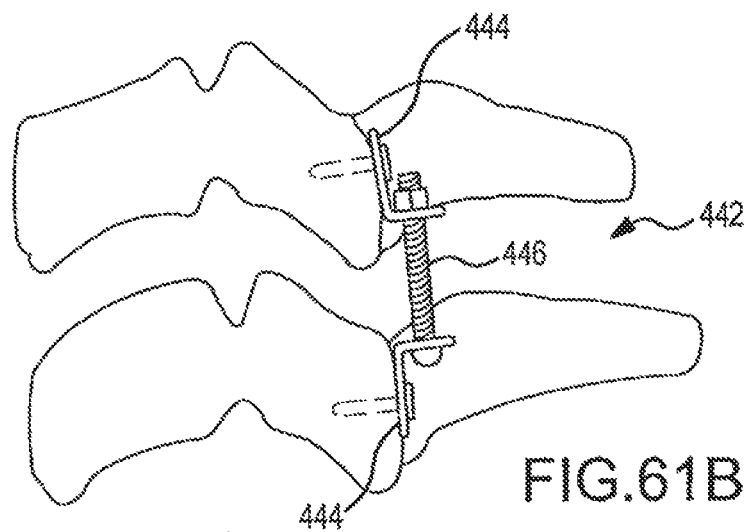
Figure 61C:
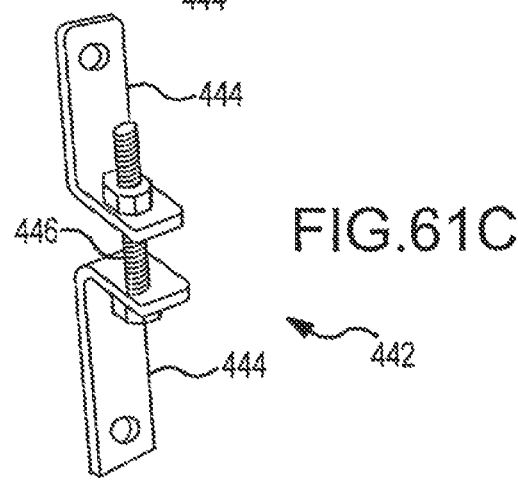

FIGS. 61A-C show yet another embodiment of an implant 442. In this embodiment, bracket type structures 444 may be attached to the superior and inferior lateral masses. The bracket type structures 444 may enable the attachment of a single bolt 446. The bolt 446 may be configured to create a distraction energy. That is, it may be connected to the inferior bracket 444 to allow rotation but not relative translation. In contrast, the bolt may threadably engage the superior bracket 444. As such, when the bolt 446 is "unscrewed" it may function to push the inferior and superior brackets 444 apart. This distraction may result in increased foraminal area and reduction in nerve root compression.

Figure 62A:
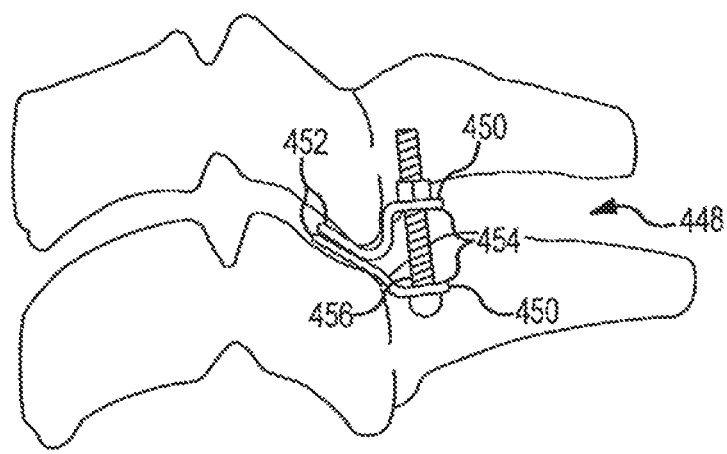
FIGS. 62A-C include side and perspective views of an implant, according to certain embodiments.
Figure 62B:
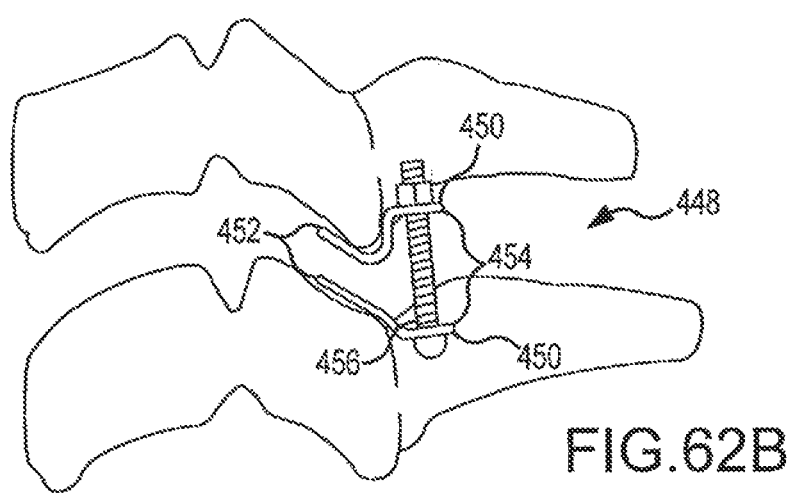
Figure 62C:
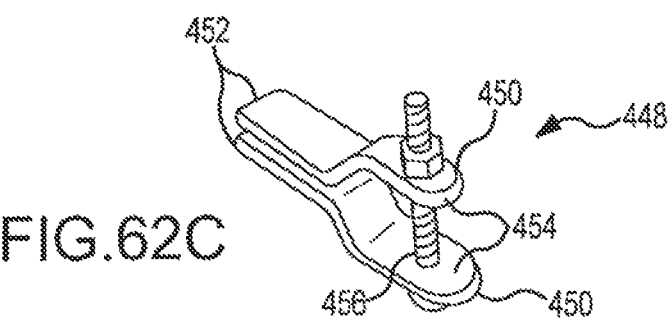

FIGS. 62A-C show yet another embodiment of an implant 448. In this embodiment, bracket type structures 450 may each have a leg 452 for positioning within a facet joint and another leg 454 for receiving a bolt 456. As with the bracket above, the bolt 456 may be configured to create distraction energy. That is, it may be connected to one of the superior or inferior bracket 450 so as to allow rotation but not relative translation. The other bracket 450 may threadably engage the bolt 456. As such, when the bolt 456 is "unscrewed" it may function to push the brackets apart resulting in and increased foraminal area.

Figure 63A:
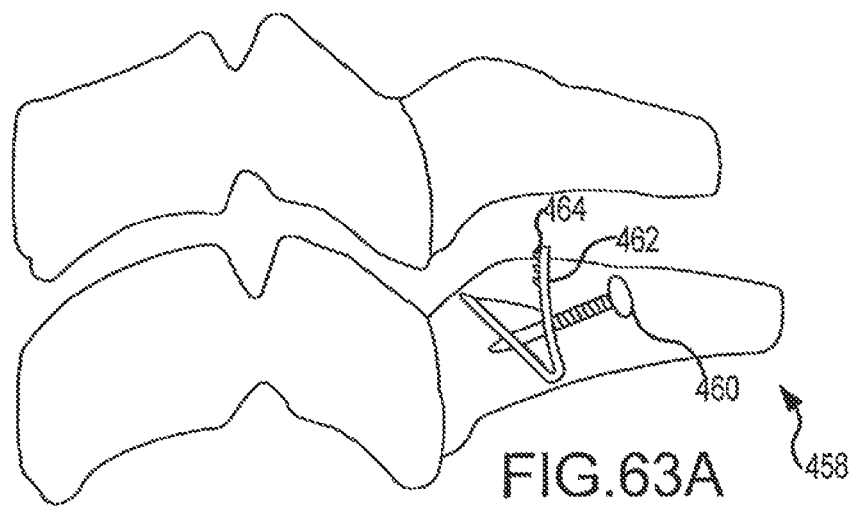
FIGS. 63A-C include side and perspective views of an implant, according to certain embodiments.
Figure 63B:
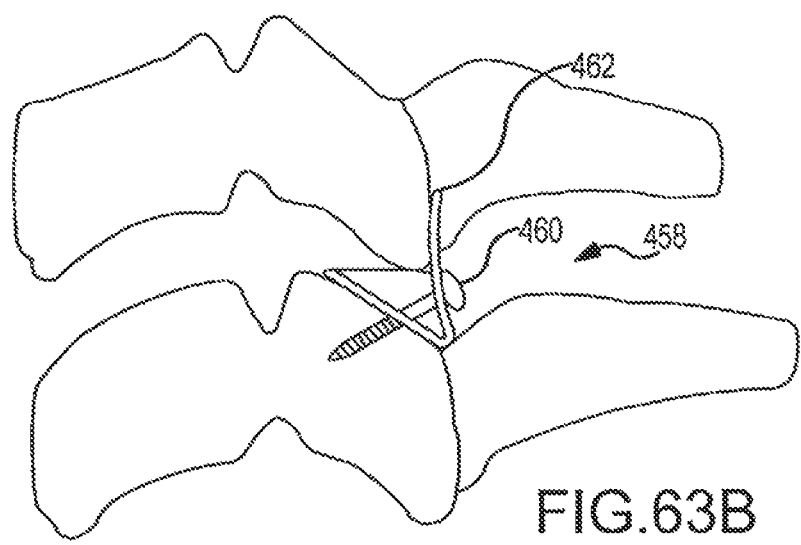
Figure 63C:
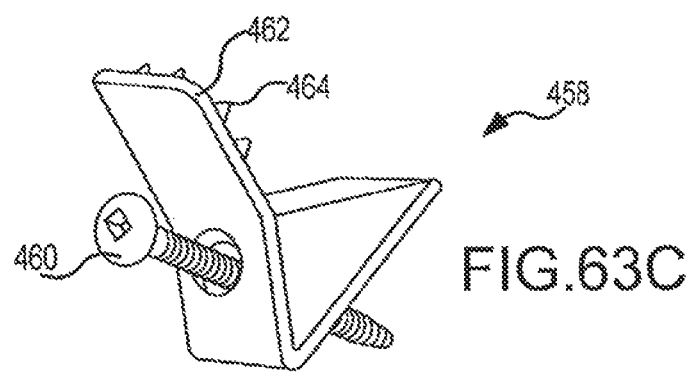

FIGS. 63A-C show yet another embodiment of an implant 458. In this embodiment, a triangular shaped implant 458 including a bent plate and a filler wedge may be inserted in the facet joint. As the triangular implant 458 is inserted progressively more anterior, the joint may be distracted to an optimal level. Once the desired distraction is achieved, an anchoring screw 460 may be inserted through the implant 458 and into the inferior lateral mass. The superior aspect of the implant 458 may include a metal flap 462 with teeth, spikes, or cleats 464. This malleable flap 462 may be contoured to the superior lateral mass and anchored using its teeth, spikes, or cleats 464. The metal flap 462 and inferior screw 460 may provide permanent fixation of the triangular implant 458 to enable permanent distraction of the facet and immobilization of the joint facilitating permanent fusion of the joint.

Figure 64A:
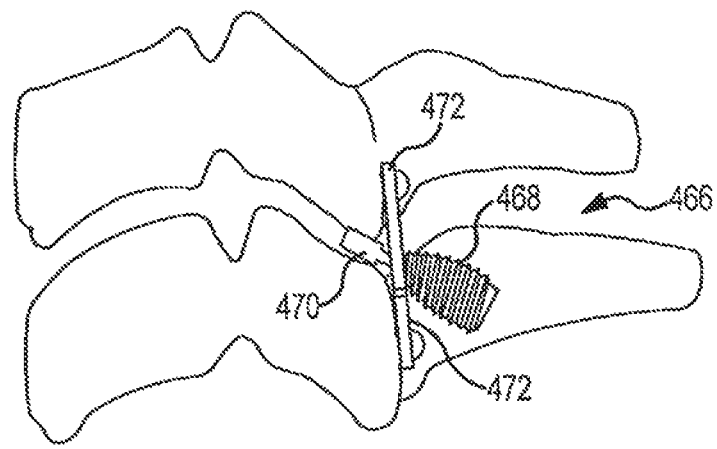
FIGS. 64A-C include side and perspective views of an implant, according to certain embodiments.
Figure 64B:
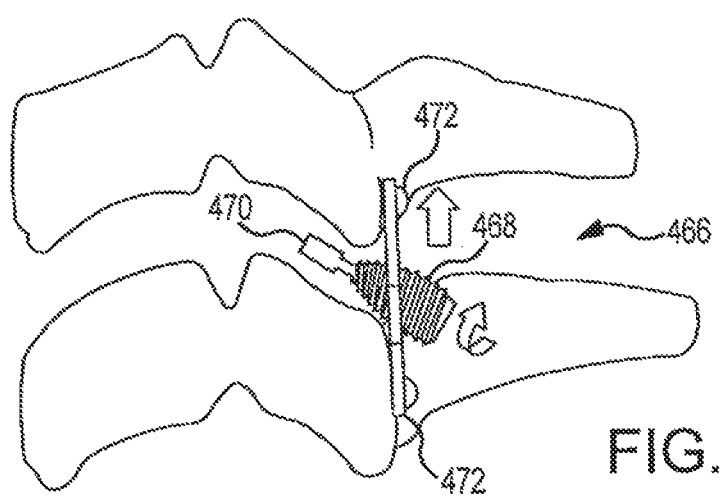
Figure 64C:
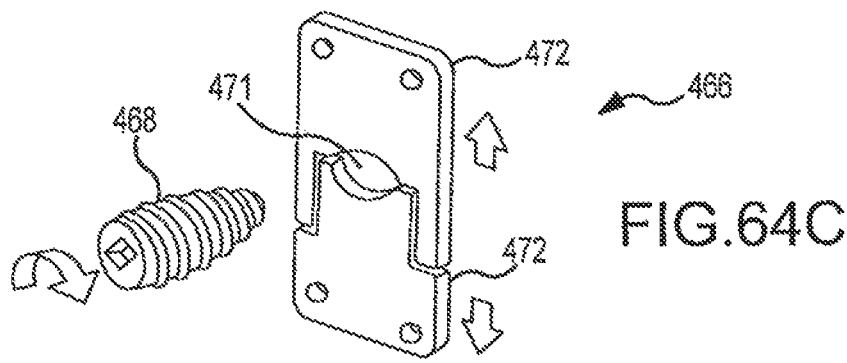

FIGS. 64A-C show yet another embodiment of an implant 466. In this embodiment, a distraction system consists of a central anchoring plug 468, an initiating plate 470, and two external plates 472. The two external (superior and inferior) plates 472 may be attached to the lateral masses of a motion segment and may be anchored using screws. The initiating plate 470 may then be inserted in the gap 471 between the external plates 472 to initiate opening of the plates 472 and the joint and allow for further insertion of the anchoring plug 468. Following the insertion of this initiating plate 470 and turning or manipulating the plate 470 to open the external plates 472, the central anchoring plug 468 may then be advanced into the gap 471 between the external plates 472 causing expansion of the plates and distraction and separation of the joint.

Figure 65A:
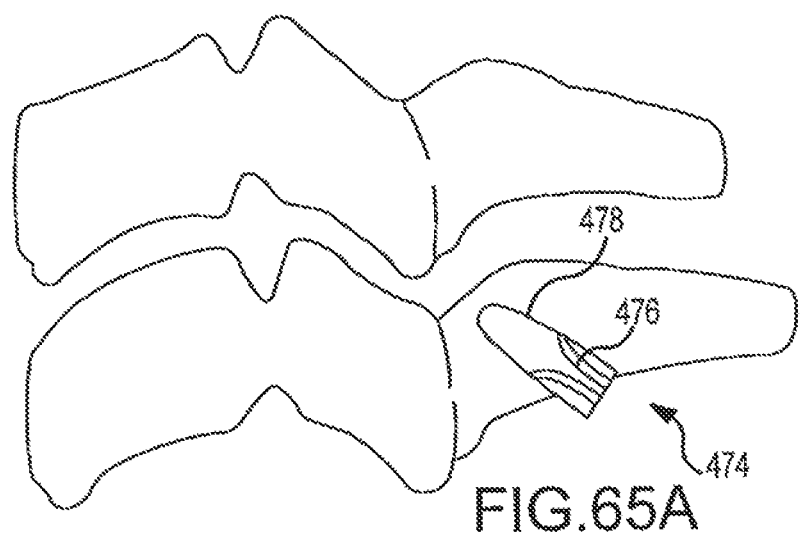
FIGS. 65A-C include side and perspective views of an implant, according to certain embodiments.
Figure 65B:
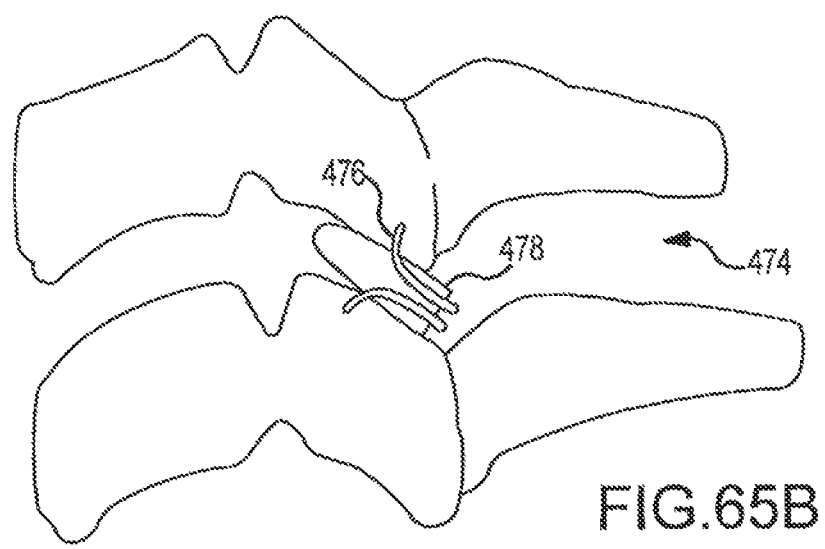
Figure 65C:
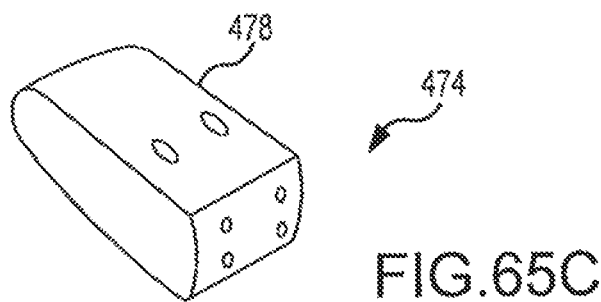

FIGS. 65A-C show yet another embodiment of an implant 474. In this embodiment, nitinol hooks 476 may be configured to have a memory. The hooks 476 may be flattened and inserted through a delivery system 478. The delivery system 478 may be placed in a facet joint. Once inserted within the facet, the nitinol hooks 476 may be activated via temperature, force, or other activation means causing them to assume their original (pre-flattened) shape and hook into the opposing facet surfaces. As the hooks 476 engage the cortical bone of the facet surfaces, they distract the joint. This separation results in increased foraminal area and reduced nerve root compression.

Figure 66A:
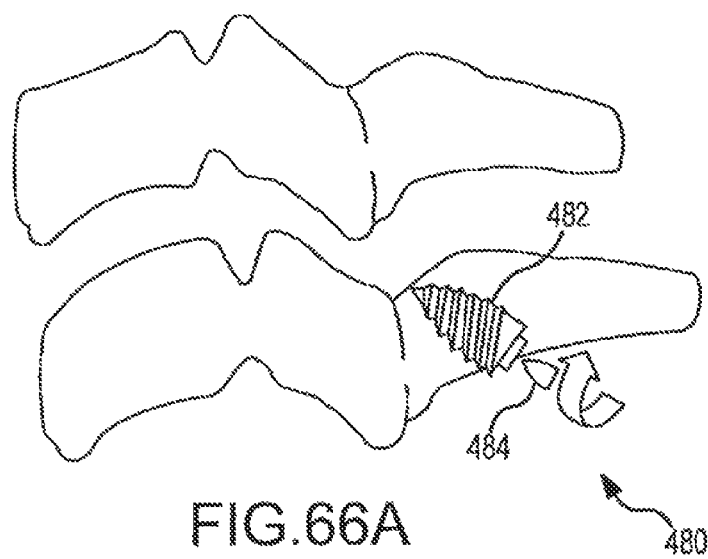
FIGS. 66A-C include side views of an implant, according to certain embodiments.
Figure 66B:
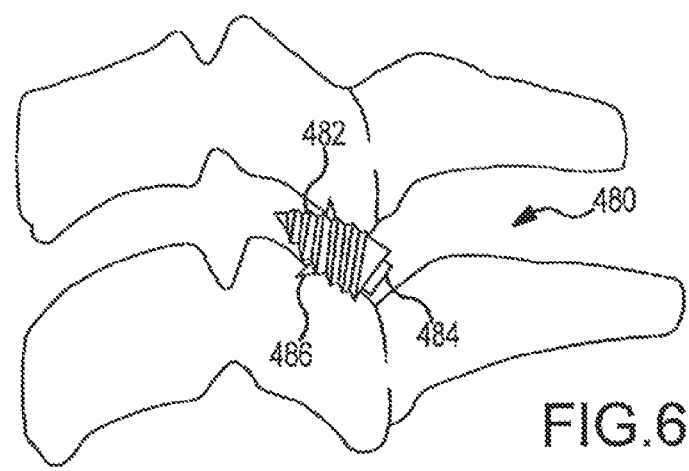
Figure 66C:
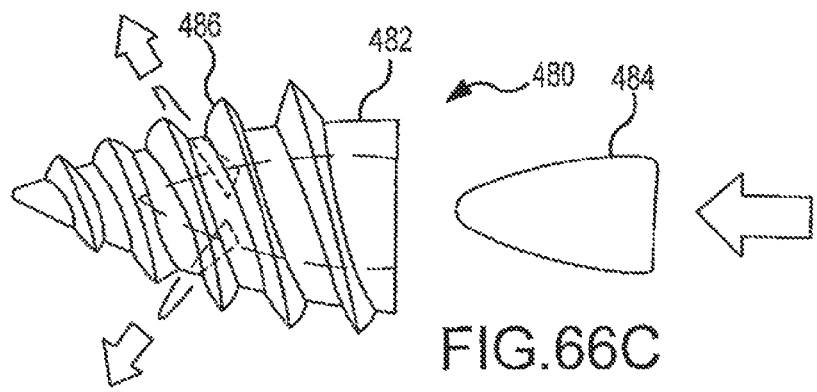

FIGS. 66A-C show yet another embodiment of an implant 480. In this embodiment, a hollow screw sleeve 482 may be placed within the facet joint. A wedge 484 may then be placed within the hollow screw sleeve 482 causing it to expand and distract the joint. Additionally, the screw sleeve 482 may include sharp barbs 486 having a refracted position and a ejected position. As the wedge 484 is inserted, the wedge 484 displaces the sharp barbs 486 causing them to be ejected through the screw sleeve 482 and engage the facet surfaces. These barbs 486 may provide acute fixation of the implant 480 to the joint and prevent migration of the implant 480. The distraction and separation of the joint result in increased foraminal area and reduced nerve root compression.

Figure 67A:
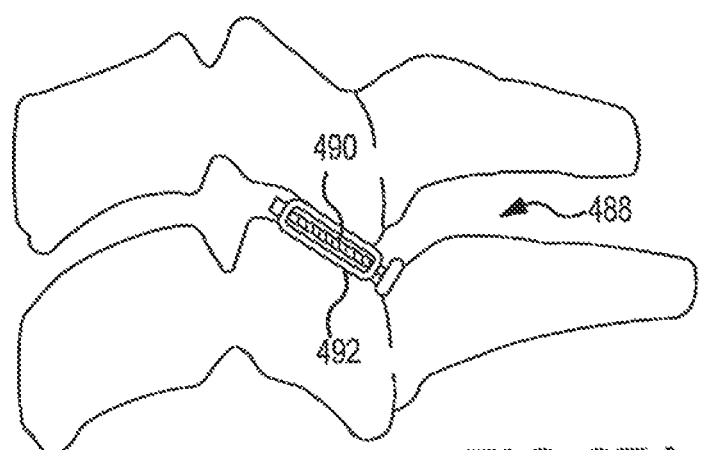
FIGS. 67A-C include side and perspective views of an implant, according to certain embodiments.
Figure 67B:
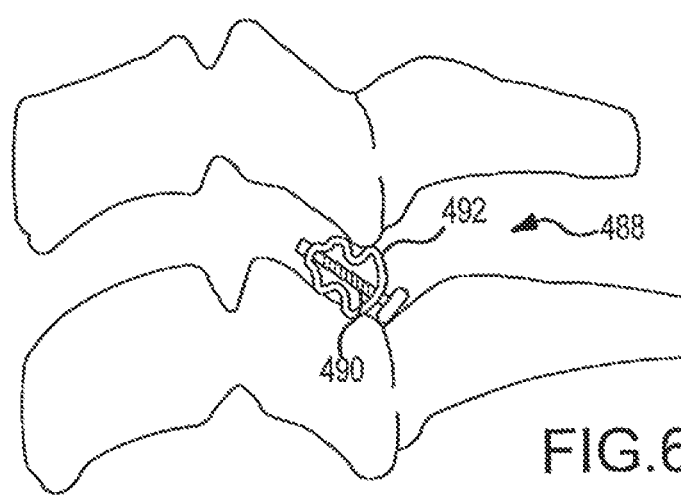
Figure 67C:
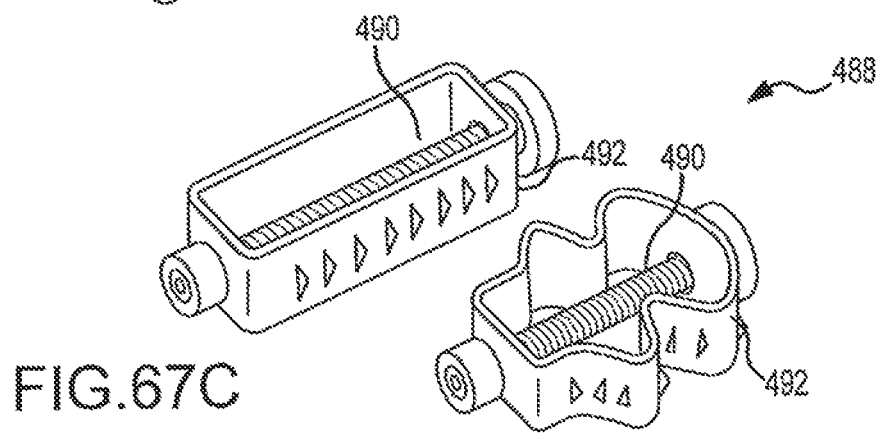

FIGS. 67A-C show yet another embodiment of an implant 488. In this embodiment, a panel anchor implant 488 may be placed within the facet joint. The implant 488 may include a bolt 490 and collapsible nut 492 that is rotationally free from the bolt 490 near the head of the bolt 490 and threadably engaged with the bolt 490 near the end opposite the head. As such, when the bolt 490 is advanced, the distal end of the nut 492 is squeezed toward the proximal end of the nut 492 and the nut 492 may collapse with an accordion effect. As shown, the compression of the nut 492 results in a taller structure that applies a distraction force to the opposing facet surfaces. This distraction leads to increased foraminal area and reduced nerve root compression.

Figure 68A:
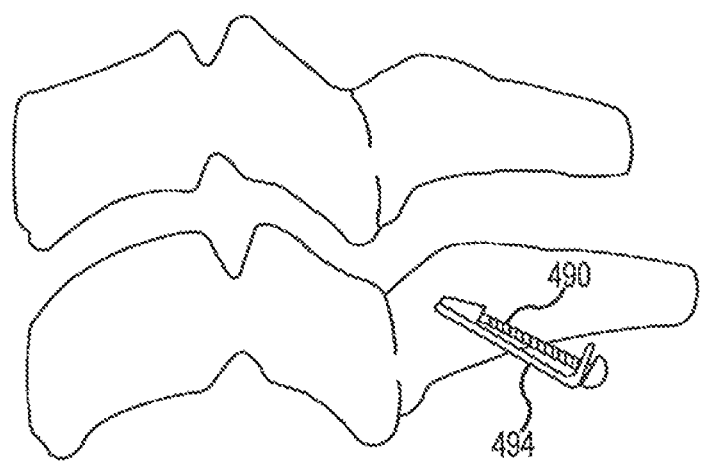
FIGS. 68A-C include side and perspective views of an implant, according to certain embodiments.
Figure 68B:
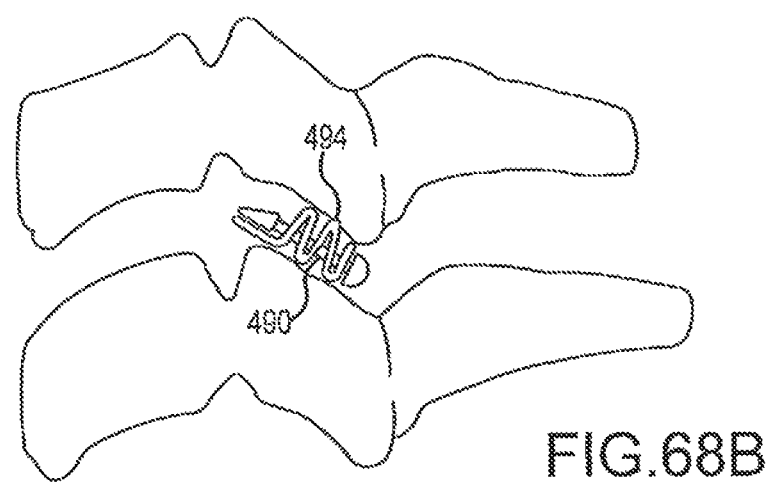
Figure 68C:
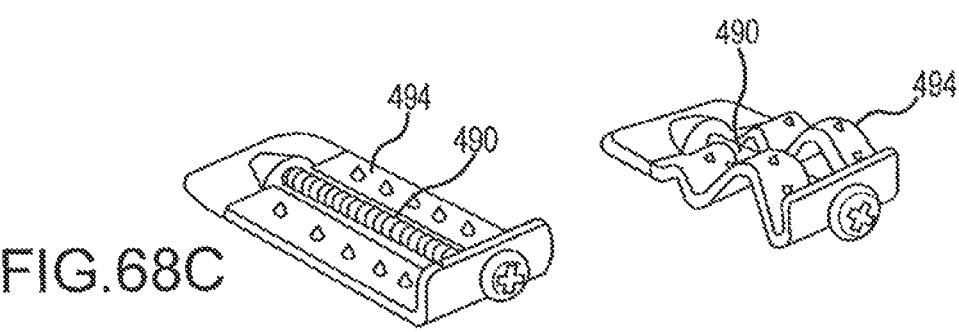

In similar fashion, the embodiment shown in FIGS. 68A-C may collapse causing distraction of the joint. In lieu of the nut 492 shown in FIGS. 67A-C, this embodiment, shows a flat plate 494 that collapses into an accordion shape.

Figure 69A:
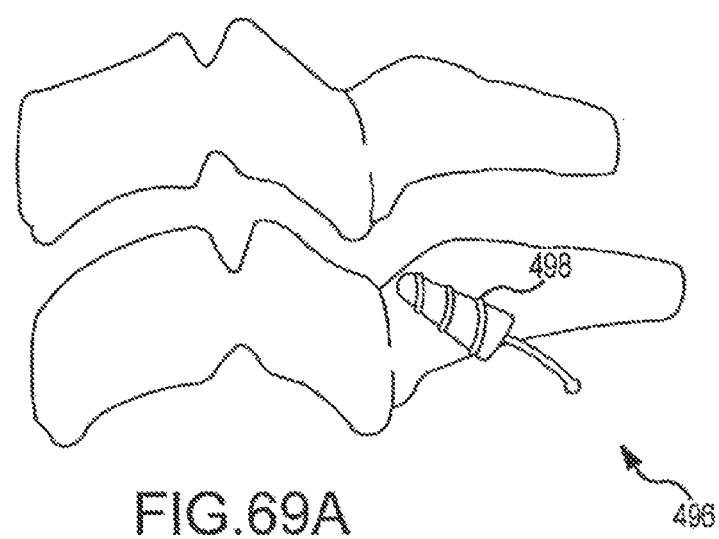
FIGS. 69A-C include side and perspective views of an implant, according to certain embodiments.
Figure 69B:
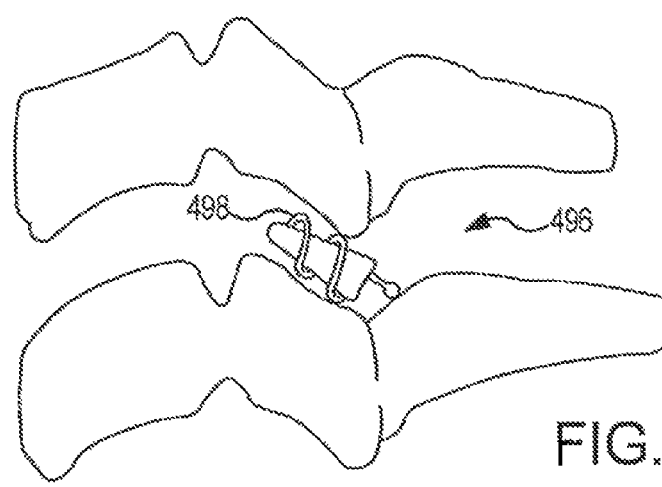
Figure 69C:
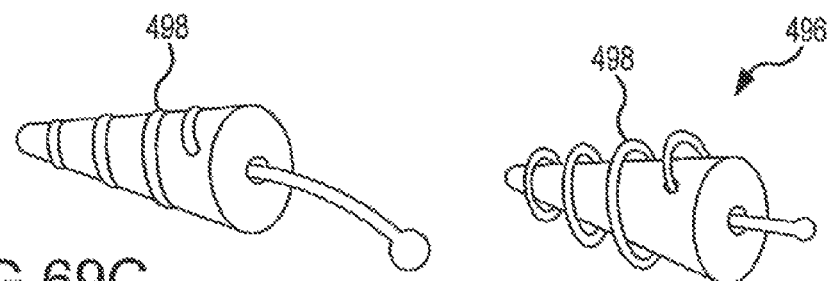

FIGS. 69A-C show yet another embodiment of an implant 496. In this embodiment, an implant 496 is placed within the facet joint. The implant could have a number of shapes and sizes but, in this embodiment, has a tension wire 498 that surrounds the implant 496 and is pulled taught during implantation. Once the implant 496 is properly positioned, the wire's tension is released. The release of this tension causes the wire 498 to return to a preset expanded shape and height that causes the implant 496 to expand. The expansion of the implant 496 as the wire returns to its preset, and larger profile, shape causes separation of the facet joint. This distraction results in increased foraminal area and reduced nerve root compression.

Figure 70A:
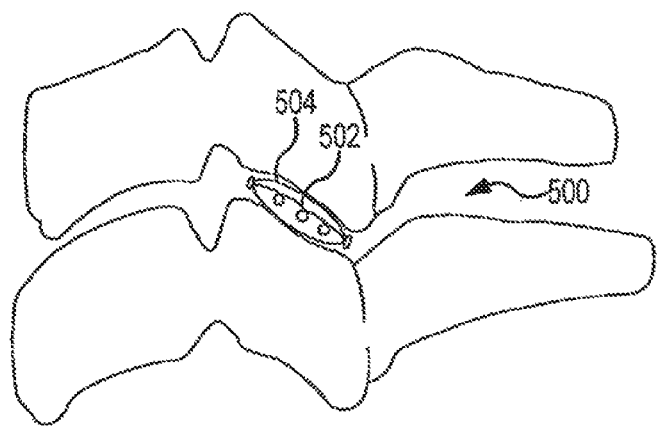
FIGS. 70A-C include side views of an implant, according to certain embodiments.
Figure 70B:
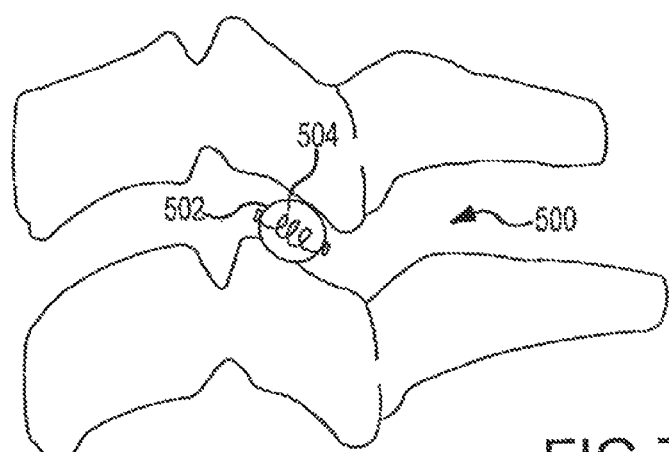
Figure 70C:
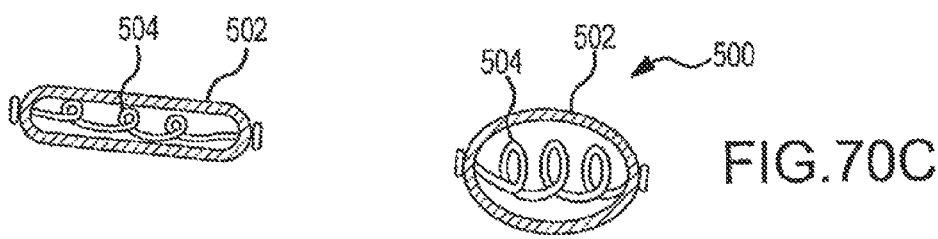

Similarly, as shown in FIGS. 70A-C, an implant 500 with an outer housing 502 and an internal spring 504 may be positioned in the facet joint with the wire spring 504 in a tensioned or elongated position. Once properly positioned, the tension on the spring 504 may be released thus collapsing the spring 504 and expanding the associated housing 502 of the implant 500.

Figure 71A:
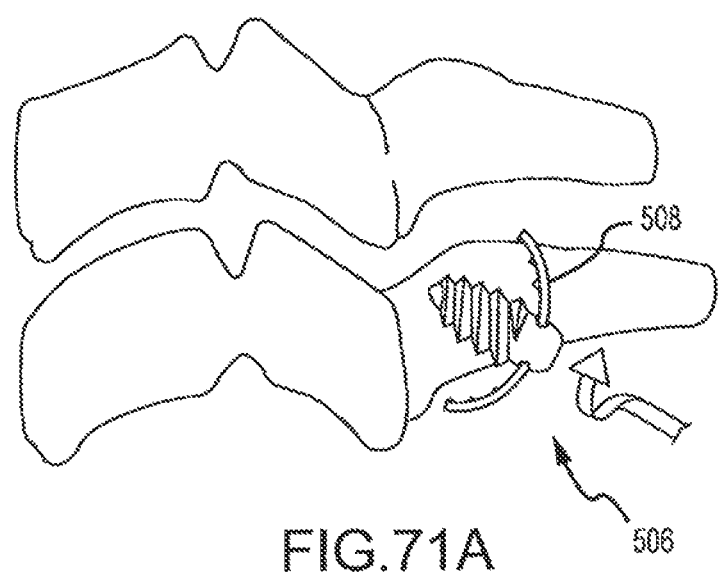
FIGS. 71A-C include side and perspective views of an implant, according to certain embodiments.
Figure 71B:
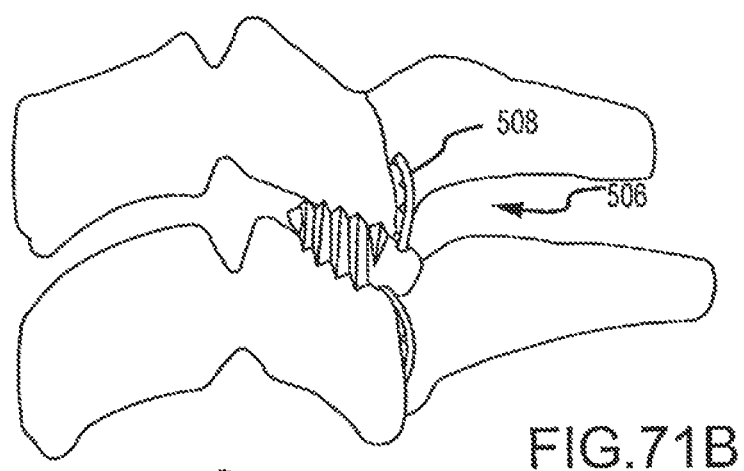
Figure 71C:
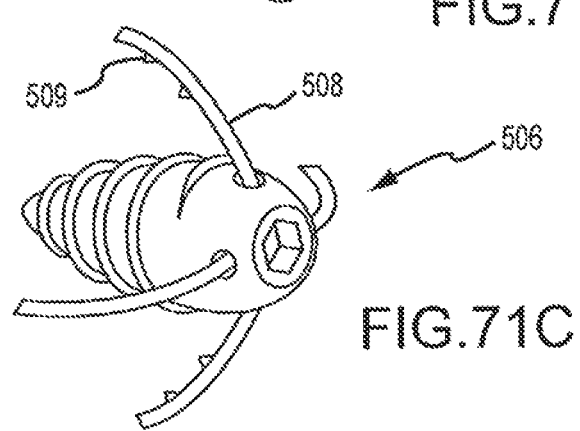

FIGS. 71A-C show yet another embodiment of an implant 506. In this embodiment screw type implant 506 may be provided and may also include an arm type locking mechanism 508. The locking mechanism 508 may extend from all sides of the head of the screw as shown and may be biased in a distal direction. As the screw advances, the locking mechanism 508 may anchor in the lateral mass of a vertebra. The biased position of the arm 508 pressing against the lateral mass may provide a force biasing the implant 506 against the advancing direction. However, this may cause constant friction between any newly cut threads in the surfaces of the facet joint thereby preventing unscrewing or back out of the implant. In addition, teeth 509 may be included on the arms 508 and may bite into the lateral mass further preventing backing out of the implant.

Figure 72A:
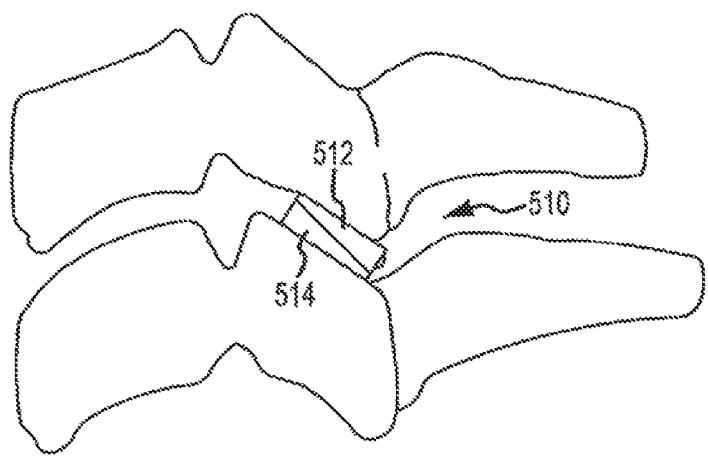
FIGS. 72A-C include side and perspective views of an implant, according to certain embodiments.
Figure 72B:
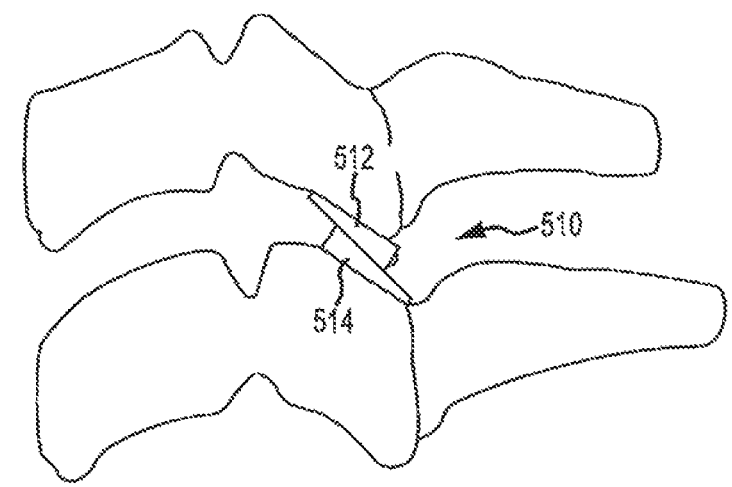
Figure 72C:
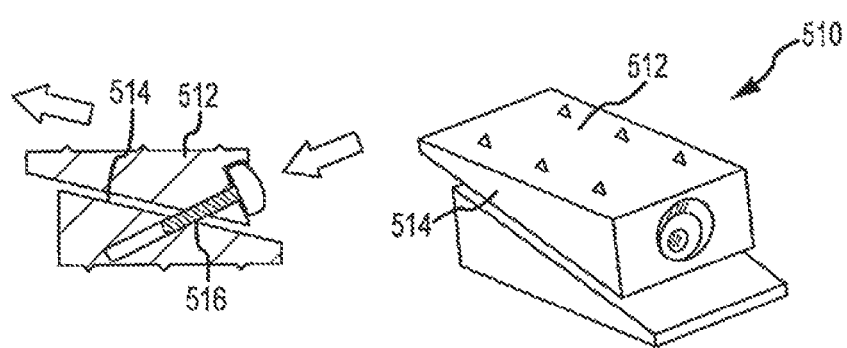

FIGS. 72A-C show yet another embodiment of an implant 510. In this embodiment, two wedge shape opposing structures 512 are shown separated by a sloping plane 514. The structures 512 may have a predetermined relative position, or a series of predetermined relative positions, where a bolt or screw 516 may be advanced at an angle as shown through one of the structures 512 and into a predrilled hole of the other 512 to maintain their relative position. Alternatively, the relative positions may not predetermined and a self-drilling screw 516 may be used. In either case, the implant 510 may be positioned in the facet joint in minimal profile position and then the two structures 512 may be slid relative to each other along the sloping plane 514 to expand the implant 510 and thus the facet joint. Once the desired position is achieved, the bolt, pin, screw, or other fastener 516 may be inserted to maintain the relative position of the structures 512.

Figure 73A:
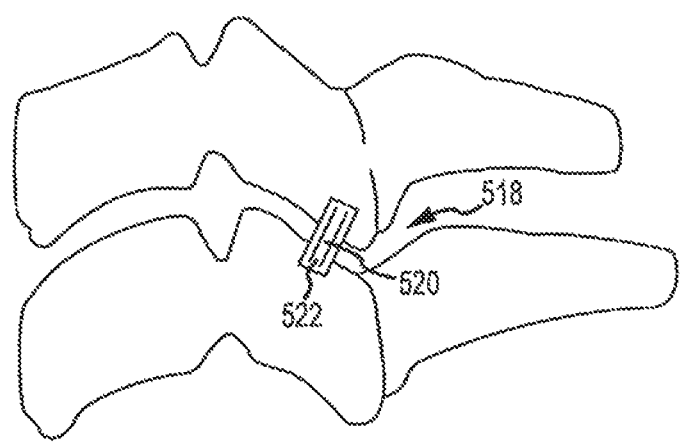
FIGS. 73A-C include side and perspective views of an implant, according to certain embodiments.
Figure 73B:
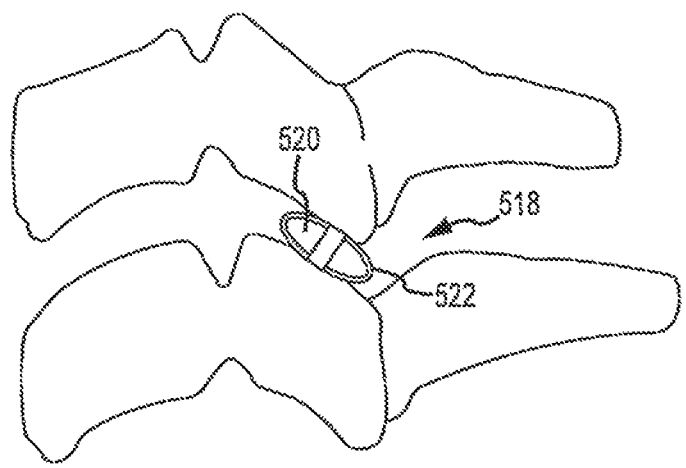
Figure 73C:
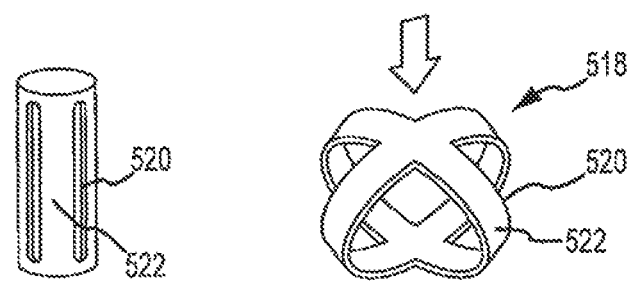

FIGS. 73A-C show yet another embodiment of an implant 518. In this embodiment, an implant 518 is configured to be inserted in a collapsed state. In its non collapsed state, it has a vertical cylindrical profile with side cutouts 520. When the implant is compressed, the side cutouts 520 allow the wall panels 522 to bend out as the height of the cylindrical implant 518 is reduced. These wall panels 522 create an anchor shape that can engage bone structures. This implant 518 may be placed within the facet join in its flattened, compressed profile. Once it is positioned correctly, a distraction energy may be applied to the implant 518 to cause it to expand or decompress. This decompression causes the implant 518 to attempt to return to its vertical cylindrical shape. The implant 518 may be made from a resilient elastic material such as nitinol, stainless steel, or other known materials. As the implant 518 becomes more cylindrical, it pushes against the opposing facet surfaces. This force causes distraction of the facet joint and results in increase foraminal area and reduced nerve root compression.

Figure 74A:
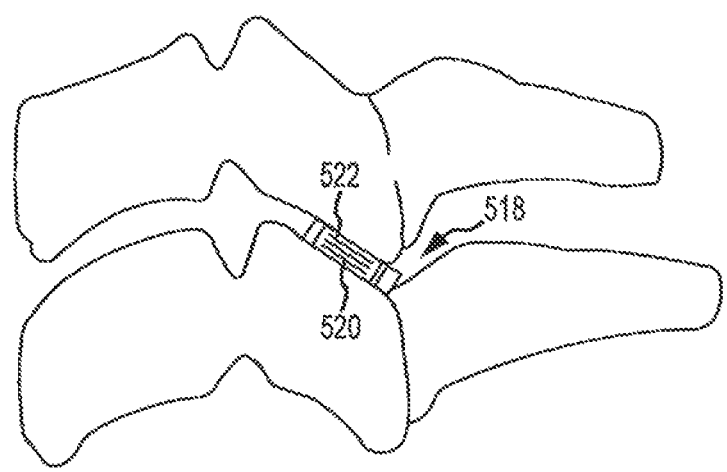
FIGS. 74A-C include side and perspective views of an implant, according to certain embodiments.
Figure 74B:
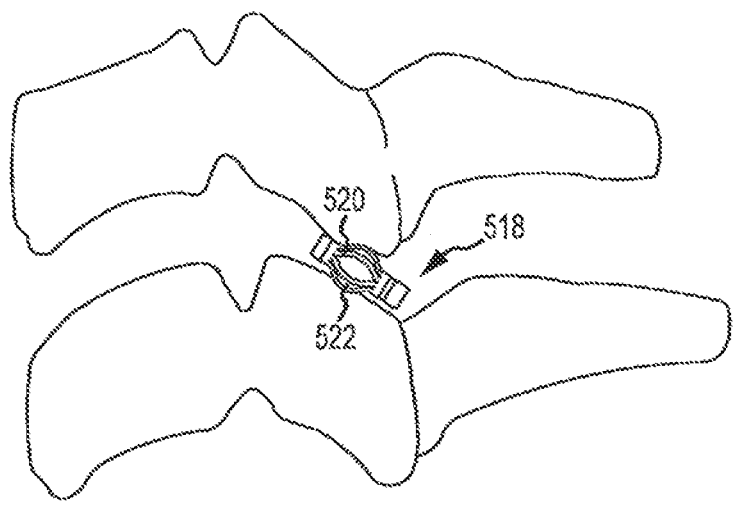
Figure 74C:
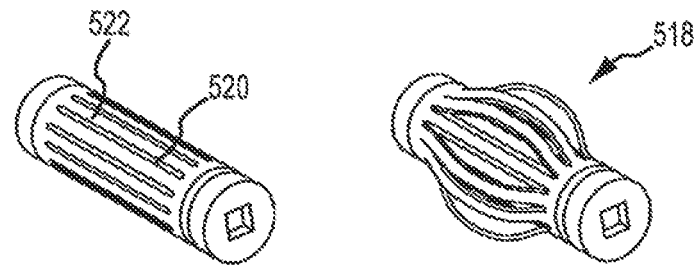

Similarly, as shown in FIGS. 74A-C, the implant 518 may be positioned on its side and the distraction energy may cause the implant 518 to collapse from its cylindrical shape and expand laterally to distract the facet joint.

Figure 75A:
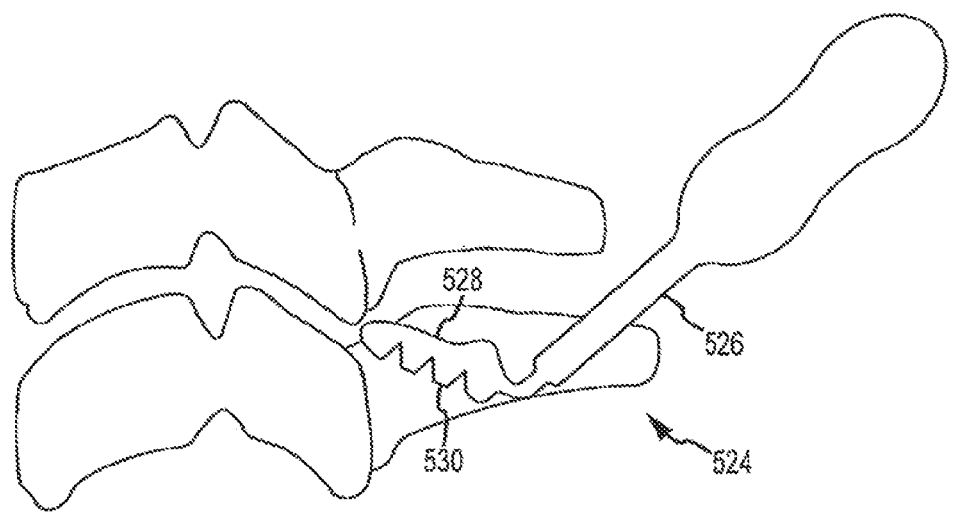
FIGS. 75A-B include side views of an implant, according to certain embodiments.
Figure 75B:
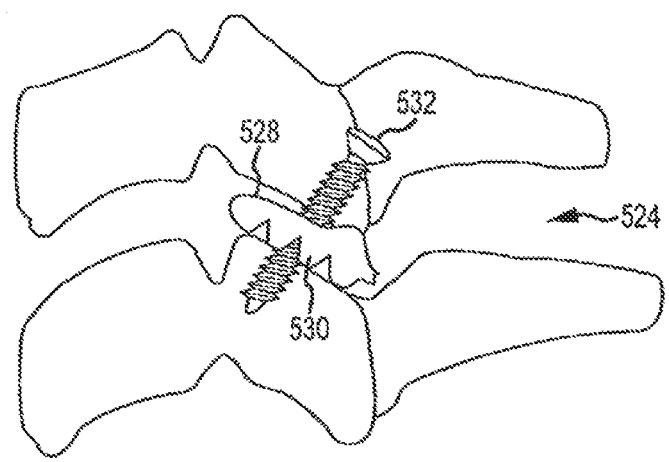

FIGS. 75A-B show yet another embodiment of an implant 524. In this embodiment, a delivery tool 526 is inserted within the facet joint. The distal tip 528 of the delivery tool 526 is shaped to distract the joint. Once the tool 526 is inserted into the facet joint and the desired amount of distraction is achieved, the distal tip 528 (part that is in the facet joint) may be detached from the delivery tool 526. In one configuration of this embodiment, the detachable tip 528 would have teeth, cleats, spikes, or keels 530 to prevent it from migrating within the joint once it is detached. In another configuration of this embodiment, the implant 524 may be anchored in the facet joint by inserting a screw 532 through the superior facet, the implant, and the inferior facet. In both configurations, the detachable tip 526 (implant) may provide permanent distraction of the joint resulting in increased foraminal area and reduced nerve root compression.

Figure 76A:
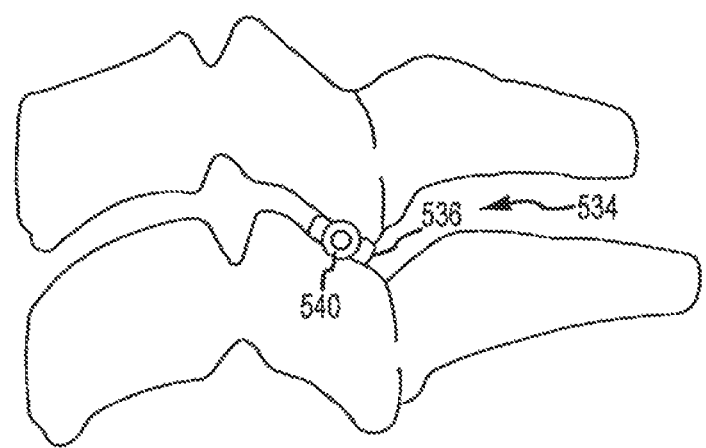
FIGS. 76A-C include side and perspective views of an implant, according to certain embodiments.
Figure 76B:
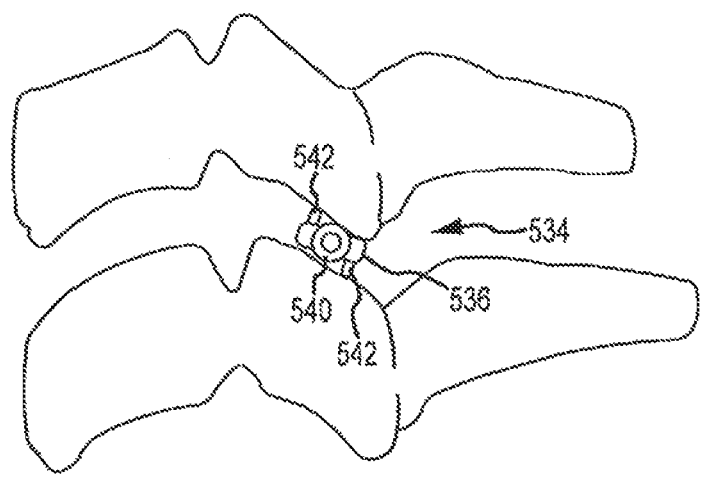
Figure 76C:
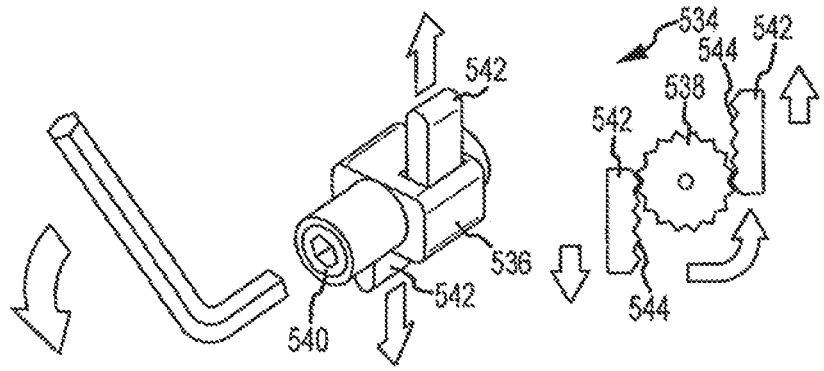

FIGS. 76A-C show yet another embodiment of an implant 534. In this embodiment, the implant 534 may include a housing 536 with a central gear 538 turnable by an Allen type head 540 or other known attachment for turning, such as any known screwdriver heads. Adjacent the central gear 538 on each side, the implant 534 may include two plates 542 slidable in the housing 536 in a direction tangential to the gear surface. The plates 542 may include teeth 544 engaging the central gear 538 such that when the gear 538 turns, the plates 542 slide tangentially to the gear 538 and extend beyond an outer surface of the housing 536. As such, the implant 534 may be positioned in a facet joint as shown in FIG. 76A. Once positioned, the gear 538 may be turned thus extending the plates 542 in opposite directions and distracting the facet joint.

Figure 77A:
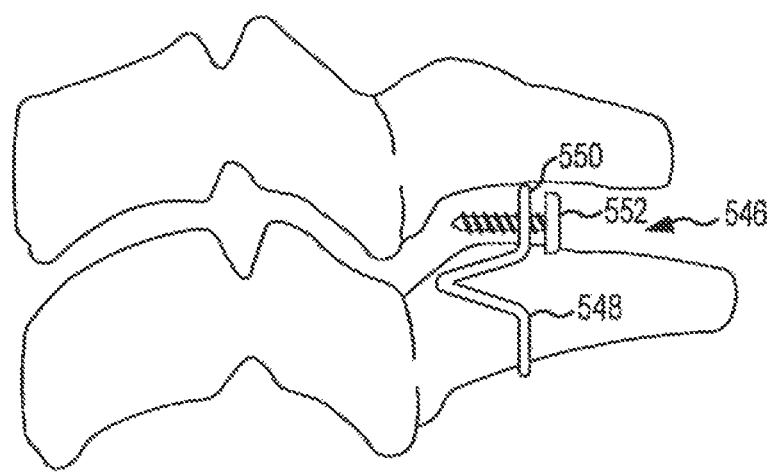
FIGS. 77A-C include side and perspective views of an implant, according to certain embodiments.
Figure 77B:
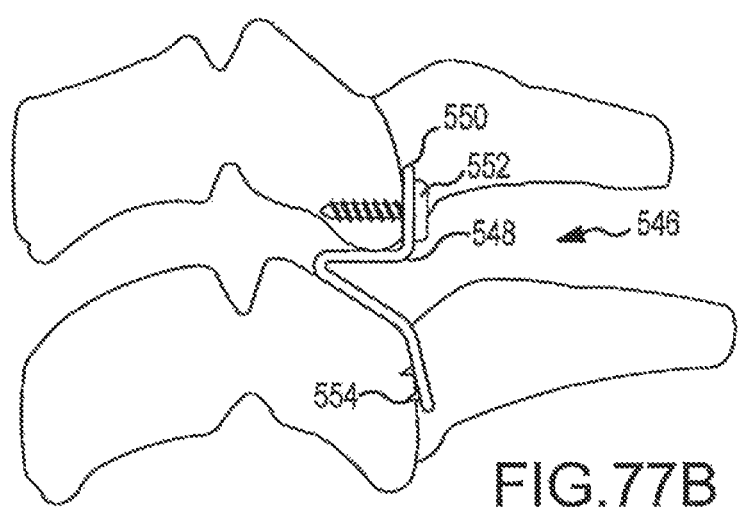
Figure 77C:
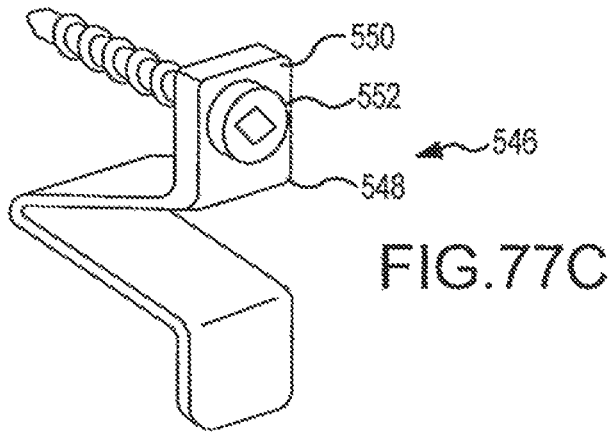

FIGS. 77A-C show another embodiment of an implant 546. In this embodiment a triangular shaped implant 546 in the form of a bent plate 548 may be wedged into the facet causing distraction and separation of the joint. On one side of the triangular distraction structure 548 is a bracket 550 with a screw 552. The screw 552 may be inserted into the lateral mass to provide anchoring of the facet distraction implant 546. The other side of the triangular distraction structure 548 may include teeth or other features 554 for biting into the associated lateral mass. The implant 546 would provide permanent distraction of the joint resulting in increase foraminal area and reduced nerve root compression.

Figure 78A:
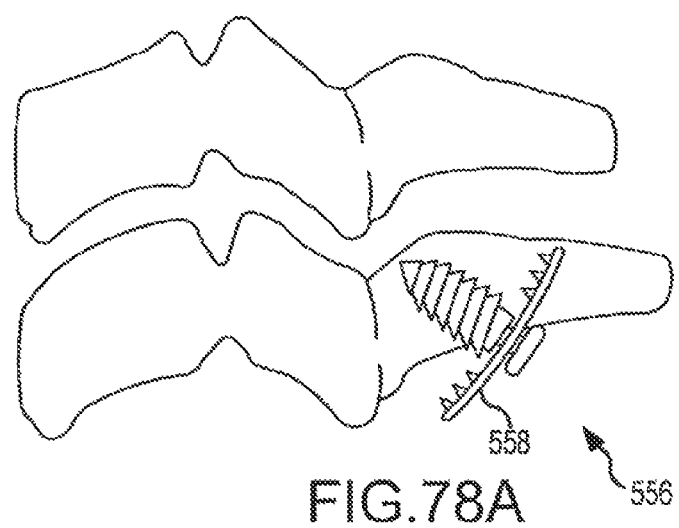
FIGS. 78A-C include side and perspective views of an implant, according to certain embodiments.
Figure 78B:
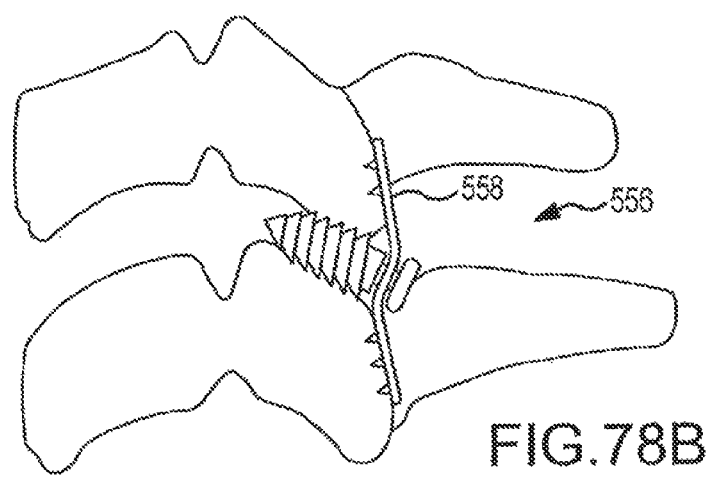
Figure 78C:
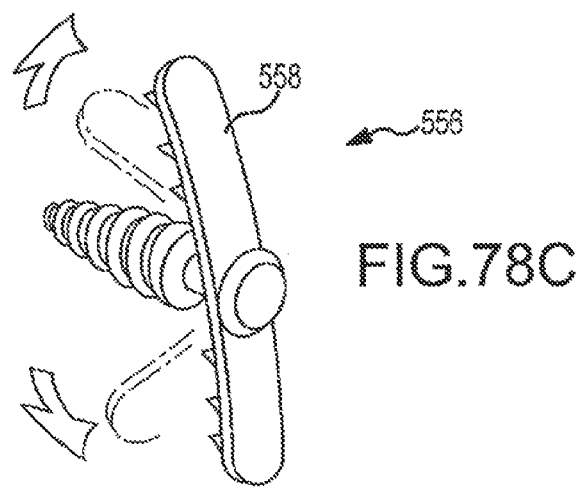

FIGS. 78A-C show another embodiment of an implant 556. In this embodiment, the implant 556 may have a tapered shape that is taller at the posterior aspect relative to the anterior aspect. The implant could be tapped in, malleted in, screwed in with threads, or pushed in with hand pressure. Once the implant 556 is positioned correctly, the head 558 of the implant 556 (posterior aspect) may be configured to have sharp teeth, spikes, or cleats that can be pushed into the cortical bone of the superior and inferior lateral masses of a motion segment. These flaps 558 could be hinged on the posterior aspect of the implant 556 to allow the flaps 558 to be pushed anterior enough to match the irregular contours of the lateral mass. The implant 556 would provide permanent distraction of the joint resulting in increase foraminal area and reduced nerve root compression.

Figure 79A:
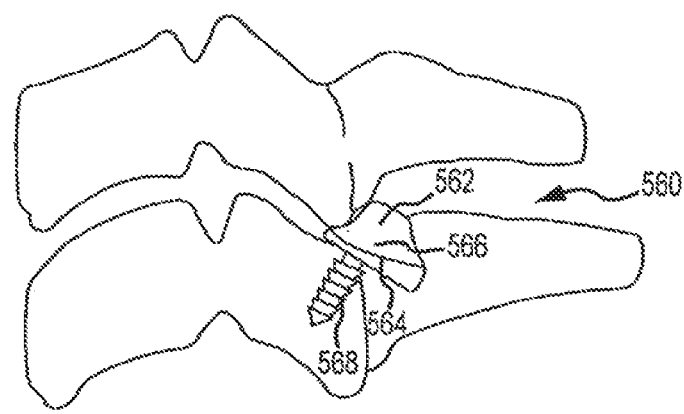
FIGS. 79A-C include side and perspective views of an implant, according to certain embodiments.
Figure 79B:
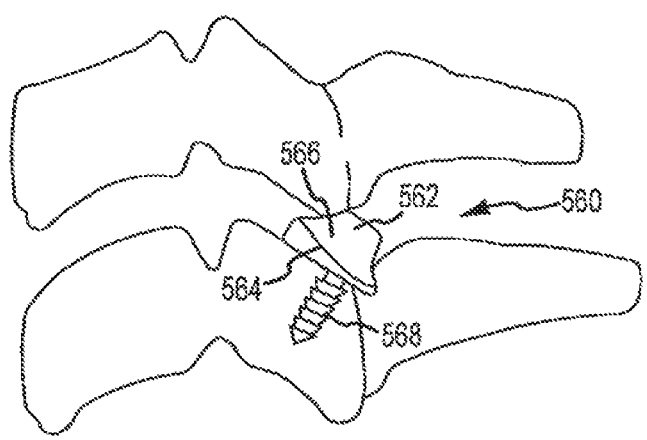
Figure 79C:
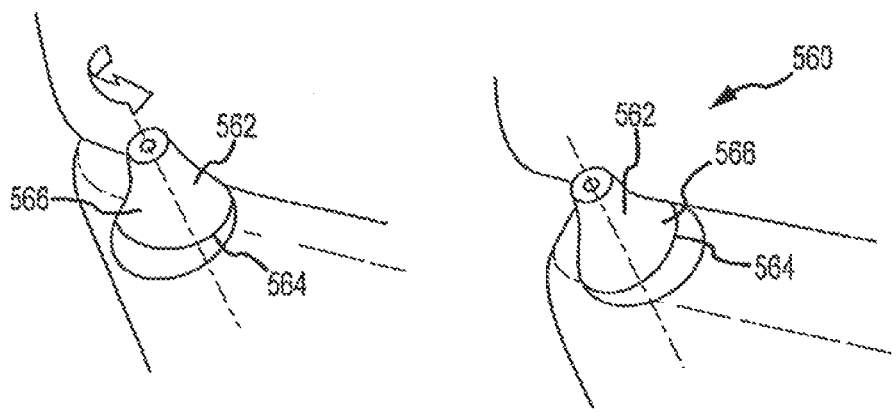

FIGS. 79A-C show another embodiment of an implant 560. In this embodiment, the implant 560 includes a single rotatable cone 562 with a shoulder shaped ledge 564 defining a cam surface 566, the distance between the ledge and the bottom of the implant defining a shoulder height. The shoulder height may vary gradually from low to high and back to low along the circumferential perimeter of the cone 562. In use, the implant 560 may be initially positioned such that the shoulder portion with the low ledge height enters the facet joint. Once in position, the implant 560 may be rotated to cause the higher ledge height to enter the joint thereby distracting the posterior portion of the joint by causing the superior articular face to ride upward along the cam surface 566. The implant 560 may then be secured with a screw 568 extending along the longitudinal axis of the implant.

FIGS. 80A-D show yet another embodiment of an implant 570. In this embodiment, an implant 570 may include a housing 572 with penetrations 574 adapted for ejection of retracted spikes 576. Within the housing 572, a wire 578 may be routed between the spikes 576 as shown in FIG. 80D. The implant 570 may be inserted into the facet joint while the wire 578 is relaxed and the spikes 576 are contained within the folds/curves in the collapsed wire 578. Once the implant 570 is positioned correctly, the wire 578 may be pulled taught causing the spikes 576 to displace outwardly, extending out of the housing 572 and engaging the opposing facet surfaces with a force. This force may create distraction and separation of the joint, while the pointed tips of the spikes 576 would penetrate the surface of the facet joint and provide acute fixation preventing migration of the implant 570. The implant 570 would provide permanent distraction of the joint resulting in increase foraminal area and reduced nerve root compression.

Figure 81A:
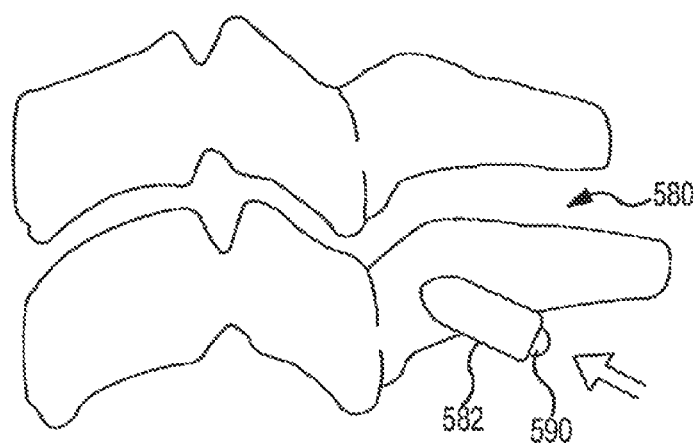
FIGS. 81A-C include side views of an implant, according to certain embodiments.
Figure 81B:
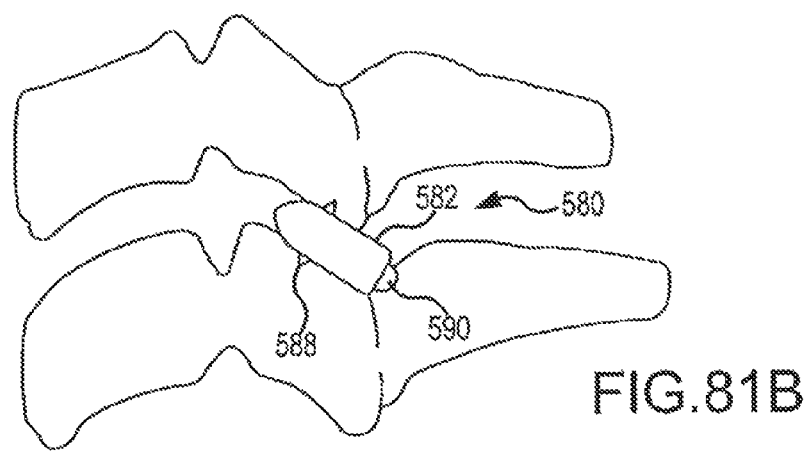
Figure 81C:
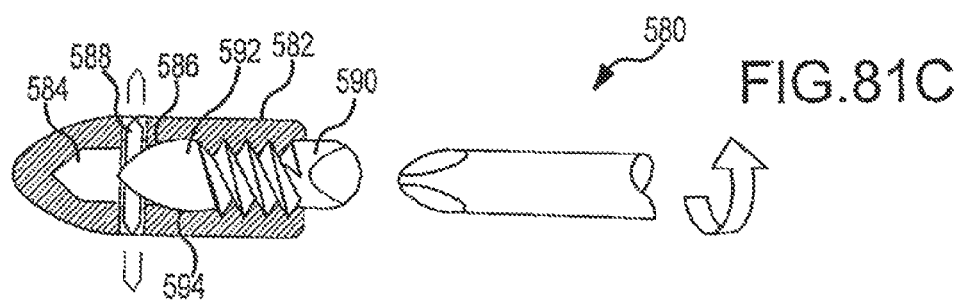

FIGS. 81A-C show yet another embodiment of an implant 580. In this embodiment, an implant 580 may include a housing 582 with a cavity 584 and penetrations 586 on lateral surfaces extending from the cavity 584 through the wall of the housing 582, the penetrations 586 adapted for ejection of retracted spikes 588. Within the housing 582, a threaded piston 590 may be positioned at a distal end and may be adapted for displacement through the cavity 584 in the proximal direction. The piston 590 may have a torpedo shaped distal end 592 and may engage the a beveled inner surface 594 of the retracted spikes 588. The implant 580 may be positioned within a facet joint and when properly positioned, the piston 590 may be advanced via a turning tool, the torpedo shaped distal end 592 of the piston 590 thus engaging the beveled end 594 of the spikes 588 and advancing them laterally relative to the implant 580 out of the housing 582 with a force and into the face of the facets. This force may create distraction and separation of the joint, while the pointed tips of the spikes 588 would penetrate the surface of the facet joint and provide acute fixation preventing migration of the implant 580.

Figure 82A:
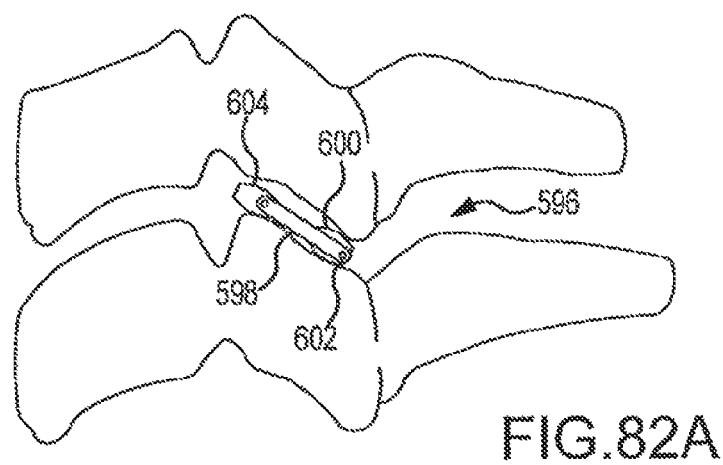
Figure 82B:
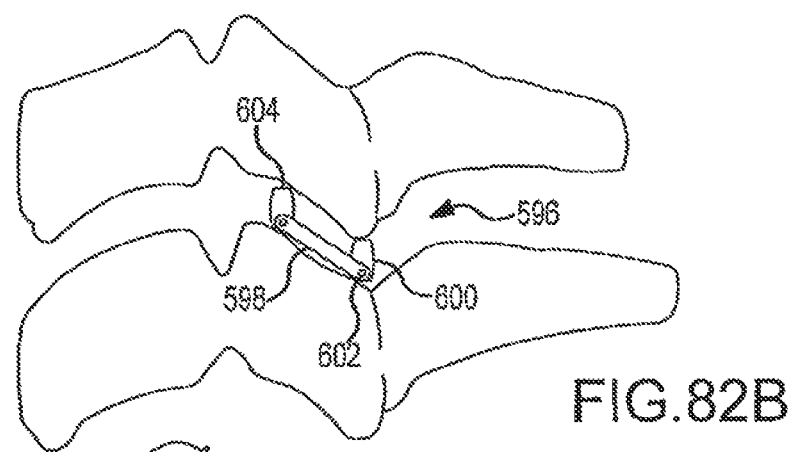
Figure 82C:
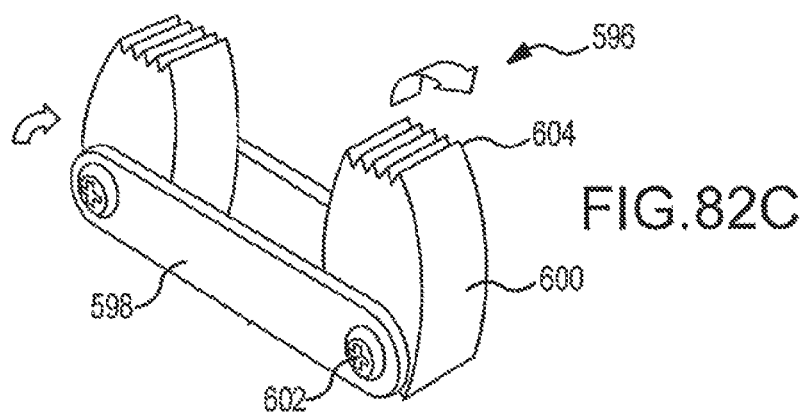

FIGS. 82A-F show yet another embodiment of an implant 596. In this embodiment, the implant 596 may include two parallel equal length side bars 598 with pivoting struts 600 positioned on a pin 602 between the bars 598 at each end. The pivoting struts 600 may include textured surfaces 604 on each end and the struts 600 may be pinned to the side bars 598 through one end. As shown in FIG. 82F, the struts 600 may have length so as to allow them to be pivoted to lie parallel to one another in the plane of the side bars 598. In this position, the implant 596 may be positioned in the facet joint as shown in FIG. 82A or anterior to the facet joint as shown in FIG. 82D. Once properly positioned, the struts 600 of the implant 596 may be rotated so as to be approximately perpendicular to parallel side bars 598 thus separating an inferior vertebra from a inferior vertebra. It is noted that the generally stout shape of the struts 600 with relatively broad textured ends 604 may facilitate stability preventing the implant 596 from racking back to the parallel condition.

Figure 83A:
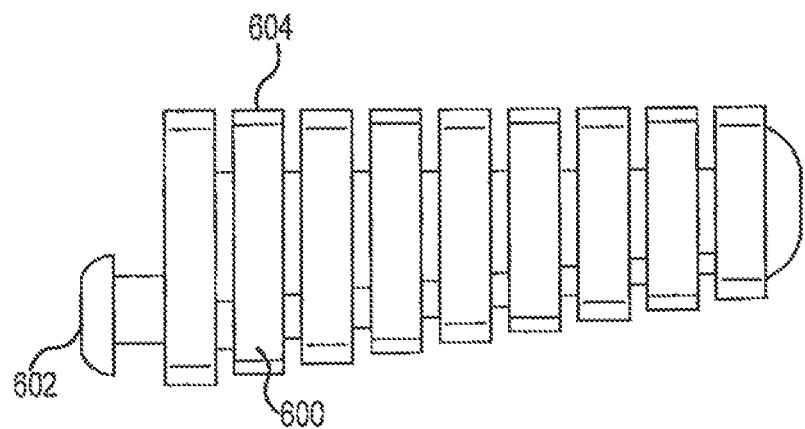
FIGS. 83A-B include side and perspective views of an implant, according to certain embodiments.
Figure 83B:
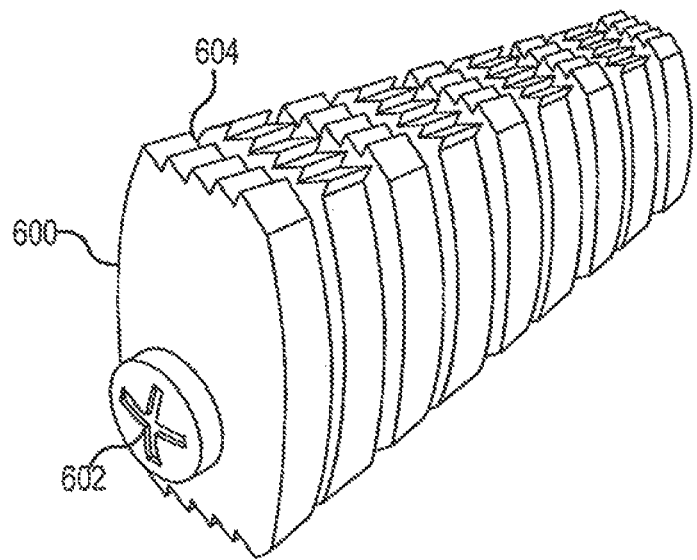

Another variation of this embodiment is shown in FIGS. 83A-B, where a series of varying height struts 600 are positioned along a shaft. The entire implant may be placed within a facet joint on its side and then a single ninety degree turn may position the implant and distract the joint.

Figure 84A:
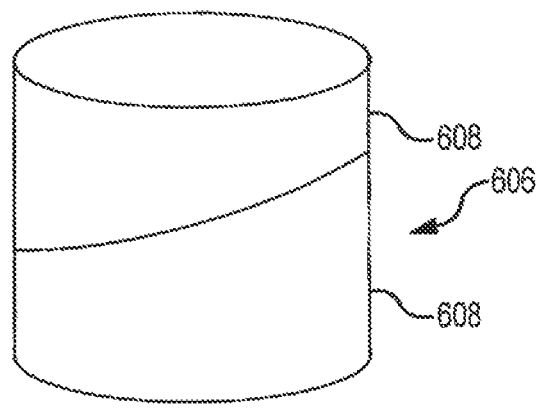
FIGS. 84A-B include perspective views of an implant, according to certain embodiments.
Figure 84B:
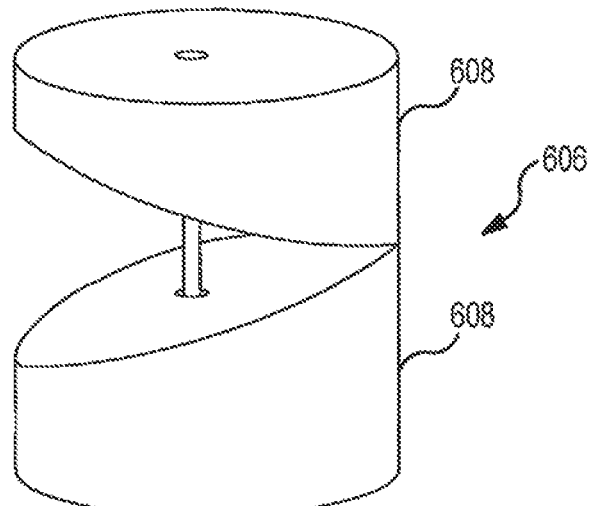

FIGS. 84A-B show yet another embodiment of an implant 606. In this embodiment, two rotatable cams 608 may be positioned in a facet joint. It is noted that the cams may have a relatively low profile and the proportions in the FIGS. may be exaggerated for purposes of showing the concept. Once placed in the joint, a distraction/rotation energy may be applied to the cams causing them to rotate open to reveal two circular halves of the cam implant. As one half of the implant rotates superiorly, it may push the superior vertebra upward creating an increase in foraminal area and nerve root decompression.

Figure 85:
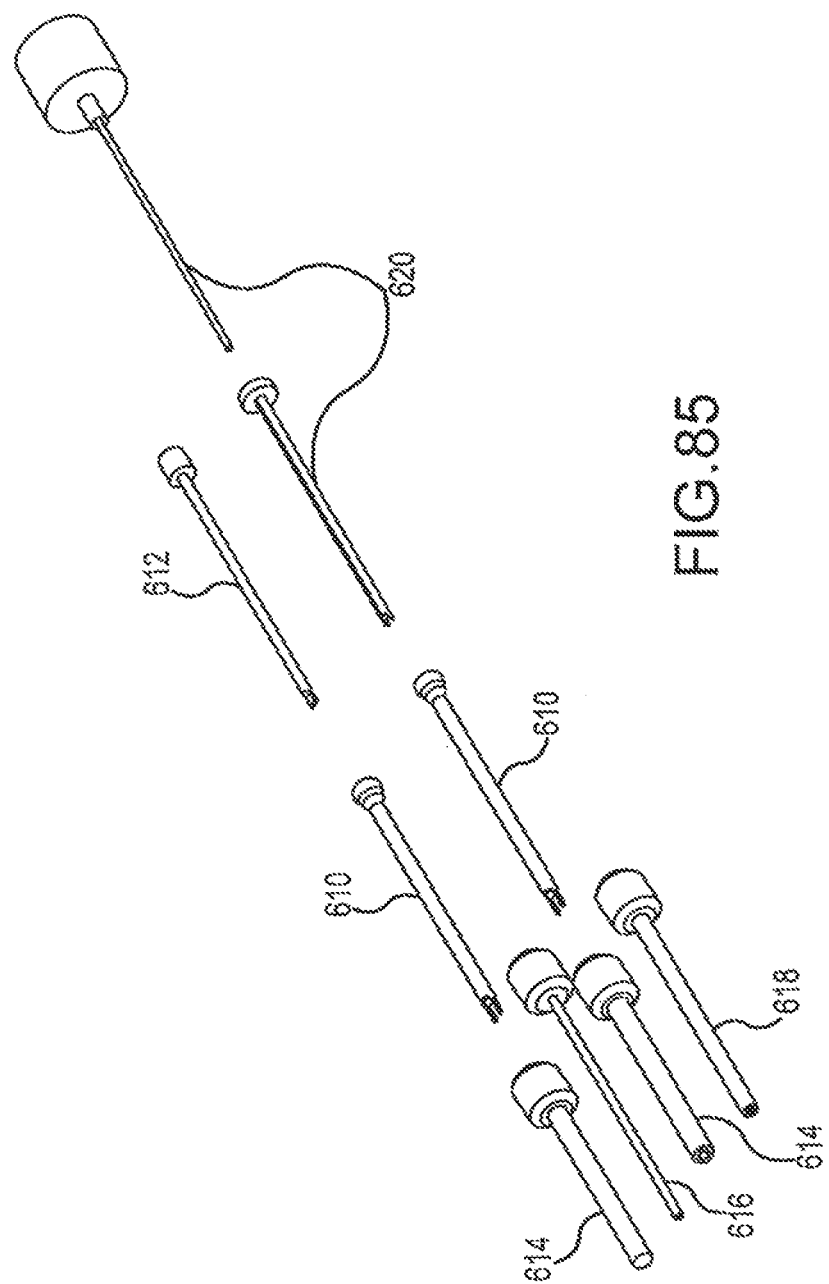
FIG. 85 is an exploded perspective view of a kit, according to certain embodiments.
Figure 91:
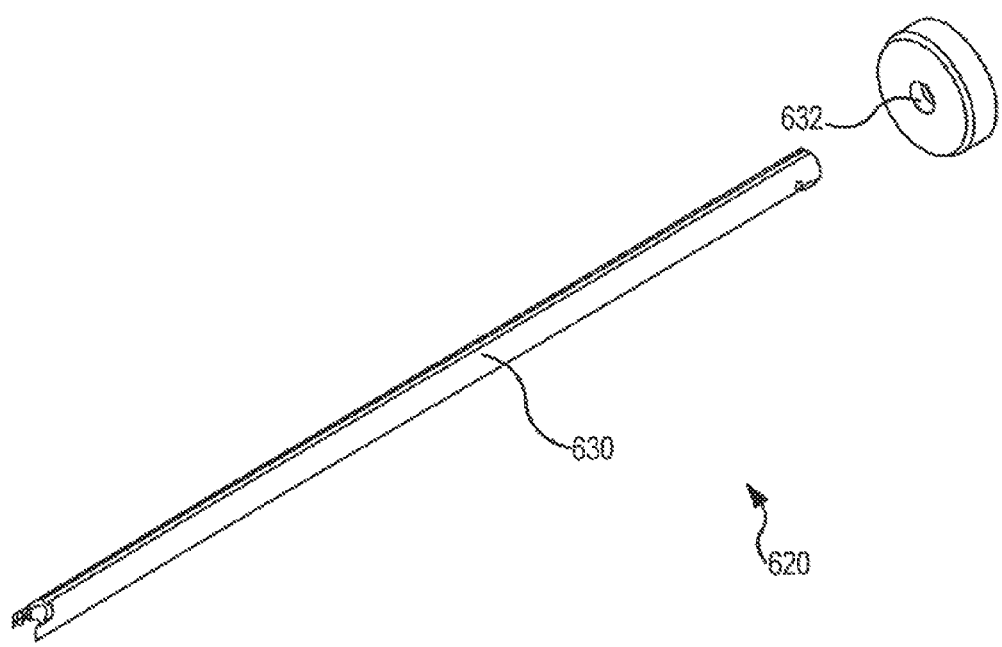
FIG. 91 is a perspective view of part of a driver assembly portion of the kit shown in FIGS. 85 and 86.

In another embodiment, a kit is provided. As shown in FIGS. 85 and 86, the kit may include a delivery device 610, a chisel 612, several internal and external decorticators 614, 616, 618, and a driver assembly 620. As shown in FIGS. 87 and 88, the chisel head 622 and shaft 624 may be provided in two pieces that may be combined with a press fit. As shown in FIG. 89, the delivery device 610 may be provided in two pieces combinable with a press fit, the first piece being a tubular shaft and fork piece 626 and the second piece being a receiving assembly piece 628. As show in FIGS. 90-93, the driver assembly 620 may be provided in several pieces including the internal actuator and the implant shaft/arms/handle portion. FIG. 90 shows the shaft/arms/handle portion comprising two pieces, the first piece being a shaft with arms 630 and the second piece being the handle 632. FIGS. 91 and 92 show the internal actuator including a tip 634, a shaft portion 636, an adapter 638, a pin 640, and a distractor knob 642. In addition to the elements shown, one or several implants may be provided as well as an injector as previously described. Several traditional instruments for use in accessing the surgical site and closing the surgical site may also be provided.

Those of skill in the art will understand and appreciate that the implant embodiments depicted herein may be made of several types of biocompatible materials including stainless steel, titanium, ceramics, nitinol, polymers, and other materials known in the art.

The above description has included some references to use to allow for a better understanding of the structure. Below is a more detailed discussion of that use including the devices and techniques for distracting and retaining a facet joint in a distracted and forwardly translated condition. The implantation procedure may be performed under conscious sedation in order to obtain intra-operative patient symptom feedback. Before the facet joint can be distracted, however, the joint, which is difficult to access, must be accessed pursuant, for example, to a method and apparatus disclosed in U.S. provisional application Ser. No. 61/020,082, filed Jan. 9, 2008, which is commonly owned with the present application and hereby incorporated by reference. Pursuant to the disclosure in that application, the access system may include one or more cannulas made of steel, titanium, or plastic. The initial facet joint access cannula may have a sharp spatula tip on the distal end. The spatula tip may have a flat configuration to enable access into the flat facet joint. Once the spatula tip achieves access into the flatly oriented facet joint, subsequent stylets and working instruments may be passed down this access channel to complete a distraction procedure. Alternatively the chisel and delivery device described above may be used to access the joint. The distraction procedure may then begin.

The percutaneous distraction system may be introduced down the working cannula of the above-identified access system using a handle or delivery tool that would allow the surgeon to generate distraction by applying energy to the handle for a distraction device at the proximal end of the device.

A distraction device may be inserted down the working cannula, for example of the access system described previously, which is docked in a facet joint. Once the distal end of the distraction device is positioned at the anterior aspect of the joint, the surgeon applies energy to the distraction device to create separation and distraction of the facet joint. This separation occurs in both the vertical and horizontal planes of the joint resulting in vertical distraction and forward/anterior translation of the superior vertebrae relative to the inferior vertebrae. The facet joint distraction and forward translation will cause an increase in foraminal area and may reduce nerve root compression and associated symptoms.

Although the present invention has been described with a certain degree of particularity, it is understood the disclosure has been made by way of example, and changes in detail or structure may be made without departing from the spirit of the invention as defined in the appended claims.

What is claimed is:

1. A spinal joint distraction system, comprising:
   a driver assembly comprising:
      a first tubular shaft having a longitudinal axis; and
      first and second implant engagement faces positioned on a distal end of the first tubular shaft, each face configured to engage at least a portion of a spinal implant; and
   a delivery device comprising:
      a second tubular shaft defining a lumen;
      a receiving assembly including the lumen for receiving the driver assembly, the receiving assembly positioned on a proximal end of the second tubular shaft; and
      a pair of tines extending from a distal end of the second tubular shaft, the tines adapted to penetrate a facet joint,
   wherein, the second tubular shaft slidably receives the driver assembly.

2. The spinal joint distraction system of claim 1 further comprising a chisel including a shaft having a proximal end and a distal end opposite the proximal end, the distal end including a tip.

3. The spinal joint distraction system of claim 2 wherein the tip of the chisel is a single or doubly chamfered tip.

4. The spinal joint distraction system of claim 2 wherein the shaft of the chisel is adapted to be received within an inner radius of the second tubular shaft.

5. The spinal joint distraction system of claim 1 further comprising a decorticator comprising a tubular shaft portion having a distal portion with an abrasive distal end.

6. The spinal joint distraction system of claim 5 wherein the abrasive distal end of the distal portion of the tubular shaft portion of the decorticator includes a plurality of teeth.

7. The spinal joint distraction system of claim 5 wherein the tubular shaft portion of the decorticator has a shaft adapted to be received by the second tubular shaft.

8. The spinal joint distraction system of claim 1 further comprising an implant received by the implant engagement faces, the implant comprising a first surface opposite a second surface, each of the first and second surfaces including teeth.

* * * * *